United States Patent [19]

Tsuchiya et al.

[11] Patent Number: 5,750,540
[45] Date of Patent: May 12, 1998

[54] 1,4-DI-SUBSTITUTED PIPERIDINE DERIVATIVES

[75] Inventors: Yoshimi Tsuchiya; Takashi Nomoto; Hirokazu Ohsawa; Kumiko Kawakami; Kenji Ohwaki; Masaru Nishikibe, all of Tsukuba, Japan

[73] Assignee: Banyu Pharmaceutical Co., Ltd., Tokyo, Japan

[21] Appl. No.: 682,785

[22] PCT Filed: Apr. 25, 1996

[86] PCT No.: PCT/JP96/01128

§ 371 Date: Jul. 31, 1996

§ 102(e) Date: Jul. 31, 1996

[87] PCT Pub. No.: WO96/33973

PCT Pub. Date: Oct. 31, 1996

[30] Foreign Application Priority Data

Apr. 28, 1995 [JP] Japan .................. 7-129827

[51] Int. Cl.$^6$ .................. A61K 31/445; A61K 31/505; C07D 401/12; C07D 211/46
[52] U.S. Cl. .................. 514/318; 514/256; 514/317; 514/326; 544/242; 544/233; 546/194; 546/208; 546/209; 546/210; 546/213; 546/214; 546/222; 546/224
[58] Field of Search .................. 514/256, 317, 514/318, 326; 544/242, 333; 546/194, 208, 209, 210, 213, 214, 222, 224

[56] References Cited

U.S. PATENT DOCUMENTS

| | | | |
|---|---|---|---|
| 4,721,722 | 1/1988 | Davis | 514/317 |
| 4,843,074 | 6/1989 | Rzeszotarski et al. | 514/228.2 |
| 5,246,945 | 9/1993 | Kikuchi et al. | 514/331 |
| 5,482,940 | 1/1996 | Abou-Gharbia et al. | 514/252 |

FOREIGN PATENT DOCUMENTS 1131145  5/1989  Japan .

OTHER PUBLICATIONS

Ge et al. "Synthesis and anticholinergic activity of . . . " CA 105:226282, 1985.
Tejani-Butt et al. "N-substituted derivatives of 4-piperidinyl benzilate . . . " Life Sci. v.47, pp. 841-848, 1990.
Okada et al. "Preparation of N-piperidinylhydroxyacetamides . . . " CA 126:144121, 1997.
Basic and Clinical Pharmacology, 4th ed., Appleton & Lange, pp. 83-92.
Drug News & Perspective 5(6), pp. 345-352 (1992).
Otto, C.A., et al., Int. J. Radiat. Appl. Instrum. Part B, Nucl. Med. Bio., vol. 16, No. 1 (1989) pp. 51-55.
Tang, L.C. et al., Gen. Pharmac., vol. 22, No. 3 (1991), pp. 485-490.

*Primary Examiner*—Ceila Chang
*Attorney, Agent, or Firm*—Sherman and Shalloway

[57] ABSTRACT

This invention provides novel 1,4-di-substituted piperidine derivatives of the general formula [I]

$$HO-\underset{R^1}{\underset{|}{C}}(Ar)-\overset{O}{\underset{\|}{C}}-X-\langle\text{ring}\rangle-N-R^2$$

and the pharmaceutically acceptable salts thereof, wherein:
  Ar represents a phenyl group or a five- or six-membered heteroaromatic group having one or two hetero atoms selected from the group consisting of an oxygen atom, a sulfur atom and a nitrogen atom in which one or two optional hydrogen atoms on the ring may be replaced by substituent groups selected from the group consisting of a halogen atom and a lower alkyl group;
  $R^1$ represents a cycloalkyl group of 3 to 6 carbon atoms or a cycloalkenyl group of 3 to 6 carbon atoms;
  $R^2$ represents a saturated or unsaturated aliphatic hydrocarbon radical of 5 to 15 carbon atoms; and
  X represents O or NH.

These compounds have selective antagonistic activity against the muscarinic $M_3$ receptors and can hence be used safely with a minimum of side effects.

18 Claims, No Drawings

1,4-DI-SUBSTITUTED PIPERIDINE DERIVATIVES

This application is a 371 of PCT/JP96/01128 filed Apr. 25, 1996, published as WO96/33973 Oct. 31, 1996.

TECHNICAL FIELD

This invention relates to novel 1,4-di-substituted piperidine derivatives, processes for preparing them, and their use in medicine, especially in the treatment or prophylaxis of various diseases of the respiratory, urinary and digestive systems.

BACKGROUND ART

Compounds having antagonistic activity against muscarinic receptors are known to cause bronchodilation, gastrointestinal hypanakinesis, gastric hyposecretion, thirst, mydriasis, suppression of bladder contraction, hypohidrosis, tachycardia and the like ["Basic and Clinical Pharmacology", 4th ed., APPLETON & LANGE, pp. 83–92 (1989); Drug News & Perspective, 5(6), pp. 345–352 (1992) ].

There are three subtypes of muscarinic receptors. That is, the $M_1$ receptors are present mainly in the brain, the $M_2$ receptors in the heart and the like, and the $M_3$ receptors on smooth muscles and glandular tissues. Up to this time, a large number of compounds have been known to exhibit antagonism against muscarinic receptors. However, the existing compounds non-selectively antagonize the three subtypes of muscarinic receptors. Consequently, when it is tried to use these compounds as therapeutic or prophylactic agents for diseases of the respiratory system, they have the disadvantage of causing side effects such as thirst, nausea and mydriasis, particularly serious side effects associated with the heart, such as tachycardia mediated by the $M_2$ receptors. Accordingly, it would be highly desirable to overcome this disadvantage.

DISCLOSURE OF THE INVENTION

According to the present invention, there are provided novel 1,4-di-substituted piperidine derivatives of the general formula [I]

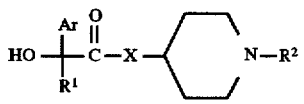

and the pharmaceutically acceptable salts thereof, wherein:

Ar represents a phenyl group or a five- or six-membered heteroaromatic group having one or two hetero atoms selected from the group consisting of an oxygen atom, a sulfur atom and a nitrogen atom in which one or two hydrogen atoms on the ring may be replaced by substituent groups selected from the group consisting of a halogen atom and a lower alkyl group;

$R^1$ represents a cycloalkyl group of 3 to 6 carbon atoms or a cycloalkenyl group of 3 to 6 carbon atoms;

$R^2$ represents a saturated or unsaturated aliphatic hydrocarbon radical of 5 to 15 carbon atoms; and X represents O or NH.

The compounds of the above general formula [I] which are provided by the present invention have high and selective antagonistic activity against the muscarinic $M_3$ receptors and can hence be used safely with a minimum of side effects. Accordingly, they are very useful in the treatment or prophylaxis of diseases of the respiratory system, such as asthma, chronic airway obstruction and fibroid lung; diseases of the urinary system accompanied by urination disorders such as pollakiuria, urinary urgency and urinary incontinence; and diseases of the digestive system, such as irritable colon and spasm or hyperanakinesis of the digestive tract.

BEST MODE FOR CARRYING OUT THE INVENTION

The present invention is more specifically described hereinbelow.

As used herein, the term "halogen atom" comprehends fluorine, chlorine, bromine and iodine atoms.

The term "lower alkyl group" means linear or branched alkyl groups having 1 to 6 carbon atoms, and comprehends, for example, methyl, ethyl, propyl, isopropyl, butyl, sec-butyl, tert-butyl, pentyl, isopentyl, hexyl and isohexyl.

The term "five- or six-membered heteroaromatic group" comprehends, for example, 2-pyrrolyl , 3-pyrrolyl 2-furyl, 3-furyl, 2-thienyl, 3-thienyl, 3-pyrazolyl, 4-pyrazolyl, 3-isoxazolyl, 5-isoxazolyl, 3-isothiazolyl, 4-isothiazolyl, 5-isothiazolyl, 2-imidazolyl, 4-imidazolyl, 2-oxazolyl, 4-oxazolyl, 5-oxazolyl, 2-thiazolyl, 4-thiazolyl, 5-thiazolyl, 2-pyridyl, 3-pyridyl, 4-pyridyl, 3-pyridazinyl, 4-pyridazinyl, 2-pyrimidinyl, 4-pyrimidinyl and 2-pyrazinyl.

The term "cycloalkyl group of 3 to 6 carbon atoms" comprehends, for example, cyclopropyl, cyclobutyl, cyclopentyl and cyclohexyl.

The term "cycloalkenyl group of 3 to 6 carbon atoms" comprehends, for example, cyclopropenyl, cyclobutenyl, cyclopentenyl and cyclohexenyl.

The term "saturated or unsaturated aliphatic hydrocarbon radical of 5 to 15 carbon atoms" means linear or branched aliphatic hydrocarbon radicals having 5 to 15 carbon atoms, and comprehends, for example, alkyl, alkenyl and alkynyl groups, cycloalkylalkyl and cycloalkylalkenyl groups in which an optional hydrogen atom(s) on the cycloalkyl ring may be replaced by a lower alkyl group(s), bicycloalkylalkyl and bicycoalkylalkenyl groups in which an optional hydrogen atom(s) on the bicycloalkyl ring may be replaced by a lower alkyl group(s), cycloalkenylalkyl and cyloalkenylalkenyl groups in which an optional hydrogen atom(s) on the cycloalkenyl ring may be replaced by a lower alkyl group(s), bicycloalkenylalkyl and bicycloalkenylalkenyl groups in which an optional hydrogen atom(s) on the bicycloalkenyl ring may be replaced by a lower alkyl group(s), and cycloalkylalkynyl and cycloalkenylalkynyl groups.

Specific examples of such aliphatic hydrocarbon radicals include:

alkyl groups such as 1-methylbutyl, 2-methylbutyl, 3-methylbutyl, pentyl, neopentyl, tert-pentyl, 1-methylpentyl, 2-methylpentyl, 3-methylpentyl, 4-methylpentyl, hexyl, isohexyl, 1-methylhexyl, 2-methylhexyl, 3-methylhexyl, 4-methylhexyl 5-methylhexyl, 2,4-dimethylpentyl, 2-ethylhexyl, 4,5-dimethylhexyl, 4,4-dimethylpentyl, heptyl, 4-methylheptyl, octyl, nonyl, decyl, undecyl, dodecyl, tridecyl, tetradecyl and pentadecyl;

alkenyl groups such as 3-methyl-2-butenyl, 2-pentenyl, 3-pentenyl, 4-pentenyl, 3-methyl-2-pentenyl, 3-methyl-3-pentenyl, 4-methyl-2-pentenyl, 4-methyl-3-pentenyl, 4-methyl-4-pentenyl, 2-hexenyl, 3-hexenyl, 4-hexenyl, 4-methyl-2-hexenyl, 4-methyl-3-hexenyl, 4-methyl-4-hexenyl, 5-methyl-2-hexenyl, 5-methyl-3-hexenyl, 5-methyl-4-hexenyl, 5-methyl-2-heptenyl, 5-methyl-3-heptenyl, 5-methyl-4-heptenyl, 5-methyl-5-heptenyl, 3,5-dimethyl-2-pentenyl, 3,5-dimethyl-3-pentenyl, 4,5-dimethyl-2-hexenyl, 4,5-dimethyl-3-hexenyl, 4,5-dimethyl-4-hexenyl, octenyl, nonenyl, decenyl, undecenyl, dodecenyl, tridecenyl, tetradecenyl and pentadecenyl;

alkynyl groups such as 2-pentynyl, 3-pentynyl, 4-pentynyl, 4-methyl-2-pentynyl, 4-methyl-3-pentynyl, 4-methyl-4-pentynyl, 2-hexynyl, 3-hexynyl, 4-hexynyl, 4-methyl-2-hexynyl, 4-methyl-3-hexynyl, 4-methyl-4-hexynyl, octynyl, nonynyl, decynyl, undecynyl, dodecynyl, tridecynyl, tetradecynyl and pentadecynyl;

cycloalkylalkyl groups in which an optional hydrogen atom(s) on the cycloalkyl ring may be replaced by a lower alkyl group(s), such as cyclopropylethyl, cyclopropylpropyl, cyclopropylbutyl, cyclopropylpentyl, cyclopropylhexyl, cyclopropylheptyl, cyclobutylmethyl, cyclobutylethyl, cyclobutylpropyl, cyclobutylbutyl, cyclobutylpentyl, cyclopentylmethyl, cyclopentylethyl, cyclopentylpropyl, cyclopentylbutyl, cyclohexylmethyl, cyclohexylethyl, cyclohexylpropyl, cyclohexylbutyl, cycloheptylmethyl, cycloheptylethyl, cycloheptylpropyl, cycloheptylbutyl, cyclooctylmethyl, cyclooctylethyl, cyclooctylpropyl, cyclooctylbutyl, 1-methylcyclopentylmethyl, 2-methylcyclopentylmethyl, 3-methylcyclopentylmethyl, 1-ethylcyclopentylmethyl, 2-ethylcyclopentylmethyl, 3-ethylcyclopentylmethyl, 2-cyclopentylethyl, 2-(1-methylcyclopentyl)ethyl, 2-(2-methylcyclopentyl)ethyl, 2-(3-methylcyclopentyl)ethyl, 2-(1-ethylcyclopentyl)ethyl, 2-(2-ethylcyclopentyl)ethyl, 2-(3-ethylcyclopentyl)ethyl, 1-methylcyclohexylmethyl, 2-methylcyclohexylmethyl, 3-methylcyclohexylmethyl, 4-methylcyclohexylmethyl, 1-ethylcyclohexylmethyl, 2-ethylcyclohexylmethyl, 3-ethylcyclohexylmethyl, 4-ethylcyclohexylmethyl, cyclohexylethyl, 2-(1-methylcyclohexyl)ethyl, 2-(2-methylcyclohexyl)ethyl, 2-(3-methylcyclohexyl)ethyl, 2-(4-methylcyclohexyl)ethyl, 2-(1-ethylcyclohexyl)ethyl, 2-(2-ethylcyclohexyl)ethyl, 2-(3-ethylcyclohexyl)ethyl, 2-(4-ethylcyclohexyl)ethyl, 1-methylcycloheptylmethyl, 2-methylcycloheptylmethyl, 3-methylcycloheptylmethyl, 4-methylcycloheptylmethyl, 1-ethylcycloheptylmethyl, 2-ethylcycloheptylmethyl, 3-ethylcycloheptylmethyl, 4-ethylcycloheptylmethyl, 2-cycloheptylethyl, 2-(1-methylcycloheptyl)ethyl, 2-(2-methylcycloheptyl)ethyl, 2-(3-methylcycloheptyl)ethyl, 2-(4-methylcycloheptyl)ethyl, 2-(1-ethylcycloheptyl)ethyl, 2-(2-ethylcycloheptyl)ethyl, 2-(3-ethylcycloheptyl)ethyl, 2-(4-ethylcycloheptyl)ethyl, 1-methylcyclooctylmethyl, 2-methylcyclooctylmethyl, 3-methylcyclooctylmethyl, 4-methylcyclooctylmethyl, 5-methylcyclooctylmethyl, 1-ethylcyclooctylmethyl, 2-ethylcyclooctylmethyl, 3-ethylcyclooctylmethyl, 4-ethylcyclooctylmethyl, 5-ethylcyclooctylmethyl, 2-(1-methylcyclooctyl)ethyl, 2-(2-methylcyclooctyl)ethyl, 2-(3-methylcyclooctyl)ethyl, 2-(4-methylcyclooctyl)ethyl, 2-(5-methylcyclooctyl)ethyl, 2-(1-ethylcyclooctyl)ethyl, 2-(2-ethylcyclooctyl)ethyl, 2-(3-ethylcyclooctyl)ethyl, 2-(4-ethylcyclooctyl)ethyl and 2-(5-ethylcyclooctyl)ethyl;

cycloalkylidenealkyl groups such as cyclopropylideneethyl, cyclopropylidenepropyl, cyclopropylidenebutyl, cyclopropylidenepentyl, cyclobutylideneethyl, cyclobutylidenepropyl, cyclobutylidenebutyl, cyclobutylidenepentyl, cyclopentylideneethyl, cyclopentylidenepropyl, cyclopentylidenebutyl, cyclopentylidenepentyl, cyclohexylideneethyl, cyclohexylidenepropyl, cyclohexylidenebutyl, cyclohexylidenepentyl, cycloheptylideneethyl, cycloheptylidenepropyl, cycloheptylidenebutyl, cycloheptylidenepentyl, cyclooctylideneethyl, cyclooctylidenepropyl, cyclooctylidenebutyl and cyclooctylidenepentyl;

cycloalkylalkenyl groups such as cyclopropylpropenyl, cyclopropylbutenyl, cyclopropylpentenyl, cyclopropylhexenyl, cyclopropylheptenyl, cyclobutylpropenyl, cyclobutylbutenyl, cyclobutylpentenyl, cyclopentylpropenyl, cyclopentylbutenyl, cyclopentylpentenyl, cyclohexylpropenyl, cyclohexylbutenyl, cyclohexylpentenyl, cycloheptylpropenyl and cyclooctylpropenyl;

bicycloalkylalkyl groups in which an optional hydrogen atom(s) on the bicycloalkyl ring may be replaced by a lower alkyl group(s), such as bicyclo[4.1.0]hept-1-ylmethyl, bicyclo[4.1.0]hept-2-ylmethyl, bicyclo[4.1.0]hept-3-ylmethyl, bicyclo[4.1.0]hept-7-ylmethyl, bicyclo[3.3.0]oct-1-ylmethyl, bicyclo[3.3.0]oct-2-ylmethyl, bicyclo[3.3.0]oct-3-ylmethyl, bicyclo[4.1.0]hept-1-ylethyl, bicyclo[4.1.0]hept-2-ylethyl, bicyclo[4.1.0]hept-3-ylethyl, bicyclo[4.1.0]hept-7-ylethyl, bicyclo[3.3.0]oct-1-ylethyl, bicyclo[3.3.0]oct-2-ylethyl, bicyclo[3.3.0]oct-3-ylethyl, bicyclo[3.2.1]oct-1-ylmethyl, bicyclo[3.2.1]oct-2-ylmethyl, bicyclo[3.2.1]oct-3-ylmethyl, bicyclo[3.2.1]oct-8-ylmethyl, bicyclo[4.4.0]dec-1-ylmethyl, bicyclo[4.4.0]dec-2-ylmethyl, bicyclo[4.4.0]dec-3-ylmethyl, bicyclo[4.3.0]non-1-ylmethyl, bicyclo[4.3.0]non-2-ylmethyl, bicyclo[4.3.0]non-3-ylmethyl, bicyclo[4.3.0]non-7-ylmethyl, bicyclo[3.3.1]non-1-ylmethyl, bicyclo[3.3.1]non-2-ylmethyl, bicyclo[3.3.1]non-3-ylmethyl, bicyclo[3.3.1]non-9-ylmethyl, bicyclo[3.1.0]hex-1-ylmethyl, bicyclo[3.1.0]hex-2-ylmethyl, bicyclo[3.1.0]hex-3-ylmethyl and bicyclo[3.1.0]hex-6-ylmethyl;

bicycloalkylalkenyl groups in which an optional hydrogen atom(s) on the bicycloalkyl ring may be replaced by a lower alkyl group(s), such as bicyclo[4.1.0]hept-1-ylethenyl, bicyclo[4.1.0]hept-2-ylethenyl, bicyclo[4.1.0]hept-3-ylethenyl and bicyclo[4.1.0]hept-7-ylethenyl;

cycloalkylalkynyl groups such as cyclopropylpropynyl, cyclopropylbutynyl, cyclopropyl pentynyl, cyclopropylhexynyl, cyclopropylheptynyl, cyclobutylpropynyl, cyclobutylbutynyl, cyclobutylpentynyl, cyclopentylpropynyl, cyclopentylbutynyl, cyclopentylpentynyl, cyclohexylpropynyl, cyclohexylbutynyl and cyclohexylpentynyl;

cycloalkenylalkyl groups in which an optional hydrogen atom(s) on the cycloalkenyl ring may be replaced by a lower alkyl group(s), such as cyclopropenylethyl, cyclopropenylpropyl, cyclopropenylbutyl, cyclopropenylpentyl, cyclopropenylhexyl, cyclopropenyl heptyl cyclobutenylmethyl, cyclobutenylethyl, cyclobutenylpropyl, cyclopentenylmethyl, cyclohexenylmethyl, cyclohexenylethyl, cycloheptenylmethyl, cycloheptenylethyl, cyclooctenylmethyl, cyclooctenylethyl, (1-methyl-1-cyclopentenyl)methyl, (1-methyl-2-cyclopentenyl)methyl, (1-methyl-3-cyclopentenyl)methyl, (2-methyl-1-cyclopentenyl)methyl, (2-methyl-2-cyclopentenyl)methyl, (2-methyl-3-cyclopentenyl)methyl, (2-methyl-4-cyclopentenyl)methyl, (2-methyl-5-cyclopentenyl)methyl, (3-methyl-1-cyclopentenyl)methyl, (3-methyl-2-cyclopentenyl)methyl, (3-methyl-3-cyclopentenyl)methyl, (3-methyl-4-cyclopentenyl)methyl, (3-methyl-5-cyclopentenyl)methyl, (1-methyl-1-cyclohexenyl)methyl, (1-methyl-2-cyclohexenyl)methyl, (1-methyl-3-cyclohexenyl)methyl, (2-methyl-1-cyclohexenyl)methyl, (2-methyl-2-cyclohexenyl)methyl, (2-methyl-3-cyclohexenyl)methyl, (2-methyl-4-cyclohexenyl)methyl, (2-methyl-5-cyclohexenyl)methyl, (2-methyl-6-cyclohexenyl)methyl, (3-methyl-1-cyclohexenyl)methyl, (3-methyl-2-cyclohexenyl)methyl, (3-methyl-3-cyclohexenyl)methyl, (3-methyl-4-cyclohexenyl)methyl, (3-methyl-5-cyclohexenyl)methyl, (3-methyl-6-cyclohexenyl)methyl, (4-methyl-1-cyclohexenyl)methyl, (4-methyl-2-cyclohexenyl)methyl, (4-methyl-3-cyclohexenyl)methyl, (1-methyl-1-cycloheptenyl)methyl, (1-methyl-2-cycloheptenyl)methyl, (1-methyl-3-cycloheptenyl)methyl, (1-methyl-4-cycloheptenyl)methyl, (2-methyl-1-cycloheptenyl)methyl, (2-methyl-2-cycloheptenyl)methyl, (2-methyl-3-cycloheptenyl)methyl, (2-methyl-4-cycloheptenyl)methyl, (2-methyl-5-cycloheptenyl)methyl, (2-methyl-6-cycloheptenyl)methyl, (2-methyl-7-cycloheptenyl)methyl, (3-methyl-1-cycloheptenyl)methyl, (3-methyl-2-cycloheptenyl)methyl, (3-methyl-3-cycloheptenyl)methyl, (3-methyl-4-cycloheptenyl)methyl, (3-methyl-5-cycloheptenyl)methyl, (3-methyl-6-cycloheptenyl)methyl, (3-methyl-7-cycloheptenyl)methyl, (4-methyl-1-cycloheptenyl)methyl, (4-methyl-2-cycloheptenyl)methyl, (4-methyl-3-cycloheptenyl)methyl, (4-methyl-4-cycloheptenyl)methyl, (4-methyl-5-cycloheptenyl)methyl, (4-methyl-6-cycloheptenyl)methyl, (4-methyl-7-cycloheptenyl)methyl, (1-methyl-1-cyclooctenyl)methyl, (1-methyl-2-cyclooctenyl)methyl, (1-methyl-3-cyclooctenyl)methyl, (1-methyl-4-cyclooctenyl)methyl, (2-methyl-1-cyclooctenyl)methyl, (2-methyl-2-cyclooctenyl)methyl, (2-methyl-3-cyclooctenyl)methyl, (2-methyl-4-cyclooctenyl)methyl, (2-methyl-5-cyclooctenyl)methyl, (2-methyl-6-cyclooctenyl)methyl, (2-methyl-7-cyclooctenyl)methyl, (2-methyl-8-cyclooctenyl)methyl, (3-methyl-1-cyclooctenyl)methyl, (3-methyl-2-cyclooctenyl)methyl, (3-methyl-3-cyclooctenyl)methyl, (3-methyl-4-cyclooctenyl)methyl, (3-methyl-5-cyclooctenyl)methyl, (3-methyl-6-cyclooctenyl)methyl, (3-methyl-7-cyclooctenyl)methyl, (3-methyl-8-cyclooctenyl)methyl, (4-methyl-1-cyclooctenyl)methyl, (4-methyl-2-cyclooctenyl)methyl, (4-methyl-3-cyclooctenyl)methyl, (4-methyl-4-cyclooctenyl)methyl, (4-methyl-5-cyclooctenyl)methyl, (4-methyl-6-cyclooctenyl)methyl, (4-methyl-7-cyclooctenyl)methyl, (4-methyl-8-cyclooctenyl)methyl, (5-methyl-1-cyclooctenyl)methyl, (5-methyl-2-cyclooctenyl)methyl, (5-methyl-3-cyclooctenyl)methyl and (5-methyl-4-cyclooctenyl)methyl;

bicycloalkenylalkyl groups in which an optional hydrogen atom(s) on the bicycloalkenyl ring may be replaced by a lower alkyl group(s), such as bicyclo[4.1.0]hept-2-en-1-ylmethyl, bicyclo[4.1.0]hept-3-en-1-ylmethyl, bicyclo[4.1.0]hept-4-en-1-ylmethyl, bicyclo[4.1.0]hept-3-en-2-ylmethyl, bicyclo[4.1.0]hept-4-en-2-ylmethyl, bicyclo[4.1.0]hept-2-en-3-ylmethyl, bicyclo[4.1.0]hept-3-en-3-ylmethyl, bicyclo[4.1.0]hept-4-en-3-ylmethyl, bicyclo[4.1.0]hept-2-en-7-ylmethyl, bicyclo[3.3.0]oct-2-en-2-ylmethyl, bicyclo[3.3.0]oct-2-en-3-ylmethyl, bicyclo[4.1.0]hept-2-en-1-ylethyl, bicyclo[4.1.0]hept-2-en-2-ylethyl, bicyclo[4.1.0]hept-2-en-3-ylethyl, bicyclo[4.1.0]hept-2-en-4-ylethyl, bicyclo[4.1.0]hept-2-en-7-ylethyl, bicyclo[3.3.0]oct-2-en-1-ylethyl, bicyclo[3.3.0]oct-2-en-2-ylethyl and bicyclo[3.3.0]oct-2-en-3-ylethyl;

bicycloalkenylalkenyl groups in which an optional hydrogen atom(s) on the bicycloalkenyl ring may be replaced by a lower alkyl group(s), such as bicyclo[4.1.0]hept-2-en-1-ylethenyl, bicyclo[4.1.0]hept-3-en-1-ylethenyl, bicyclo[4.1.0]hept-4-en-1-ylethenyl, bicyclo[4.1.0]hept-3-en-2-ylethenyl, bicyclo[4.1.0]hept-4-en-2-ylethenyl, bicyclo[4.1.0]hept-2-en-3-ylethenyl, bicyclo[4.1.0]hept-3-en-3-ylethenyl, bicyclo[4.1.0]hept-4-en-3-ylethenyl, bicyclo[4.1.0]hept-2-en-7-ylethenyl, bicyclo[3.3.0]oct-2-en-2-ylethenyl and bicyclo[3.3.0]oct-2-en-3-ylethenyl;

cycloalkenylalkenyl groups such as cyclopropenylpropenyl, cyclopropenylbutenyl, cyclobutenylbutenyl, cyclopentenylpropenyl, cyclopentenylbutenyl, cyclopropenylpentenyl, cyclopropenylhexenyl, cyclopropenylheptenyl, cyclobutenylpropenyl, cyclohexenylpropenyl and cyclohexenylbutenyl; and cycloalkenylalkynyl groups such as cyclopropenylpropynyl, cyclopropenylbutynyl, cyclopropenylpentynyl, cyclopropenylhexynyl, cyclopropenylheptynyl, cyclobutenylpropynyl, cyclobutenylbutynyl, cyclopentenylpropynyl, cyclopentenylbutynyl, cyclohexenylpropynyl and cyclohexenylbutynyl.

In the above general formula [I]:

(1) Ar represents a phenyl group or a five- or six-membered heteroaromatic group having one or two hetero atoms selected from the group consisting of an oxygen atom, a sulfur atom and a nitrogen atom in which one or two optional hydrogen atoms on the ring may be replaced by substituent groups selected from the group consisting of a halogen atom and a lower alkyl group. Preferably, Ar is a phenyl group or a heteroaromatic group such as 2-pyrrolyl, 3-pyrrolyl, 2-furyl, 3-furyl, 2-thienyl, 3-thienyl, 3-pyrazolyl, 4-pyrazolyl, 3-isoxazolyl, 5-isoxazolyl, 2-imidazolyl, 4-imidazolyl, 2-oxazolyl, 4-oxazolyl, 5-oxazolyl, 2-thiazolyl, 4-thiazolyl, 5-thiazolyl, 2-pyridyl, 4-pyridyl, 2-pyrimidinyl or 4-pyrimidinyl, in which one or two optional hydrogen atoms on the ring may be replaced by substituent groups selected from the group consisting of a fluorine atom and a methyl group.

(2) $R^1$ represents a cycloalkyl group of 3 to 6 carbon atoms or a cycloalkenyl group of 3 to 6 carbon atoms. Preferably, $R^1$ is a cyclopropyl, cyclobutyl, cyclopentyl or cyclopentenyl group.

(3) X represents O or NH. Preferably, X is NH.

(4) $R^2$ represents a saturated or unsaturated aliphatic hydrocarbon radical of 5 to 15 carbon atoms.

Preferably, R² is a group of the formula [II]

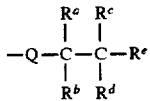

in which
- Q represents an alkylene group of 1 to 4 carbon atoms, such as methylene, ethylene, trimethylene or tetramethylene;
- $R^a$ and $R^c$ each represent a hydrogen atom or are combined to form a single bond; and
- $R^b$, $R^d$ and $R^e$ may be the same or different and each represent a hydrogen atom, a lower alkyl group or a cycloalkyl, cycloalkenyl, bicycloalkyl or bicycloalkenyl group of 3 to 8 carbon atoms or $R^b$ and $R^d$, or $R^d$ and $R^e$, are combined to form a cycloalkyl, cycloalkenyl, bicycloalkyl or bicycloalkenyl group of 3 to 8 carbon atoms.

In addition to the compounds described in the examples which will be given later, specific examples of the compounds of formula [I] in accordance with the present invention include:

N-[1-(3-methylhexyl)piperidin-4-yl]-2-cyclopentyl-2-hydroxy-2-phenylacetamide.
N-[1-(5-methylhexyl)piperidin-4-yl]-2-cyclopentyl-2-hydroxy-2-phenylacetamide.
N-[1-(3,3-dimethylheptyl)piperidin-4-yl]-2-cyclopentyl-2-hydroxy-2-phenylacetamide.
N-[1-(2-methylheptyl)piperidin-4-yl]-2-cyclopentyl-2-hydroxy-2-phenylacetamide.
N-[1-(3-methylheptyl)piperidin-4-yl]-2-cyclopentyl-2-hydroxy-2-phenylacetamide.
N-[1-(3-ethylhexyl)piperidin-4-yl]-2-cyclopentyl-2-hydroxy-2-phenylacetamide.
N-[1-(3-ethylheptyl)piperidin-4-yl]-2-cyclopentyl-2-hydroxy-2-phenylacetamide.
N-[1-(E)-(3-methyl-2-hexenyl)piperidin-4-yl]-2-cyclopentyl-2-hydroxy-2-phenylacetamide.
N-[1-(Z)-(3-methyl-2-hexenyl)piperidin-4-yl]-2-cyclopentyl-2-hydroxy-2-phenylacetamide.
N-[1-(E)-(4-methyl-3-octenyl)piperidin-4-yl]-2-cyclopentyl-2-hydroxy-2-phenylacetamide.
N-[1-(Z)-(4-methyl-3-octenyl)piperidin-4-yl]-2-cyclopentyl-2-hydroxy-2-phenylacetamide.
N-[1-(E)-(3-methyl-3-hexenyl)piperidin-4-yl]-2-cyclopentyl-2-hydroxy-2-phenylacetamide.
N-[1-(Z)-(3-methyl-3-hexenyl)piperidin-4-yl]-2-cyclopentyl-2-hydroxy-2-phenylacetamide.
N-[1-(3-hexynyl)piperidin-4-yl]-2-cyclopentyl-2-hydroxy-2-phenylacetamide.
N-[1-(3-methyl-4-pentynyl)piperidin-4-yl]-2-cyclopentyl-2-hydroxy-2-phenylacetamide.
N-{1-[2-(2-methylcyclopentyl)ethyl]piperidin-4-yl}-2-cyclopentyl-2-hydroxy-2-phenylacetamide.
N-[1-(3-cyclohexylpropyl)piperidin-4-yl]-2-cyclopentyl-2-hydroxy-2-phenylacetamide.
N-(1-cycloheptylmethylpiperidin-4-yl)-2-cyclopentyl-2-(3-furyl)-2-hydroxyacetamide.
N-(1-cycloheptylmethylpiperidin-4-yl)-2-cyclopentyl-2-hydroxy-2-(3-pyrazolyl)acetamide.
N-(1-cycloheptylmethylpiperidin-4-yl)-2-cyclopentyl-2-hydroxy-2-(4-pyrazolyl)acetamide.
N-(1-cycloheptylmethylpiperidin-4-yl)-2-cyclopentyl-2-hydroxy-2-(3-isoxazolyl)acetamide.
N-(1-cycloheptylmethylpiperidin-4-yl)-2-cyclopentyl-2-hydroxy-2-(4-isoxazolyl)acetamide.
N-(1-cycloheptylmethylpiperidin-4-yl)-2-cyclopentyl-2-hydroxy-2-(5-isoxazolyl)acetamide.
N-(1-cycloheptylmethylpiperidin-4-yl)-2-cyclopentyl-2-hydroxy-2-(3-isothiazolyl)acetamide.
N-(1-cycloheptylmethylpiperidin-4-yl)-2-cyclopentyl-2-hydroxy-2-(4-isothiazolyl)acetamide.
N-(1-cycloheptylmethylpiperidin-4-yl)-2-cyclopentyl-2-hydroxy-2-(5-isothiazolyl)acetamide.
N-(1-cycloheptylmethylpiperidin-4-yl)-2-cyclopentyl-2-hydroxy-2-(2-imidazolyl)acetamide.
N-(1-cycloheptylmethylpiperidin-4-yl)-2-cyclopentyl-2-hydroxy-2-(4-imidazolyl)acetamide.
N-(1-cycloheptylmethylpiperidin-4-yl)-2-cyclopentyl-2-hydroxy-2-(2-oxazolyl)acetamide.
N-(1-cycloheptylmethylpiperidin-4-yl)-2-cyclopentyl-2-hydroxy-2-(4-oxazolyl)acetamide.
N-(1-cycloheptylmethylpiperidin-4-yl)-2-cyclopentyl-2-hydroxy-2-(5-oxazolyl)acetamide.
N-(1-cycloheptylmethylpiperidin-4-yl)-2-cyclopentyl-2-hydroxy-2-(5-thiazolyl)acetamide.
N-(1-cycloheptylmethylpiperidin-4-yl)-2-cyclopentyl-2-hydroxy-2-(3-pyridyl)acetamide.
N-(1-cycloheptylmethylpiperidin-4-yl)-2-cyclopentyl-2-hydroxy-2-(4-pyridyl)acetamide.
N-(1-cycloheptylmethylpiperidin-4-yl)-2-cyclopentyl-2-hydroxy-2-(3-pyridazinyl)acetamide.
N-(1-cycloheptylmethylpiperidin-4-yl)-2-cyclopentyl-2-hydroxy-2-(4-pyridazinyl)acetamide.
N-(1-cycloheptylmethylpiperidin-4-yl)-2-cyclopentyl-2-hydroxy-2-(2-pyrimidinyl)acetamide.
N-(1-cycloheptylmethylpiperidin-4-yl)-2-cyclopentyl-2-hydroxy-2-(4-pyrimidinyl)acetamide.
N-(1-cycloheptylmethylpiperidin-4-yl)-2-cyclopentyl-2-hydroxy-2-(2-pyrazinyl)acetamide.
N-(1-cycloheptylmethylpiperidin-4-yl)-2-cyclobutyl-2-hydroxy-2-phenylacetamide.
N-(1-cycloheptylmethylpiperidin-4-yl)-2-cyclohexyl-2-hydroxy-2-phenylacetamide.
N-[1-(3-cyclohexenyl)methylpiperidin-4-yl]-2-cyclopentyl-2-hydroxy-2-phenylacetamide.
N-[1-(2-cycloheptenyl)methylpiperidin-4-yl]-2-cyclopentyl-2-hydroxy-2-phenylacetamide.
N-[1-(3-cycloheptenyl)methylpiperidin-4-yl]-2-cyclopentyl-2-hydroxy-2-phenylacetamide.
N-[1-(4-cycloheptenyl)methylpiperidin-4-yl]-2-cyclopentyl-2-hydroxy-2-phenylacetamide.
N-[1-(3-cyclobutylidenepropyl)piperidin-4-yl]-2-cyclopentyl-2-hydroxy-2-phenylacetamide.
N-[1-(3-cyclopentylideneethyl)piperidin-4-yl]-2-cyclopentyl-2-hydroxy-2-phenylacetamide.
N-[1-(E)-(4-cyclopentyl-3-pentenyl)piperidin-4-yl]-2-cyclopentyl-2-hydroxy-2-phenylacetamide.
N-[1-(Z)-(4-cyclopentyl-3-pentenyl)piperidin-4-yl]-2-cyclopentyl-2-hydroxy-2-phenylacetamide.
N-[1-(E)-(3-cyclopentyl-2-propenyl)piperidin-4-yl]-2-cyclopentyl-2-hydroxy-2-phenylacetamide.
N-[1-(Z)-(3-cyclopentyl-2-propenyl)piperidin-4-yl]-2-cyclopentyl-2-hydroxy-2-phenylacetamide.
N-[1-(E)-(4-cyclopentyl-2-butenyl)piperidin-4-yl]-2-cyclopentyl-2-hydroxy-2-phenylacetamide.
N-[1-(Z)-(4-cyclopentyl-2-butenyl)piperidin-4-yl]-2-cyclopentyl-2-hydroxy-2-phenylacetamide.
N-[1-(3-cyclopentyl-2-propenyl)piperidin-4-yl]-2-cyclopentyl-2-hydroxy-2-phenylacetamide.
N-[1-(4-cyclopentyl-2-butynyl)piperidin-4-yl]-2-cyclopentyl-2-hydroxy-2-phenylacetamide.
N-{1-[2-(1-cyclopentenyl)ethyl]piperidin-4-yl}-2-cyclopentyl-2-hydroxy-2-phenylacetamide.

N-{1-[2-(5-methyl-1-cyclopentenyl)ethyl]piperidin-4-yl}-2-cyclopentyl-2-hydroxy-2-phenylacetamide, N-{1-[(Z)-3-(1-cyclohexenyl)-2-propenyl]piperidin-4-yl}-2-cyclopentyl-2-hydroxy-2-phenylacetamide, N-{1-[(E)-3-(1-cyclohexenyl)-2-propenyl]piperidin-4-yl}-2-cyclopentyl-2-hydroxy-2-phenylacetamide, N-{1-[(E)-4-(3-cyclohexenyl)-3-butenyl]piperidin-4-yl}-2-cyclopentyl-2-hydroxy-2-phenylacetamide, N-{1-[(Z)-4-(3-cyclohexenyl)-3-butenyl]piperidin-4-yl}-2-cyclopentyl-2-hydroxy-2-phenylacetamide, N-{1-[3-(1-cyclohexenyl)-2-propynyl]piperidin-4-yl}-2-cyclopentyl-2-hydroxy-2-phenylacetamide, and N-{1-[4-(3-cyclohexenyl)-3-butynyl]piperidin-4-yl}-2-cyclopentyl-2-hydroxy-2-phenylacetamide.

According to the manner of substitution, the compounds of the present invention may exist in the form of stereoisomers such as optical isomers, diastereoisomers and geometrical isomers. It is to be understood that the compounds of the present invention also include all such stereoisomers and mixtures thereof.

Moreover, the compounds of the present invention may exist in the form of pharmaceutically acceptable salts.

Such salts include inorganic acid salts such as hydrochlorides, sulfates, nitrates, phosphates and perchlorates; organic carboxylic acid salts such as maleates, fumarates, succinates, tartrates, citrates and ascorbates; organic sulfonic acid salts such as methanesulfonates, isethionates, benzenesulfonates and p-toluenesulfonates; and the like.

The compounds of the above general formula [I] in accordance with the present invention can be prepared, for example, by:

(a) reacting a carboxylic acid of the general formula [III]

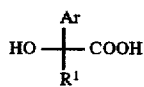

wherein Ar and $R^1$ are as defined above, or a reactive derivative thereof with a compound of the general formula [IV]

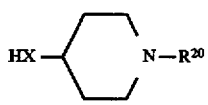

wherein $R^{20}$ represents a saturated or unsaturated aliphatic hydrocarbon radical of 5 to 15 carbon atoms or a saturated or unsaturated aliphatic hydrocarbon radical of 2 to 14 carbon atoms having a protected or unprotected oxo group, and X is as defined above, or a salt thereof; and when $R^{20}$ is a saturated or unsaturated aliphatic hydrocarbon radical of 2 to 14 carbon atoms having a protected or unprotected oxo group, deprotecting the resulting product where necessary, subjecting it to the Wittig reaction, and reducing the existing double bond where necessary;

(b) reacting a carboxylic acid of the above general formula [III] or a reactive derivative thereof with a compound of the general formula [V]

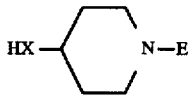

wherein E is a protective group for the imino group, and X is as defined above, or a salt thereof; deprotecting the resulting compound of the general formula [VI]

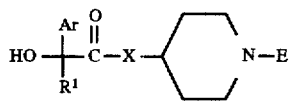

wherein Ar, $R^1$, X and E are as defined above; reacting the compound of general formula [VI] with a compound of the general formula [VII] or [VIII]

or

wherein $R^{21}$ and $R^{22}$ may be the same or different and each represent a hydrogen atom or a lower alkyl group, $R^{23}$ represents a hydrogen atom or a saturated or unsaturated aliphatic hydrocarbon radical of 1 to 12 carbon atoms, L represents a leaving group, and $R^{20}$ is as defined above, if necessary, in the presence of a base; and when a compound of general formula [VII] in which $R^{20}$ is a saturated or unsaturated aliphatic hydrocarbon radical of 2 to 14 carbon atoms having a protected or unprotected oxo group or a compound of the general formula [VIII] is reacted, deprotecting the resulting product where necessary, subjecting it to the Wittig reaction, and reducing the existing double bond where necessary; or (c) deprotecting a compound of the above general formula [VI] and subjecting it to a reductive alkylation reaction with a compound of the general formula [IX]

wherein $R^{24}$ represents a saturated or unsaturated aliphatic hydrocarbon radical of 4 to 14 carbon atoms.

In the above formulae [IV] and [VII], "saturated or unsaturated aliphatic hydrocarbon radicals of 2 to 14 carbon atoms having a protected or unprotected oxo group" represented by $R^{20}$ include, for example, groups each comprising an alkylene chain having an oxo group therein, such as $CH_2CHO$, $CH_2CH_2CHO$ and $CH_2CH_2—CO—CH_3$; and aliphatic hydrocarbon radicals each comprising an alkyl chain having therein oxo groups protected in the form of an acetal or ketal, such as $CH_2—CH(OR^6)(OR^7)$, $CH_2CH_2—CH(OR^6)(OR^7)$ and $CH_2C(CH_3)(OR^6)(OR^7)$ in which $R^6$ and $R^7$ each represent a lower alkyl group or are combined to form an ethylene or trimethylene group.

In the above formula [VII], "leaving groups" represented by L include, for example, halogen atoms such as chlorine, bromine and iodine; alkylsulfonyloxy groups such as methanesulfonyloxy; and arylsulfonyloxy groups such as p-toluenesulfonyloxy.

In the above formulae [V] and [VI], "protective groups for the imino group" represented by E include, for example, aralkyl groups such as benzyl, p-methoxybenzyl, p-nitrobenzyl, benzhydryl and trityl; lower alkanoyl groups such as formyl, acetyl and propionyl; arylalkanoyl groups such as phenylacetyl and phenoxyacetyl; lower alkoxycarbonyl groups such as methoxycarbonyl, ethoxycarbonyl and t-butoxycarbonyl; alkenyloxycarbonyl groups such as 2-propenyloxycarbonyl; aralkyloxycarbonyl groups such as benzyloxycarbonyl and p-nitrobenzyloxycarbonyl; and lower alkylsilyl groups such as trimethylsilyl and t-butyldimethylsilyl. Among others, t-butoxycarbonyl and benzyloxycarbonyl groups are preferred.

In the above-described process variant (a), a carboxylic acid of formula [III] is reacted with a compound of formula [IV] or a salt thereof in the presence of a suitable condensing agent. Thus, there is obtained a coupled compound of the general formula [X]

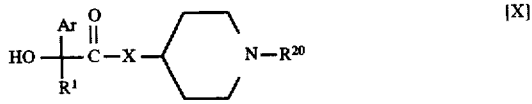

wherein Ar, $R^1$, X and $R^{20}$ are as defined above.

The carboxylic acid of formula [III] used as a starting material in the above condensation reaction can readily be prepared, for example, according to the method of S. B. Kadin [J. Org. Chem., Vol. 27, pp. 240–245 (1962)].

The condensing agent used in the above-described reaction may be any of various condensing agents that are commonly used in the field of organic synthetic chemistry for the condensation reaction of a carboxyl group with a hydroxyl or amino group, and examples thereof include N,N'-dicyclohexylcarbodiimide, 1-ethyl-3-(3-dimethylaminopropyl)carbodiimide, diphenylphosphoryl azide and dipyridyl disulfidetriphenylphosphine. Among others, 1-ethyl-3-dimethylaminopropyl)carbodiimide is preferred. Although the amount of condensing agent used is not critical, it may usually be used in an amount of 1 to 5 equivalents, preferably 1 to 2 equivalents, per mole of the compound of formula [III].

If necessary, the above-described condensation reaction may be carried out in the presence of a base. Bases which can be used for this purpose include, for example, aromatic amines such as pyridine, 4-dimethylaminopyridine, picoline, lutidine, quinoline and isoquinoline. Among others, 4-dimethylaminopyridine is preferred.

The condensation reaction is preferably carried out in an inert solvent. Suitable inert organic solvents include, for example, diethyl ether, tetrahydrofuran, N,N-dimethylformamide, dioxane, benzene, toluene, chlorobenzene, methylene chloride, chloroform, carbon tetrachloride, dichloroethane, trichloroethylene and mixtures of the foregoing solvents. Among others, diethyl ether, tetrahydrofuran, N,N-dimethylformamide and dioxane are preferred.

The reaction temperature may usually range from –70° C. to the boiling point of the solvent used for the reaction and preferably from –20° C. to 100° C. Under these conditions, the reaction can usually be completed in a period of time ranging from 5 minutes to 7 days and preferably from 10 minutes to 24 hours.

The proportion of the compound of formula [IV] or a salt thereof to the compound of formula [III] is not critical and may vary according to the types of these compounds, the reaction conditions employed and other factors. However, the compound of formula [IV] or a salt thereof may usually be used in an amount of 1 to 5 moles, preferably 1 to 2 moles, per mole of the compound of formula [III].

The coupled compound of the above formula [X] can also be obtained by converting the carboxylic acid of formula [III] into a reactive derivative thereof and condensing it with the compound of formula [IV] or a salt thereof.

Suitable reactive derivatives of the carboxylic acid of formula [III] include, for example, compounds which are commonly used in the field of organic synthetic chemistry for the activation of a carboxyl group in an esterification or amidation reaction, such as mixed acid anhydrides, active esters and active amides.

Mixed acid anhydrides of the carboxylic acid of formula [III] can be obtained by reacting the carboxylic acid of formula [III] with an alkyl chlorocarbonate (e.g., ethyl chlorocarbonate), an aliphatic carboxylic acid chloride (e.g., acetyl chloride or pivaloyl chloride) or the like according to a usual method. Active esters thereof can be obtained by reacting the carboxylic acid of formula [III] with an N-hydroxy compound (e.g., N-hydroxysuccinimide, N-hydroxyphthalimide or 1-hydroxybenzotriazole), a phenol compound (e.g., 4-nitrophenol, 2,4-dinitrophenol, 2,4,5-trichlorophenol or pentachlorophenol) or the like in the presence of a condensing agent [e.g., N,N'-dicyclohexylcarbodiimide, 1-ethyl-3-(3-dimethylaminopropyl)carbodiimide, diphenylphosphoryl azide or dipyridyl disulfide-triphenylphosphine) according to a usual method. Active amides thereof can be obtained by reacting the carboxylic acid of formula [III] with 1,1'-carbonyldiimidazole, 1,1'-carbonylbis(2-methylimidazole) or the like according to a usual method.

The condensation reaction of a reactive derivative of the compound of the carboxylic acid of formula [III] with the compound of formula [IV] or a salt thereof is preferably carried out in an inert solvent. Suitable inert organic solvents include, for example, diethyl ether, tetrahydrofuran, N,N-dimethylformamide, dioxane, benzene, toluene, chlorobenzene, methylene chloride, chloroform, carbon tetrachloride, dichloroethane, trichloroethylene and mixtures of the foregoing solvents. Among others, diethyl ether, tetrahydrofuran, N,N-dimethylformamide and dioxane are preferred.

The reaction temperature may usually range from –70° C. to the boiling point of the solvent used for the reaction and preferably from –20° C. to 100° C.

The proportion of the compound of formula [IV] or a salt thereof to the reactive derivative of the compound of formula [III] is not critical and may vary according to the type of the reactive derivative and other factors. However, the compound of formula [IV] or a salt thereof may usually be used in an amount of 1 to 5 moles, preferably 1 to 2 moles, per mole of the reactive derivative of the compound of formula [III].

When a compound of formula [IV] in which $R^{20}$ is a saturated or unsaturated aliphatic hydrocarbon radical of 5 to 15 carbon atoms is used in the above-described condensation reaction, a compound of formula [X] in which $R^{20}$ is as defined above, namely a compound of formula [I] in accordance with the present invention, is directly obtained.

On the other hand, when a compound of formula [IV] in which $R^{20}$ is a saturated or unsaturated aliphatic hydrocarbon radical of 2 to 14 carbon atoms having a protected or unprotected oxo group is used, the resulting compound of formula [X] in which $R^{20}$ is as defined above can be converted into a compound of formula [I] in accordance with the present invention, by subjecting it to the Wittig reaction, either directly or after removal of the protective group, and then reducing the existing double bond where necessary.

Removal of the protective group from the protected oxo group in the compound of formula [X] may generally be carried out in an aqueous solvent with the aid of an inorganic acid, an organic acid, a weakly acidic salt or the like. Suitable inorganic acids include, for example, hydrochloric acid and sulfuric acid; suitable organic acids include, for example, p-toluenesulfonic acid, benzenesulfonic acid, camphorsulfonic acid and acetic acid; and suitable weakly acidic salts include, for example, ammonium chloride and pyridinium p-toluenesulfonate. Preferred aqueous solvents include aqueous methanol, aqueous ethanol, aqueous tetrahydrofuran, aqueous dioxane and the like. The reaction may usually be carried out in the presence of a catalytic amount to 5 equivalents, preferably a catalytic amount to 1 equivalent, of an acid or salt as described above, at a temperature ranging from 0° C. to 100° C. and preferably from room temperature to 50° C.

The Wittig reaction is carried out, for example, by reacting the compound of formula [X], from which the protective group has been removed where necessary, with an ylide compound prepared by treating a phosphonium salt (formed from a saturated or unsaturated aliphatic hydrocarbon of 1 to 12 carbon atoms having a chlorine, bromine or iodine atom as a substituent, and triphenylphosphine) with a suitable base in an inert solvent. Suitable inert solvents include, for example, tetrahydrofuran, dioxane, diethyl ether, hexane, toluene, benzene and N,N-dimethylformamide. Suitable bases include, for example, sodium hydride, potassium hydride, sodium amide, sodium methoxide, sodium ethoxide, potassium tert-butoxide, n-butyllithium, sec-butyllithium and tert-butyllithium. Among others, sodium hydride, potassium tert-butoxide and n-butyllithium are preferably used. In both the reaction for producing the above-described ylide compound and the Wittig reaction, the reaction temperature may usually range from −25° C. to 100° C. and preferably from 0° C. to 50° C. The ylide compound may usually be used in an amount of 1 to 5 equivalents, preferably 1 to 2 equivalents, based on the oxo compound.

Furthermore, if necessary, the double bond existing in the N-substituent on the piperidine ring of the compound thus obtained may be reduced to form a saturated bond. Reduction of the double bond may generally be carried out by effecting catalytic reduction in the present of a catalyst such as a palladium-carbon catalyst, palladium hydroxide, a Raney nickel catalyst or a platinum oxide catalyst, in an inert solvent (e.g., methanol, ethanol, water or acetic acid) or a mixture of such solvents, preferably under a pressure of hydrogen of about 1 to about 20 kg/cm², preferably at a temperature in the range of about 0° to about 40° C., for a period of time ranging from 10 minutes to 24 hours.

In the process variant (b), the condensation reaction of a carboxylic acid of formula [III] or a reactive derivative thereof with a piperidine derivative of formula [V] in its first step may be carried out in the same manner as described for the condensation reaction of a carboxylic acid of formula [III] or a reactive derivative thereof with a compound of formula [IV] in the process variant (b).

Subsequently, the protective group for the imino group is removed from the compound of the above formula [VI] obtained as result of this condensation reaction.

Removal of the protective group for the imino group from the compound of formula [VI] can be carried out according to any of various conventionally known methods including, for example, the method of T. W. Greene (which is described in "Protective Groups in Organic Synthesis", John Wiley & Sons, 1981) and its equivalents. More specifically, this can be accomplished, for example, by solvolysis using an acid or base, by chemical reduction using a metal hydride complex or the like, or by catalytic reduction using a palladium-carbon catalyst, a Raney nickel catalyst or the like.

Solvolysis with an acid may generally be carried out by treating the compound of formula [VI] with an acid such as formic acid, trifluoroacetic acid, hydrochloric acid or sulfuric acid, in an inert solvent (such as methylene chloride, anisole, tetrahydrofuran, dioxane, methanol or ethanol) or a mixture of such a solvent and water, or in the absence of solvent, preferably at a temperature in the range of about 0° to about 100° C., for a period of time ranging from 10 minutes to 24 hours.

Solvolysis with a base may generally be carried out by treating the compound of formula [VI] with an alkali metal hydroxide (e.g., lithium hydroxide, sodium hydroxide or potassium hydroxide), an alkali metal carbonate (e.g., sodium carbonate or potassium carbonate) or the like, in an inert solvent which exerts no adverse effect on the reaction (e.g., methanol, ethanol, isopropanol, tetrahydrofuran or dioxane) or a mixture of such a solvent and water, preferably at a temperature in the range of about −20° to about 80° C., for a period of time ranging from 10 minutes to 24 hours.

Catalytic reduction may generally be carried out by catalytically reducing the compound of formula [VI] in the present of a catalyst such as a palladium-carbon catalyst, palladium hydroxide, a Raney nickel catalyst or a platinum oxide catalyst, in an inert solvent (e.g., methanol, ethanol, water or acetic acid) or a mixture of such solvents, preferably under a pressure of hydrogen of about 1 to about 20 kg/cm², preferably at a temperature in the range of about 0° to about 40° C., for a period of time ranging from 10 minutes to 24 hours.

In a second step, the resulting compound of the general formula [XI]

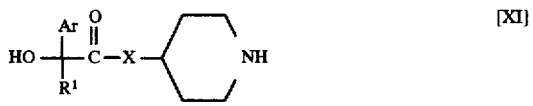

wherein Ar, R¹ and X are as defined above, is reacted with a compound of formula [VII] or [VIII], if necessary, in the presence of a base.

The reaction of the compound of formula [XI] with the compound of formula [VII] or [VIII] is usually carried out in a suitable solvent by using the compounds in substantially equimolar amounts or using either of the compounds in slight excess (e.g., using the compound of formula [VII] or [VIII] in an amount of 1 to 1.3 moles per mole of the compound of formula [XI]). If desired, however, either of the compounds may be used in large excess. Moreover, a suitable base and/or reaction additive may be used.

Suitable solvents include, for example, ethers such as diethyl ether, tetrahydrofuran and dioxane; aromatic hydrocarbons such as benzene, toluene, chlorobenzene and xylene; aprotic polar solvents such as dimethyl sulfoxide, N,N-dimethylformamide, acetonitrile and hexamethylphosphoric triamide; and mixtures thereof.

Bases which can be used for above-described reaction include, for example, alkali metal bicarbonates such as sodium hydrogen carbonate and potassium hydrogen carbonate; alkali metal carbonates such as sodium carbonate and potassium carbonate; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline. Among others, N,N-diisopropylethylamine and triethylamine are preferred.

Reaction additives which can be used for above-described reaction include, for example, alkali metal iodides such as lithium iodide, sodium iodide and potassium iodide. Among others, potassium iodide is preferred.

The reaction temperature may usually range from about 0° C. to the boiling point of the solvent, and the reaction time may usually range from 10 minutes to 48 hours. If desired, however, reaction conditions beyond these limits may be used.

Thus, when a compound of formula [VII] in which R²⁰ is a saturated or unsaturated aliphatic hydrocarbon radical of 5 to 15 carbon atoms is used as a starting material in the reaction of the above-described second step, a compound of formula [I] in accordance with the present invention is directly obtained.

On the other hand, when a compound of formula [VII] in which $R^{20}$ is an aliphatic hydrocarbon radical of 2 to 14 carbon atoms having a protected or unprotected oxo group, or a compound of formula [VIII] is used, the resulting product can be converted into a compound of formula [I] in accordance with the present invention, by subjecting it to the Wittig reaction, either directly or after removal of the protective group which may exist, and then reducing the double bond which may be present in the aliphatic hydrocarbon chain, where necessary. The above-described removal of the protective group for the oxo group, the Wittig reaction and the reduction of the double bond may be carried out in the same manner as described above in connection with the process variant (a).

The reductive alkylation reaction of a compound of the above formula [XI] with an aldehyde of formula [IX] according to the process variant (c) is generally carried out in an inert solvent which exerts no adverse effect on the reaction. Suitable solvents include, for example, alcohols such as methanol and ethanol; ethers such as diethyl ether, tetrahydrofuran and dioxane; aromatic hydrocarbons such as benzene and toluene; and mixtures thereof. Among others, methanol, ethanol, tetrahydrofuran and toluene are preferred.

The reaction temperature may usually range from about −30° C. to about 200° C. and preferably from about 0° C. to about 100° C. The reaction time may usually range from 10 minutes to 7 days and preferably from 10 minutes to 24 hours.

The above-described reductive alkylation reaction is preferably carried out under weakly acidic conditions which facilitate the formation of Schiff bases. Acids which can be used to perform the pH control therefor include, for example, p-toluenesulfonic acid, hydrochloric acid, acetic acid and trifluoroacetic acid.

The reductive alkylation can be effected, for example, by means of a metal hydride complex such as sodium borohydride, sodium cyanoborohydride or lithium aluminum hydride, or by catalytic reduction using a palladium-carbon catalyst, a Raney nickel catalyst or the like. Preferably, it is effected by means of a metal hydride complex such as sodium borohydride or sodium cyanoborohydride. Especially when the reductive alkylation reaction is carried out under weakly acidic conditions which facilitate the formation of Schiff bases, it is preferable to use sodium cyanoborohydride or the like which is relatively stable in the acid pH range.

When a metal hydride complex is used as the reducing agent, the amount of reducing agent used may usually range from 1 mole to excessive moles, preferably from 1 to 10 moles, per mole of the compound of formula [XI].

The compounds of formula [I] obtained according to the above-described process variants (a), (b) and (c) can be isolated and purified by using usual techniques. Suitable techniques include, for example, column chromatography using silica gel, adsorbent resin or the like, liquid chromatography, thin-layer chromatography, solvent extraction, recrystallization and reprecipitation.

The compounds of the present invention and intermediates thereof exist in stereoisomeric forms such as optical isomers, diastereoisomers and geometrical isomers. It is to be understood that the compounds of the present invention also include all such stereoisomerically pure substances and mixtures thereof.

When the compounds of the present invention and intermediates thereof are racemates, their optical resolution can be achieved by conventional means. For example, this can be accomplished by high-performance liquid chromatography using a chiral carrier or by fractional crystallization of a diastereomeric salt.

The compounds of formula [I] obtained in the above-described manner may be converted into pharmaceutically acceptable salts thereof according to a usual method. Conversely, such salts may also be converted into the corresponding free amines according to a usual method.

The compounds of formula [I] in accordance with the present invention have a potent and selective inhibitory effect on binding to muscarinic receptors, as well as a potent and selective antagonistic effect on muscarinic receptors both in vitro and in vivo. These effects possessed by the compounds of the present invention are demonstrated by the following tests on the inhibition of binding to muscarinic receptors and tests on antagonism against muscarinic receptors. In these tests, their inhibitory and antagonistic effects were expressed in terms of the dissociation constant ($K_i$) of each test compound which was calculated from its concentration ($IC_{50}$) causing a 50% inhibition of the binding of a labeled ligand to muscarinic receptors. As the labeled ligand, [$^3$H]-telenzepine was used for the muscarinic $M_1$ receptors and [$^3$H]-N-methylscopolamine for the muscarinic $M_2$ and $M_3$ receptors.

Tests for the Inhibition of Binding to Muscarinic Receptors
1) Preparation of membrane specimens A male SD strain rat (purchased from Nippon Charles River Co., Ltd.), weighing about 250–350 g, was sacrificed, and the cerebral cortex, heart and lacrimal glands were excised. Using a Polytron (setting 5), each organ was homogenized in 5 volumes of an ice-cold buffer solution (pH 7.4) containing 50 mM tris-HCl, 5 mM magnesium chloride, 1 mM trisodium ethylenediaminetetraacetate and 20% sucrose. The resulting homogenate was centrifuged at 3,000×g at 4° C. for 15 minutes, and the supernatant was filtered through gauze and ultracentrifuged at 100,000×g at 4° C. for 45 minutes. The resulting precipitate was suspended in an ice-cold buffer solution (pH 7.4) containing 50 mM tris-HCl and 5 mM magnesium chloride (hereinafter referred briefly to as "tris buffer") and ultracentrifuged at 100,000×g at 4° C. for 45 minutes. The resulting precipitate was suspended in tris buffer so as to give a concentration of 50 mg/ml and stored at −80° C. till use. The membrane specimens so prepared were thawed prior to use and submitted to tests for the inhibition of binding to muscarinic receptors.

2) Tests for the inhibition of binding to the muscarinic $M_1$ receptors

These tests were performed according to a modification of the method of Hargreaves et al. [Br. J. Pharmacol., Vol. 107, pp. 494–501 (1992)]. Specifically, a mixture of a membrane specimen from the cerebral cortex, 1 nM [$^3$H]-telenzepine (85 Ci/mmol; manufactured by New England Nuclear) and a test compound in 0.5 ml of tris buffer was incubated at room temperature (about 20°–25° C.) for 120 minutes. After the addition of 0.5 ml of ice-cold tris buffer, the mixture was filtered by suction through a glass filter (Packard Unifilter Plate GF/C). Then, the filter was washed four times with 1 ml portions of ice-cold tris buffer and dried at 50° C. for an hour. After the addition of a scintillator (Packard Microscinti 0), the radioactivity of [$^3$H]-telenzepine adsorbed to the filter was measured with a microplate scintillation counter (Packard Topcount). The nonspecific binding of [$^3$H]-telenzepine to receptors was determined by the addition of 10 mM pirenzepine. According to the method of Cheng and Prusoff [Biochem. Pharmacol., Vol. 22, pp. 3099–3108 (1973)], the affinity of the test compound (i.e., a compound in accordance with the present invention) for the muscarinic $M_1$ receptors was determined in terms of its dissociation constant ($K_i$) calculated from the concentration ($IC_{50}$) of the test compound which was required to cause a 50% inhibition of the binding of [$^3$H]-telenzepine used as the labeled ligand.
3) Tests for the inhibition of binding to the muscarinic $M_2$ receptors These tests were performed in the same manner as described above in "2) Tests for the inhibition of binding to the muscarinic $M_1$ receptors", except that a membrane specimen from the heart was used as the membrane specimen and 0.2 nM [$^3$H]-N-methylscopolamine (84 Ci/mmol; manufactured by New England Nuclear) as the labeled ligand. The nonspecific binding of [$^3$H]-N-methylscopolamine to receptors was determined by the addition of 1 mM N-methylscopolamine.

4) Tests for the inhibition of binding to the muscarinic $M_2$ receptors

These tests were performed in the same manner as described above in "2) Tests for the inhibition of binding to the muscarinic $M_1$ receptors", except that a membrane specimen from the lacrimal glands was used as the membrane specimen and 0.2 nM [$^3$H]-N-methylscopolamine as the labeled ligand. The nonspecific binding of [$^3$H]-N-methylscopolamine to receptors was determined by the addition of 1 mM N-methylscopolamine.

TABLE 1

Inhibitory Effects on Binding to the Muscarinic $M_1$, $M_2$ and $M_3$ Receptors

| | $K_i$ (nM) | | | | |
|---|---|---|---|---|---|
| | $M_1$ | $M_2$ | $M_3$ | $M_1/M_3$ | $M_2/M_3$ |
| Compound of Example 1 | 45 | 860 | 8.9 | 5.0 | 96 |
| Compound of Example 16 | 13 | 302 | 3.1 | 4.2 | 97 |
| Compound of Example 22 | 120 | 1400 | 9.2 | 13.0 | 152 |
| Compound of Example 28 | 6.0 | 190 | 2.0 | 3.0 | 96 |
| Compound of Example 29 | 40 | 1100 | 4.1 | 10 | 270 |
| Compound of Example 32 | 84 | 2300 | 11 | 7.9 | 220 |

As is evident from the results shown in Table 1 above, the compounds of the present invention antagonized the muscarinic $M_3$ receptors more strongly than the muscarinic $M_1$ and $M_2$ receptors.

Tests for Antagonism against Muscarinic $M_1$ Receptors (in vitro)

1) Tests for antagonism against the $M_1$ receptors in an isolated rabbit vas deferens These tests were performed according to an ordinary method. A male Japanese albino rabbit (weighing bout 3 kg) was killed by exsanguination from a femoral artery under anesthesia with pentobarbital, and the vasa deferentia were excised. Portions (1 cm long) thereof adjacent to the prostate were used as vas deferens preparations. A preparation was longitudinally suspended in a Magnus tube filled with 20 ml of Krebs-Henseleit nutrient solution [gassed with 95% $O_2$–5% $CO_2$ and kept at 32° C. ; containing 1 mM yohimbine ($a_2$ antagonist)] with an initial tension of 1.0 g. The tension of the preparation was recorded isometrically. After the preparation was equilibrated for 30 minutes, electrical stimuli (0.5 ms, 30 V) were applied thereto by means of a bipolar electrode to induce contractions at intervals of 20 seconds. After contractions induced by the electrical stimulation were stabilized, an inhibition of contractions in response to McN A-343 ($2.5 \times 10^{-6}$M, selective $M_1$ agonist) was observed three times (adaptive response). After the preparation was washed with fresh solution to resume contractions, McN A-343 ($10^{-7}$ to $10^{-5}$M) was cumulatively administered from the lowermost concentration in three-fold increasing doses until a maximum response was achieved. Thus, there was obtained a dose-response curve for the control experiment. After the preparation was washed with fresh solution to resume contractions, it was treated with a test compound. Ten minutes later, McN A-343 was cumulatively administered again. Responses to McN A-343 were expressed as percentages based on the amount of contraction before administration of McN A-343. The antagonistic potency ($K_B$ value) of the test compound was determined from the degree of shift of the dose-response curve obtained by treatment with the test compound.

2) Tests for antagonism against the $M_2$ receptors in an isolated rat right atrium These tests were performed according to an ordinary method. A male SD strain rat (weighing 300–500 g) was killed by exsanguination, and the right atrium was excised. This preparation was isometrically suspended in a Magnus tube filled with 20 ml of Krebs-Henseleit nutrient solution (gassed with 95% $O_2$–5% $CO_2$ and kept at 32° C.) with an initial tension of 0.5 g. The heart rate was recorded with a heart rate counter. After the preparation was equilibrated for 30 minutes, carbachol ($10^{-9}$ to $10^{-6}$M) was cumulatively administered from the lowermost concentration in three-fold increasing doses. Thus, a decrease in heart rate was measured to obtain a dose-response curve for the control experiment. After the preparation was washed with fresh solution to restore the heart rate, a test compound was administered thereto. Ten minutes later, carbachol was cumulatively administered again. Responses to carbachol were expressed as percentages based on the heart rate before administration of carbachol. The antagonistic potency ($K_B$ value) of the test compound (i.e., a compound in accordance with the present invention) was determined from the degree of shift of the dose-response curve obtained by treatment with the test compound.

3) Tests for antagonism against the airway $M_3$ receptors in an isolated rat trachea These tests were performed according to an ordinary method. A male SD strain rat (weighing 300–500 g) was killed by exsanguination, and the trachea was excised. Annular segments (2 mm wide) were cut out from the trachea and cut open at the anterior cartilage part to make transversely sectioned trachea preparations. A preparation was suspended in a Magnus tube filled with 5 ml of Krebs-Henseleit nutrient solution (gassed with 95% $O_2$–5% $CO_2$ and kept at 32° C.) with an initial tension of 1.0 g and a resting tension of 0.6 g. The tension of the preparation was recorded isometrically. After being equilibrated for an hour, the preparation was made to contract twice by treatment with $10^{-4}$M carbachol, and the second contraction induced by carbachol was used as the reference contraction. After the preparation was washed with fresh solution to make a return to the base line, a test compound was administered thereto (or no treatment was made). Ten minutes later, carbachol ($10^{-8}$ to $10^{-3}$M) was cumulatively administered in three-fold increasing doses to obtain a dose-response curve. The dose-response curve was constructed by expressing responses as percentages based on the reference contraction of the preparation. The antagonistic potency ($K_B$ value) of the test compound (i.e., a compound in accordance with the present invention) was determined from the degree of shift of the dose-response curve obtained by treatment with the test compound.

4) Tests for antagonism against the intestinal $M_3$ receptors in an isolated rat ileum A male SD strain rat (weighing 300–500 g) was killed by exsanguination, and the ileum was excised. This ileum was cut to make ileum preparations having a length of 2 cm. A preparation was suspended in a Magnus tube filled with 20 ml of Krebs-Henseleit nutrient solution (gassed with 95% $O_2$–5% $CO_2$ and kept at 32° C.) under a load of 0.5 g. The tension of the preparation was recorded isotonically. After being equilibrated for an hour, the preparation was made to contract twice by treatment with $10^{-4}$M carbachol, and the second contraction induced by carbachol was used as the reference contraction. After the preparation was washed with fresh solution to make a return to the base line, a test compound was administered thereto (or no treatment was made). Ten minutes later, carbachol ($10^{-8}$ to $10^{-3}$M) was cumulatively administered from the lowermost concentration in three-fold increasing doses to obtain a dose-response curve. The dose-response curve was constructed by expressing responses as percentages based on the reference contraction of the preparation. The antagonistic potency ($K_B$ value) of the test compound was determined from the degree of shift of the dose-response curve obtained by treatment with the test compound.

5) Tests for antagonism against the bladder $M_3$ receptors in an isolated rat bladder These tests were performed according to an ordinary method. A male SD strain rat (weighing 200–400 g) was killed by exsanguination, and the bladder was excised. This bladder axially cut into eight parts to make bladder preparations. A preparation was suspended in a Magnus tube filled with 5 ml of Krebs-Henseleit nutrient solution (gassed with 95% $O_2$–5% $CO_2$ and kept at 32° C.) with an initial tension of 0.5 g. The tension of the preparation was recorded isometrically. After being equilibrated for an hour, the preparation was made to contract twice by treatment with $10^{-4}$M carbachol, and the second contraction induced by carbachol was used as the reference contraction. After the preparation was washed with fresh solution to make a return to the base line, a test compound was administered thereto (or no treatment was made). Ten minutes later, carbachol ($10^{-8}$ to $10^{-3}$M) was cumulatively administered from the lower-most concentration in three-fold increasing doses to obtain a dose-response curve. The dose-response curve was constructed by expressing responses as percentages based on the reference contraction of the preparation. The antagonistic potency ($K_B$ value) of the test compound was determined from the degree of shift of the dose-response curve obtained by treatment with the test compound.

Its action was more selective to the trachea, ileum and bladder $M_3$ receptors, and particularly strong antagonism against the trachea $M_3$ receptors was observed. That is, the compound of the present invention is a compound which is more selective to the trachea $M_3$ receptors.

Tests for antagonism against muscarinic $M_3$ receptor (in vivo)

1) Tests for bronchodilation in rats

Eight- to eleven-weeks-old male rats of the Sprague-Dawley strain, weighing 300–400 g, were anesthetized with urethane (750 mg/kg, i.p.) and a-chloralose (37.5 mg/kg, i.p.). A bronchus was intubated, and the right jugular vein was cannulated for drug administration. After spontaneous respiration was fully suppressed by succinylcholine (5 mg/kg, s.c.), the airway resistance was measured under artificial ventilation by means of a Pulmonary Mechanics Model 6 (Buxco). To evoke an increase in airway resistance, acetylcholine (50 µg/kg, i.v.) was administered to the animals. Mean values for the acetylcholine-induced increase in airway resistance as measured five minutes before (control) and five minutes after test compound administration were calculated and the results were expressed as percentages of the control response. The $ID_{50}$ value was calculated from the dose-response curve of the test compound using probit analysis and defined as the drug dose that inhibited the acetylcholine-induced increase in airway resistance in the control group by 50 %.

2) Tests for salivary secretion in rats

Five- to seven-weeks-old male rats of the Sprague-Dawley strain were anesthetized with sodium pentobarbital (65 mg/kg, i.p.), and a cannula was inserted into the right jugular vein for purposes of drug administration. A test compound was administered intravenously. Five minutes later, carbachol (10 µg/kg, i.v.) was administered to evoke salivary secretion. For each rat, saliva collection was started immediately after carbachol administration and continued for ten minutes. This was carried out by inserting glass capillaries (Drummond, 100 µl) into the oral cavity of the rat at intervals of one minute. The amount of collected saliva was determined on the assumption that a length of 75 mm of the glass capillary corresponded to 100 µl. Physiological saline was used in the control group. The $ID_{50}$ value was calculated from the dose-response curve of the test compound using probit analysis and defined as the drug dose that inhibited the carbachol-induced salivation in the control group by 50%.

3) Tests for mydriasis in rats

Five- to seven-weeks-old male rats of the Sprague-Dawley strain were anesthetized with pentobarbital (65

TABLE 2

| | Antagonistic Effects on Muscarinic Receptors (in vitro) | | | | | | |
|---|---|---|---|---|---|---|---|
| | $K_B$ (nM) | | | | | | |
| | Vas deferens $M_1$ | Right atrium $M_2$ | Trachea $M_3$ | Ileum $M_3$ | Bladder $M_3$ | $M_1/M_3$* | $M_2/M_3$* |
| Compound of Example 1 | 120 | 1500 | 19 | 24 | 31 | 6.3 | 79 |

*Trachea $M_3$

As is evident from the result shown in Table 2 above, the compound of the present invention antagonized various muscarinic receptors including the vas deferens $M_1$, right atrium $M_2$, trachea $M_3$, ileum $M_3$ and bladder $M_3$ receptors.

mg/kg, i.p.), and a cannula was inserted into the right jugular vein for purposes of drug administration. By using a graduated scale (pulilometer), pupillary responses to drugs were measured to the nearest 0.1 mm at the point of the greatest diameter. After a test compound was administered intravenously, the change in pupil diameter relative to the value observed before administration of the test compound was measured. Responses were expressed as percentages of the maximal increase in pupil diameter induced by administration of atropine (30 μg/kg, i.v.). The $ED_{50}$ value was calculated from the dose-response curve of the test compound using probit analysis and defined as the drug dose that induced 50% of the maximal response.

4) Tests for intravesical bladder pressure in rats

These tests were performed according to the method of Maggi et al. (Drug Dev. Res. 10: 157–170, 1987). Briefly, eight- to ten-weeks-old male rats of the Sprague-Dawley strain, weighing 330–370 g, were anesthetized by subcutaneous administration of urethane (1 g/kg) and α-chloralose (50 mg/kg), and the right jugular vein was cannulated for drug administration. The body temperature was kept constant by means of a heating pad maintained at 37° C. Through a midline incision of the abdomen, the urinary bladder was exposed and emptied of urine by the application of a slight manual pressure. A 20-gauge needle was inserted through the apex of the bladder dome by 3–4 mm into its lumen. The needle had previously been connected to a pressure transducer and an infusion pump by means of polyethylene tubing and the whole system filled with saline. After a 30-minutes equilibration period at zero volume, saline was infused (2.8 ml/hr) until a coordinated sustained contraction, reflecting the peak intravesical bladder pressure, occured. The bladder was then emptied manually and allowed to rest for five minutes. PvesP was defined as the difference between the maximum and resting bladder pressures. This procedure was repeated at least five times and the evaluation of a test compound was carried out in the animals in which a stable peak intravesical bladder pressure was recorded. The drug potency ($ID_{25}$) was determined after intravenous administration of the test compound during the rest period. Five minutes after drug administration, the infusion of saline was started to induce micturition contraction and the peak intravesical bladder pressure was recorded. The depression in peak intravesical bladder pressure was expressed as a percent of the control peak intravesical bladder pressure observed before administration of the test compound. The $ID_{25}$ value, calculated by probit analysis, was defined as the drug dose that inhibited the control peak intravesical bladder pressure by 25%.

5) Tests for intestinal propulsion in rats

Five- to seven-weeks-old male rats of the Sprague-Dawley strain were fasted overnight. A test compound was administered intravenously to the animals. Five minutes later, 1 ml per animal of a 5% charcoal suspension was administered orally. Thirty minutes after administration of the charcoal meal, the rats were sacrificed by decapitation, and the gastrointestinal tract was removed. The distance from the pylorus to the point of arrival of the charcoal meal was measured and the transportation rate was calculated. The $ID_{15}$ value was calculated from the dose-response curve using probit analysis and defined as the drug dose that inhibited intestinal propulsion in the control group by 15%.

6) Tests for bradycardia in rats

Eight- to eleven-weeks-old male rats of the Sprague-Dawley strain, weighing 300–400 g, were anesthetized with urethane (750 mg/kg, i.p.) and α-chloralose (37.5 mg/kg, i.p.). A bronchus was intubated, and the right jugular vein was cannulated for drug administration. After spontaneous respiration was fully suppressed by succinylcholine (5 mg/kg, s.c.), the heart rate was measured under artificial ventilation. To evoke bradycardia, acetylcholine (50 μg/kg, i.v.) was administered to the animals. Mean values for the acetylcholine-induced decrease in heart rate as measured five minutes before (control) and five minutes after test compound administration were calculated and the results were expressed as percentages relative to the control response. The $ID_{50}$ value was calculated from the dose-response curve of the test compound using probit analysis and defined as the drug dose that inhibited the acetylcholine-induced bradycardia in the control group by 50%.

TABLE 3

| | Antagonistic Effects on Muscarinic Receptors (in vivo) | | | | | |
|---|---|---|---|---|---|---|
| | Airway contraction $ID_{50}$ (mg/kg i.v.) | Salivary secretion $ID_{50}$ (mg/kg i.v.) | Mydriasis $ED_{50}$ (mg/kg i.v.) | Urinating contraction $ID_{25}$ (mg/kg i.v.) | Enterokinesis $ID_{15}$ (mg/kg i.v.) | Bradycardia $ID_{50}$ (mg/kg i.v.) |
| Compound of Example 1 | 0.023 | 0.19 | 1.4 | 1.3 | 0.67 | >3 |
| Atropine | 0.0043 | 0.0022 | 0.018 | 0.027 | 0.019 | 0.0037 |
| Ipratropium | 0.0015 | 0.0018 | 0.0041 | 0.0048 | 0.004 | 0.0018 |

As is evident from the results shown in Table 3 above, the compound of the present invention exhibited a potent bronchodilatory action and was bronchoselective over other tissues in which the muscarinic receptors associated with the side effects (e.g., thirst, mydriasis, gastrointestinal disorders, urination disorders and bradycardia) possessed by conventional anticholinergic agents are present. In particular, the compound of the present invention exhibited less activity against bradycardic response in which the muscarinic $M_2$ receptors are involved. In contrast, the control compounds (i.e., atropine and ipratropium) exhibited potent activities with respect to all of the six types of responses studied herein and their action was non-selective.

As described above, the compounds of formula [I] in accordance with the present invention are very potent and highly $M_3$ selective antagonists and can be used as safe drugs with a minimum of side effects. In particular, they may be orally or parenterally administered to patients for the treatment or prophylaxis of diseases of the respiratory system, such as asthma, chronic airway obstruction and fibroid lung; diseases of the urinary system accompanied by urination disorders such as pollakiuria, urinary urgency and urinary incontinence; and diseases of the digestive system, such as irritable colon and spasm or hyperanakinesis of the digestive tract.

More specifically, in spite of their powerful bronchodilatory activity, the compounds of the present invention exert no influence on other organs such as the brain and the heart. Accordingly, they are useful as therapeutic or prophylactic agents (e.g., bronchodilators) for various diseases of the respiratory system.

In practically using the compounds of the present invention for the treatment or prophylaxis of such diseases, they may be combined with pharmaceutically acceptable adjuvants in the usual manner to prepare pharmaceutical compositions suitable for administration. For this purpose, there can be used a variety of adjuvants which are commonly used in the field of pharmaceutics. Such adjuvants include, for example, gelatin, lactose, sucrose, titanium oxide, starch, crystalline cellulose, hydroxypropylmethylcellulose, carboxymethylcellulose, corn starch, microcrystalline wax, white soft paraffin, magnesium aluminate metasilicate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinyl pyrrolidone, magnesium stearate, light anhydrous silicic acid, talc, vegetable oil, benzyl alcohol, acacia, propylene glycol, polyalkylene glycols, cyclodextrin and hydroxypropyl cyclodextrin.

The dosage forms of pharmaceutical compositions prepared by using these adjuvants include solid preparations such as tablets, capsules, granules, powders and suppositories; liquid preparations such as syrups, elixirs and injections; and the like. These preparations may be made according to common techniques well-known in the field of pharmaceutics. Liquid preparations may be in a form which is dissolved or suspended in water or other suitable medium prior to use. In particular, injections may be in the form of a solution or suspension in physiological saline or a glucose solution, or in powder form for reconstitution by dissolution or suspension in physiological saline or a glucose solution prior to use. If desired, such injections may contain buffer agents and/or preservatives.

In these pharmaceutical compositions, a compound in accordance with the present invention may be present in an amount of 1.0 to 100% by weight, preferably 1.0 to 60% by weight, based on the total weight of the composition. These pharmaceutical compositions may additionally contain other therapeutically effective compounds.

When the compounds of the present invention are used as bronchodilators, their dosage level and dosage schedule may vary according to the sex, age and body weight of the patient, the severity of symptoms, the type and range of the desired therapeutic effect, and the like. Generally, for oral administration, they are preferably administered in a daily dose of 0.1 to 100 mg/kg for adults and this daily dose may be given at a time or in several divided doses. For parenteral administration, they are preferably administered in a daily dose of 0.001 to 10 mg/kg for adults and this daily dose may be given at a time or in several divided doses.

Structures of the compounds of Examples

| Example No. | Structure |
|---|---|
| 1 | 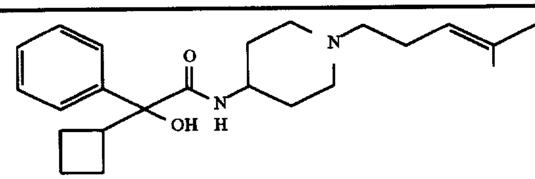 |
| 2 | 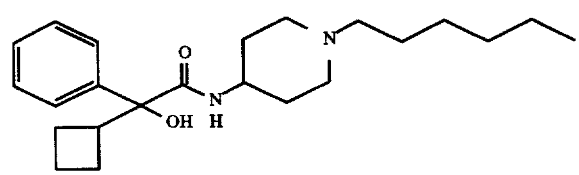 |
| 3 | 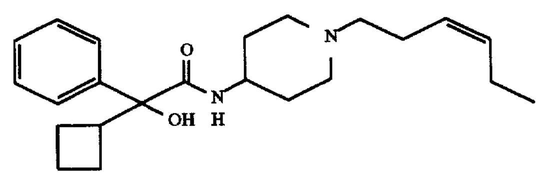 |
| 4 | 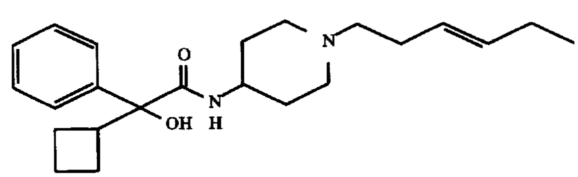 |
| 5 | 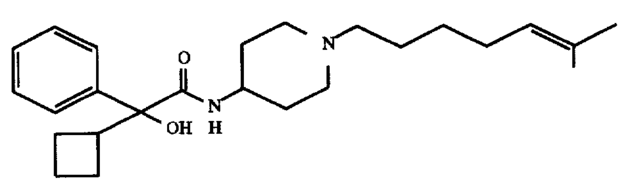 |

-continued
Structures of the compounds of Examples
| Example No. | Structure |
|---|---|
| 6 | 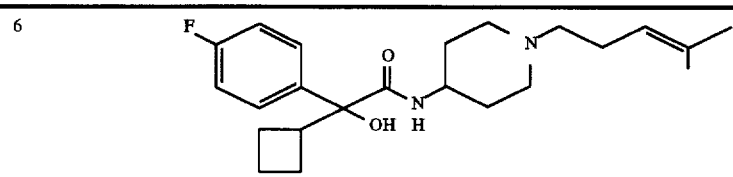 |
| 7 | 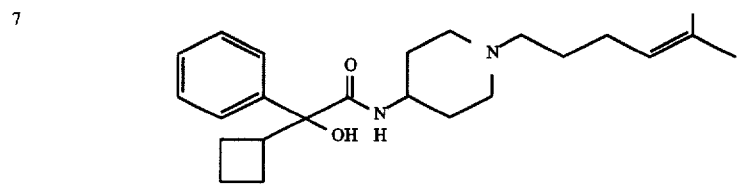 |
| 8 | 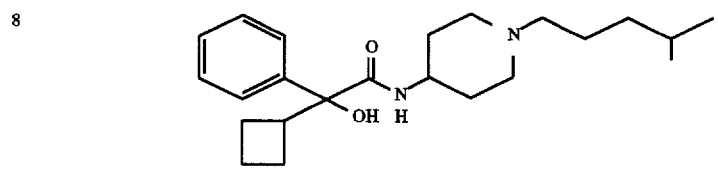 |
| 9 | 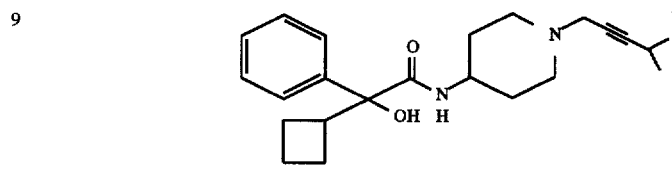 |
| 10 | 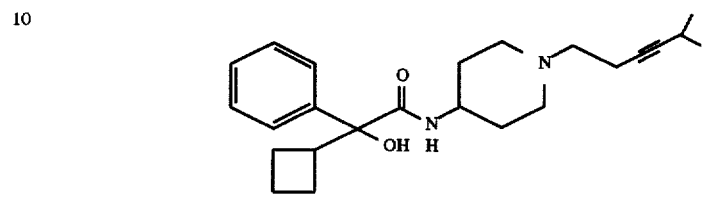 |
| 11 | 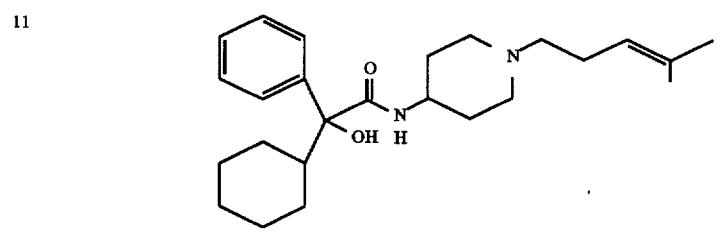 |
| 12 | 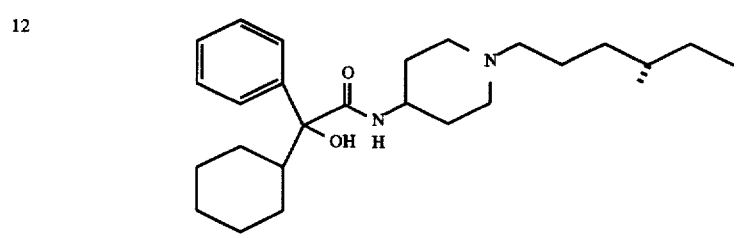 |
| 13 | 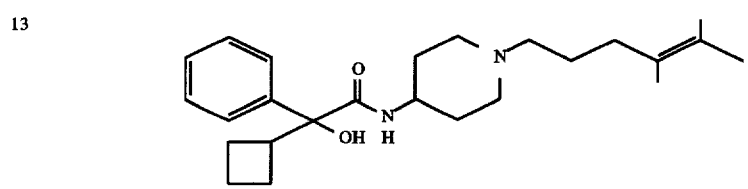 |

-continued
Structures of the compounds of Examples
| Example No. | Structure |
|---|---|
| 14 | 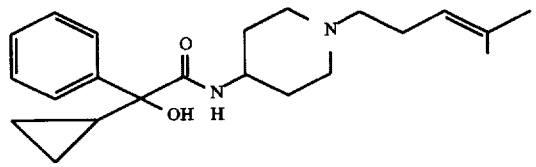 |
| 15 | 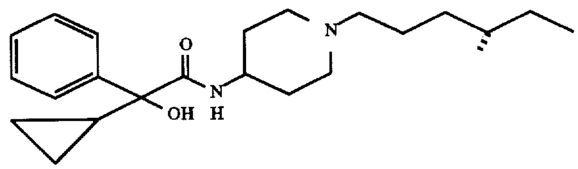 |
| 16 | 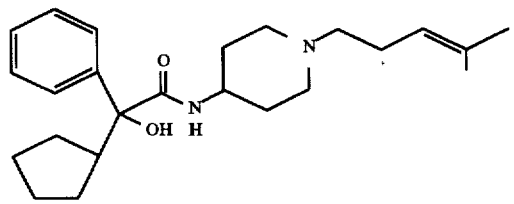 |
| 17 | 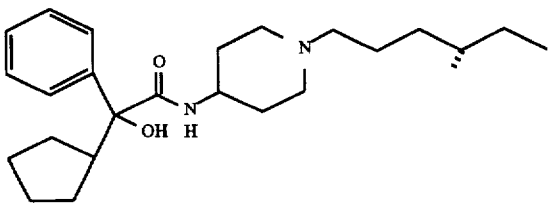 |
| 18 | 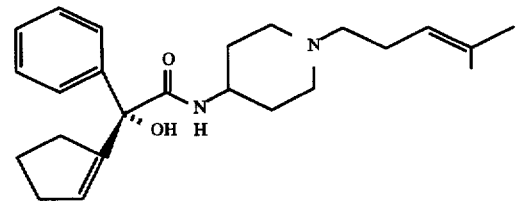 |
| 19 | 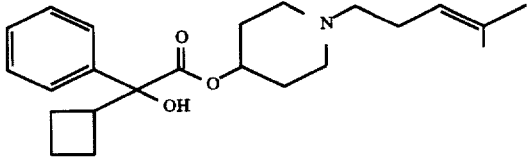 |
| 20 | 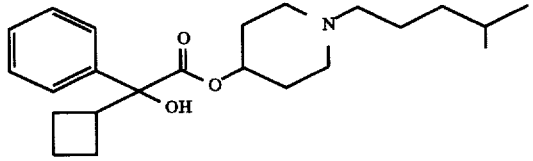 |
| 21 | 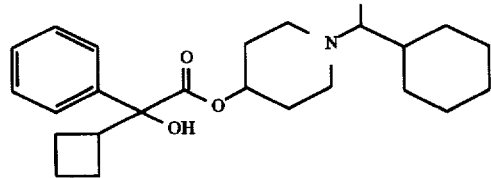 |

-continued
Structures of the compounds of Examples
| Example No. | Structure |
|---|---|
| 22 | 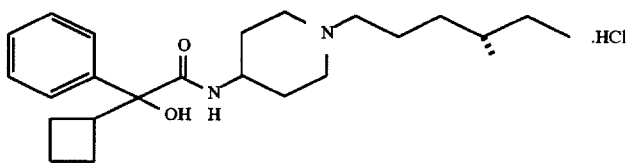 |
| 23 | 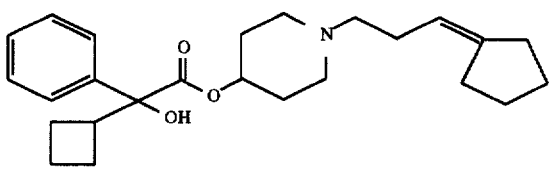 |
| 24 | 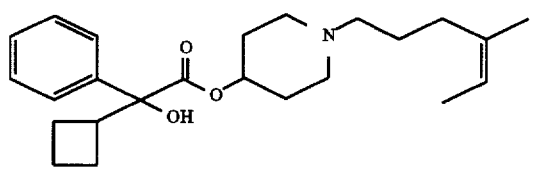 |
| 24 | 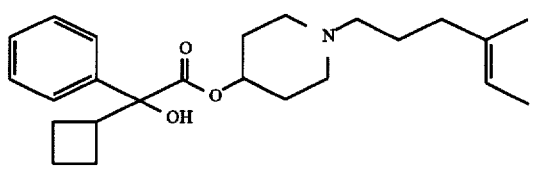 |
| 25 | 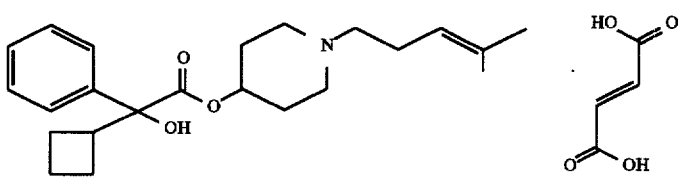 |
| 26 | 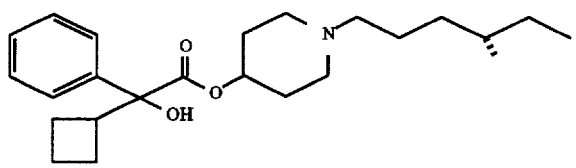 |
| 27 | 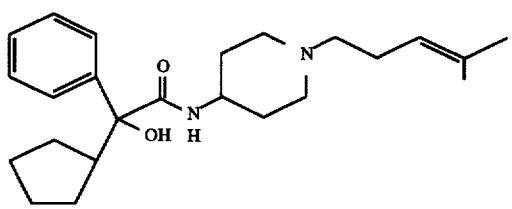 |
| 28 | 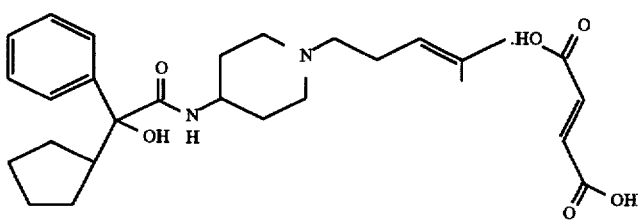 |

-continued
Structures of the compounds of Examples
| Example No. | Structure |
|---|---|
| 29 | 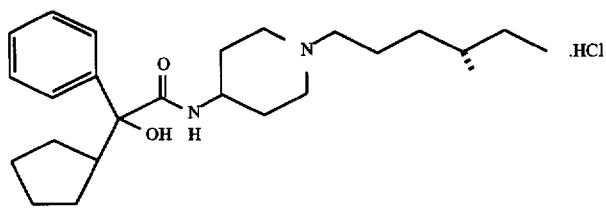 |
| 30 | 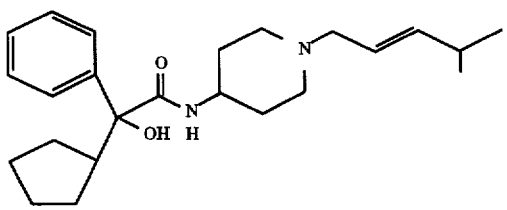 |
| 31 | 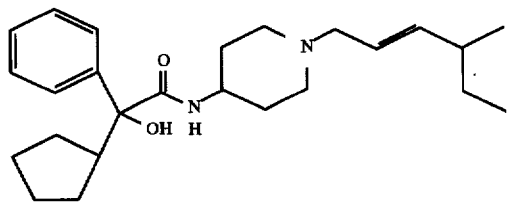 |
| 32 | 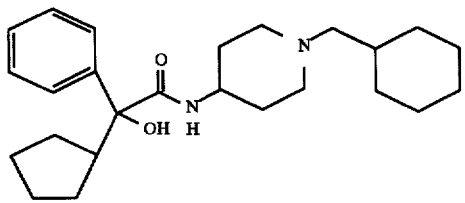 |
| 33 | 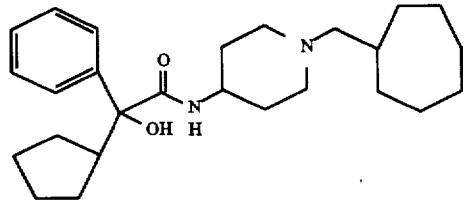 |
| 34 | 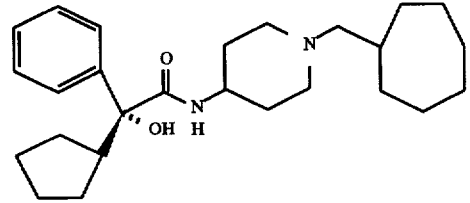 |
| 35 | 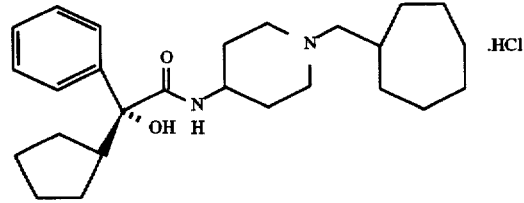 |

-continued
Structures of the compounds of Examples
| Example No. | Structure |
|---|---|
| 36 | 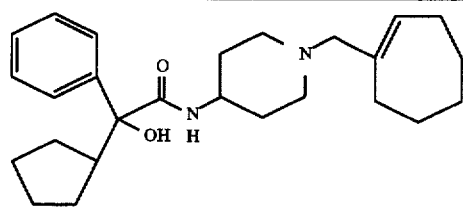 |
| 37 | 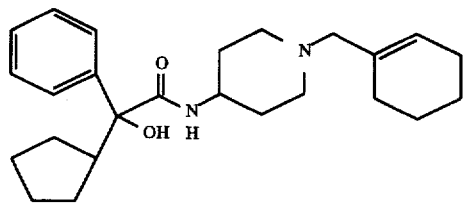 |
| 38 | 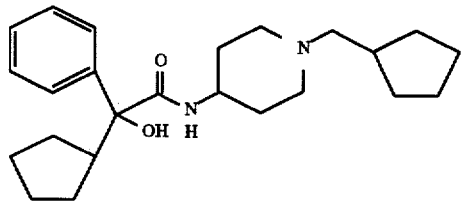 |
| 39 | 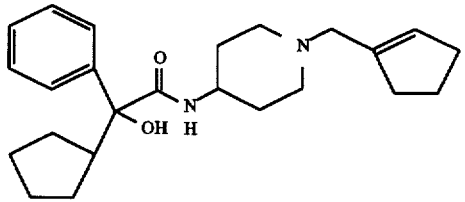 |
| 40 | 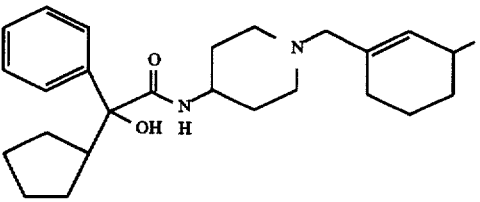 |
| 41 | 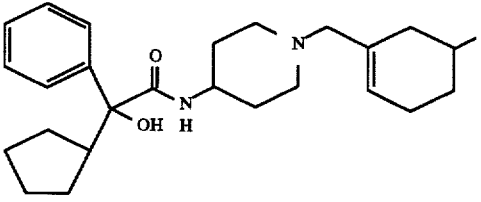 |
| 42 | 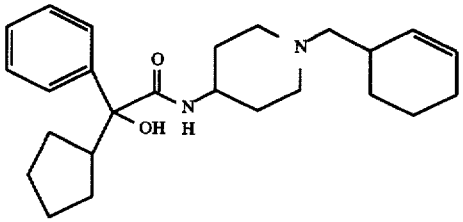 |

-continued
Structures of the compounds of Examples
| Example No. | Structure |
|---|---|
| 43 | 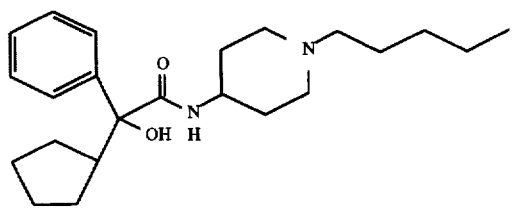 |
| 44 | 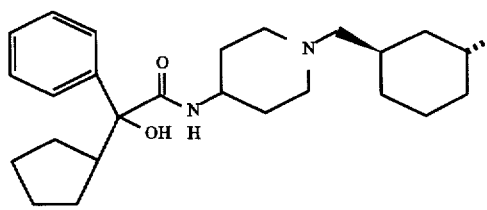 |
| 45 | 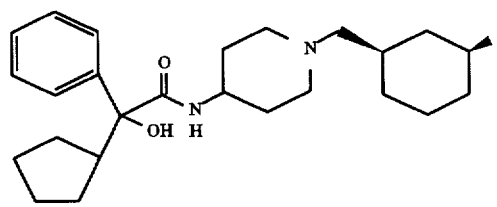 |
| 46 | 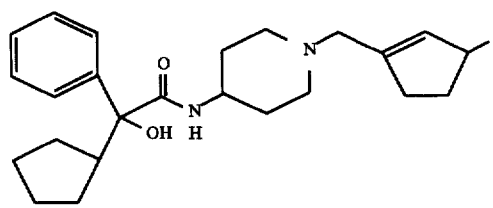 |
| 47 | 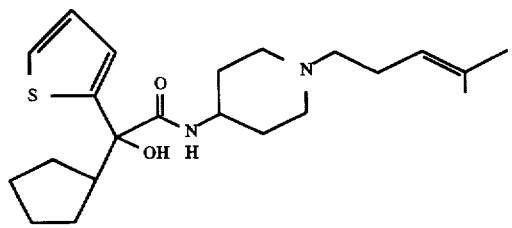 |
| 48 | 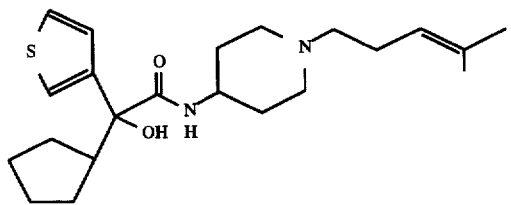 |
| 49 | 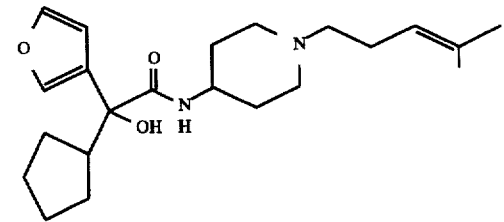 |

-continued

Structures of the compounds of Examples

| Example No. | Structure |
|---|---|
| 50 | 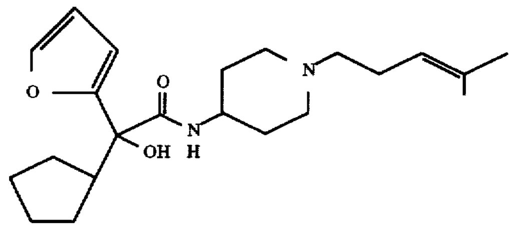 |
| 51 | 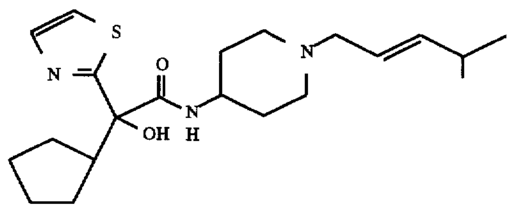 |
| 52 | 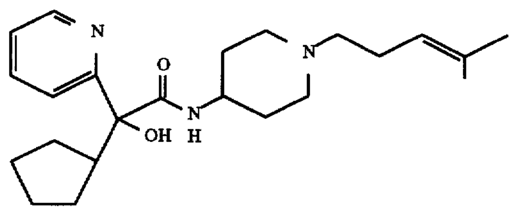 |
| 53 | 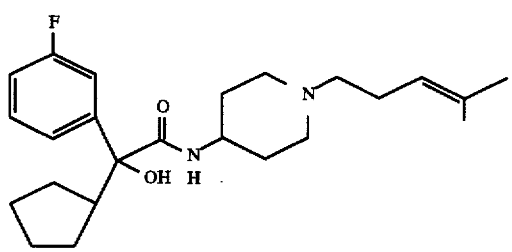 |
| 54 | 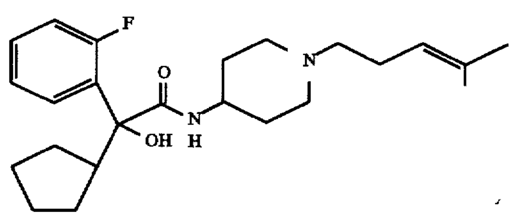 |
| 55 | 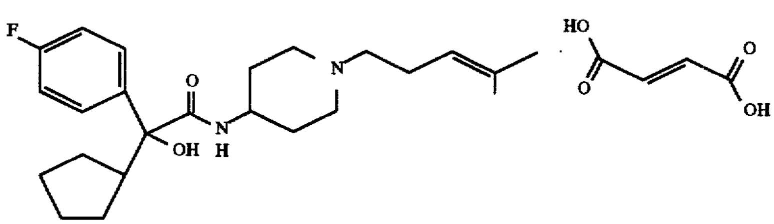 |
| 56 | 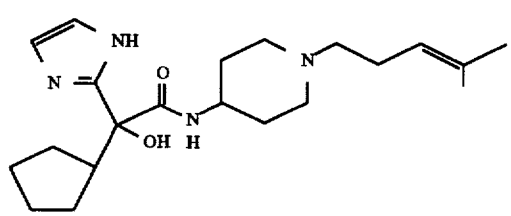 |

-continued
Structures of the compounds of Examples
| Example No. | Structure |
|---|---|
| 57 | 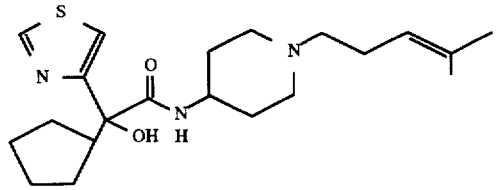 |
| 58 | 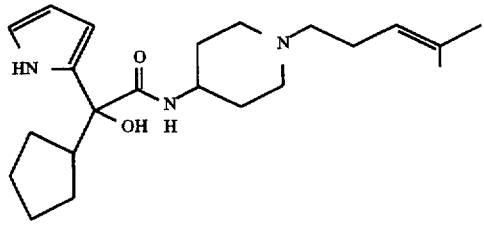 |
| 59 | 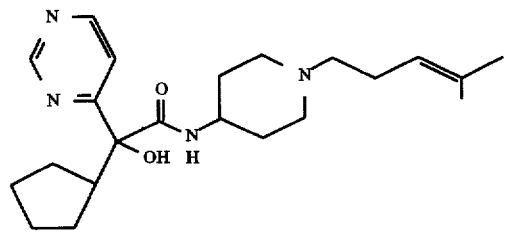 |
| 60 | 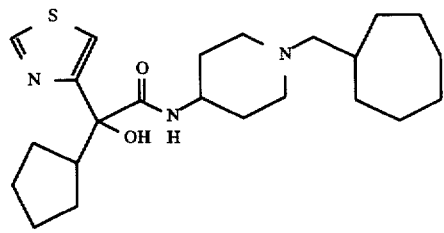 |
| 61 | 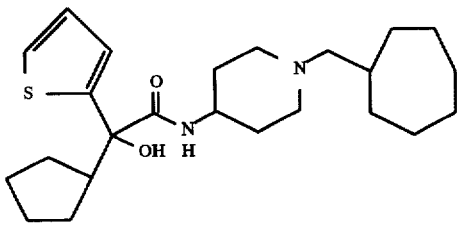 |
| 62 | 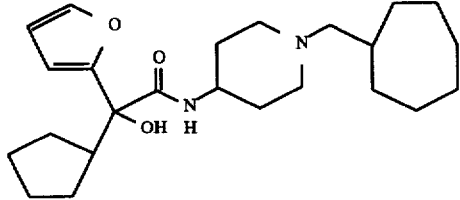 |
| 63 | 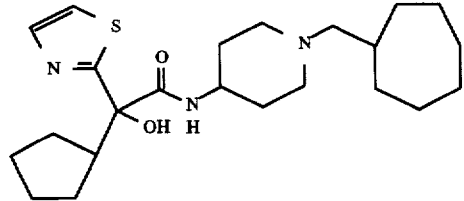 |

-continued
Structures of the compounds of Examples
| Example No. | Structure |
|---|---|
| 64 | 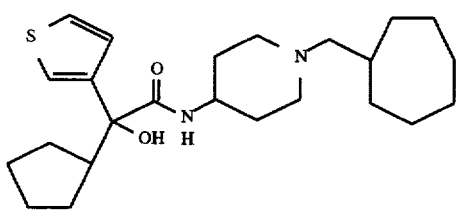 |
| 65 | 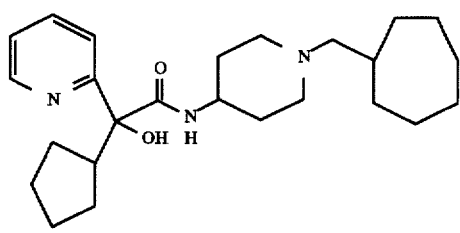 |
| 66 | 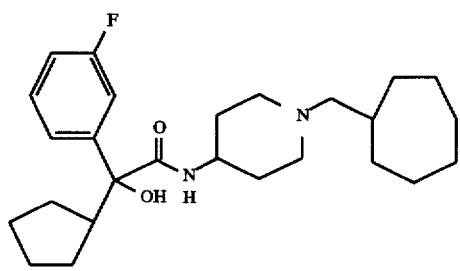 |
| 67 | 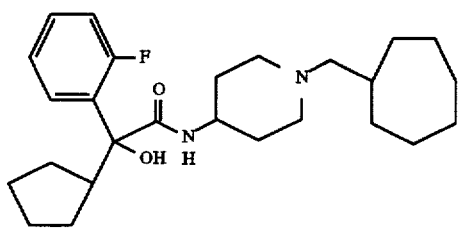 |
| 68 | 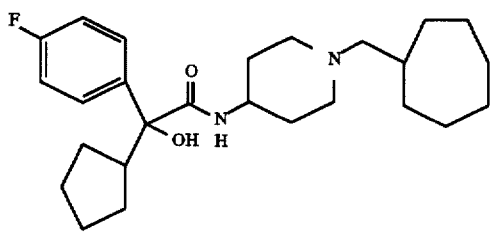 |
| 69 | 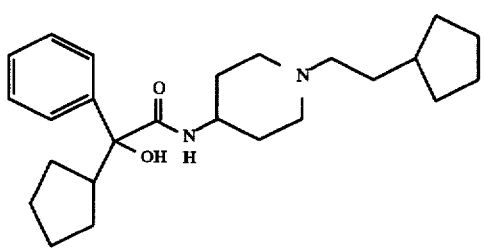 |

-continued
Structures of the compounds of Examples

| Example No. | Structure |
|---|---|
| 70 | 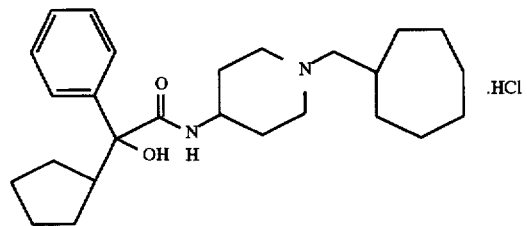 |
| 71 | 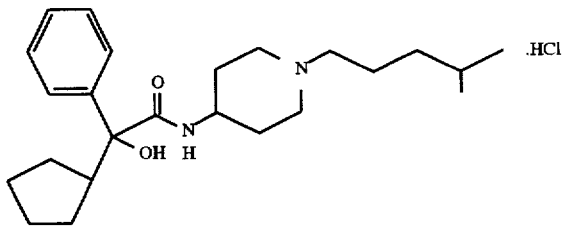 |
| 72 | 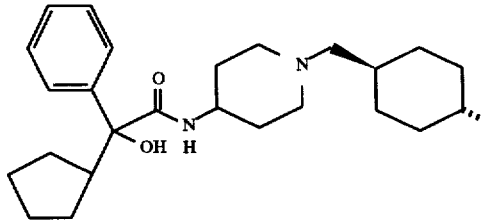 |
| 73 | 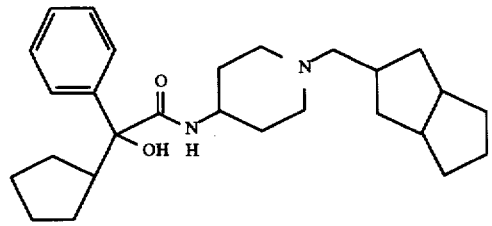 |
| 74 | 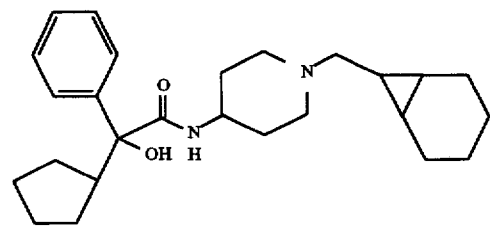 |

EXAMPLES

The present invention is more specifically explained with the following examples. However, these examples are not to be construed to limit the scope of the present invention.

Example 1

Synthesis of N-[1-(4-methyl-3-pentenyl)-piperidin-4-yl]-2-cyclobutyl-2-hydroxy-2-phenylacetamide Step 1. Synthesis of 2-cyclobutyl-2-hydroxy-2-phenylacetic acid This compound was synthesized according to the method of S. B. Kadin et al. [J. Org. Chem., Vol. 27, pp. 240–245 (1962)].

A solution of 6.24 9 of cyclobutyl phenyl ketone in 15 ml of dimethyl sulfoxide was added to a solution of 4.23 g of lithium acetylide-ethylene diamine complex in 50 ml of dimethyl sulfoxide at room temperature, and this mixture was stirred at room temperature for 4 hours. The reaction mixture was poured into ice water and extracted with diethyl ether. The organic layer was washed with water and a saturated aqueous solution of sodium chloride and then dried over anhydrous magnesium sulfate. After the solvent was distilled off under reduced pressure, the resulting residue was purified by silica gel column chromatography (developing solvent: hexane/ethyl acetate=20/1 to 9/1) to obtain 6.19 g of 1-cyclobutyl-1-phenyl-2-propyn-1-ol.

To a stirred solution of 6.19 g of the 1-cyclobutyl-1-phenyl-2-propyn-1-ol thus obtained in 20 ml of water was added a solution of 15.04 g of potassium permanganate in 250 ml of water at a temperature of 0° to 5° C., followed by vigorous stirring for 2 hours. The precipitate formed by the addition of an aqueous sodium sulfite solution at room temperature was removed by filtration through celite, and the resulting filtrate was extracted with diethyl ether. The organic layer was washed with a saturated aqueous solution of sodium chloride and then dried over anhydrous magnesium sulfate. After the solvent was distilled off under reduced pressure, the resulting residue was recrystallized (from ethyl acetate/hexane) to obtain 1.4 g of the title compound.

Step 2. Synthesis of N-(1-t-butoxycarbonylpiperidin-4-yl)-2-cyclobutyl-2-hydroxy-2-phenylacetamide 2.69 g of 2-cyclobutyl-2-hydroxy-2-phenylacetic acid, 2.17 g of 4-amino-1-t-butoxycarbonylpiperidine, 2.09 g of 1,1'-carbonyldiimidazole and 1.58 g of 4-dimethylaminopyridine were dissolved in 100 ml of N,N-dimethylformamide at room temperature, and this solution was stirred overnight. After the addition of water, the reaction mixture was extracted with diethyl ether. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: hexane/ ethyl acetate=10/1 to 4/1) to obtain 2.18 g of the title compound.

Step 3. Synthesis of N-(piperidin-4-yl)-2-cyclobutyl-2-hydroxy-2-phenylacetamide hydrochloride 1.0 g of N-(1-t-butoxycarbonylpiperidin-4-yl)-2-cyclobutyl-2-hydroxy-2-phenylacetamide was dissolved in 25 ml of a 4N hydrochloric acid solution in dioxane, and this solution was stirred at room temperature overnight. Then, the reaction mixture was evaporated to dryness under reduced pressure to obtain 0.83 g of the title compound.

Step 4. Synthesis of N-[1-(4-methyl-3-pentenyl)piperidin-4-yl]-2-cyclobutyl-2-hydroxy-2-phenylacetamide 0.83 g of N-(piperidin-4-yl)-2-cyclobutyl-2-hydroxy-2-phenylacetamide hydrochloride, 0.42 g of 5-bromo-2-methyl-2-pentene, 42 mg of potassium iodide and 1.42 g of anhydrous potassium carbonate were suspended in 25 ml of anhydrous N,N-dimethylformamide, and this suspension was stirred at 70° C. for 3 hours. The reaction mixture was cooled to room temperature, mixed with water, and then extracted with diethyl ether. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: hexane/ethyl acetate=2/1 to 1/4) to obtain 449 mg of the title compound.

$^1$H-NMR (CDCl$_3$, δ ppm): 1.38–1.56 (2H, m), 1.62 (3H, s), 1.69 (3H, s), 1.74–2.22 (12H, m), 2.28–2.38 (2H, m), 2.78–2.88 (2H, m), 3.32–3.42 (1H, m), 3.47 (1H, br s), 3.68–3.81 (1H, m), 5.03–5.12 (1H, m), 6.18 (1H, d, J=7.9 Hz), 7.25–7.38 (3H, m), 7.48–7.52 (2H, m).

Low Resolution FAB-MS (m/e, as (C$_{23}$ H$_{24}$N$_2$O$_2$+H)$^+$): 371

Example 2

N-(1-Hexylpiperidin-4-yl)-2-cyclobutyl-2-hydroxy-2-phenylacetamide

The title compound was prepared in the same manner as described in Step 4 of Example 1 using bromohexane.

$^1$H-NMR (CDCl$_3$, δ ppm): 0.87 (3H, t, J=6.8 Hz), 1.21–1.50 (8H, m), 1.55–2.12 (12H, m), 2.24–2.31 (2H, m), 2.70–2.82 (2H, m), 3.25–3.60 (2H, m), 3.64–3.78 (1H, m), 6.11 (1H, d, J=9.6 Hz), 7.23–7.37 (3H, m), 7.45–7.51 (2H, m).

Example 3

N-{1-[(Z)-3-Hexenyl]piperidin-4-yl}-2-cyclobutyl-2-hydroxy-2-phenylacetamide

The title compound was prepared in the same manner as described in Step 4 of Example 1 using (Z)-3-hexenyl methanesulfonate.

$^1$H-NMR (CDCl$_3$, δ ppm): 0.95 (3H, t, J=7.5 Hz), 1.32–1.51 (2H, m), 1.70–2.16 (12H, m), 2.16–2.27 (2H, m), 2.30–2.39 (2H, m), 2.72–2.85 (2H, m), 3.30–3.60 (2H, m), 3.65–3.79 (1H, m), 5.28 (1H, dtt, J=10.7, 6.9, 1.3 Hz), 5.42 (1H, dtt, J=10.7, 7.1, 1.3 Hz), 6.14 (1H, d, J=7.8 Hz), 7.22–7.38 (3H, m), 7.45–7.51 (2H, m).

Example 4

N-{1-[(E)-3-Hexenyl]piperidin-4-yl}-2-cyclobutyl-2-hydroxy-2-phenylacetamide

The title compound was prepared in the same manner as described in Step 4 of Example 1 using (E)-3-hexenyl methanesulfonate.

$^1$H-NMR (CDCl$_3$, δ ppm): 0.95 (3H, t, J=7.5 Hz), 1.32–1.50 (2H, m), 1.60–2.21 (14H, m), 2.31–2.39 (2H, m), 2.72–2.85 (2H, m), 3.30–3.49 (2H, m), 3.64–3.79 (1H, m), 5.34 (1H, dtt, J=15.3, 7.0, 1.3 Hz), 5.49 (1H, dtt, J=15.3, 6.2, 1.3 Hz), 6.12 (1H, d, J=8.6 Hz), 7.23–7.38 (3H, m), 7.47–7.51 (2H, m).

Example 5

N-[1-(6-Methyl-5-heptenyl)piperidin-4-yl]-2-cyclobutyl-2-hydroxy-2-phenylacetamide The title compound was prepared in the same manner as described in Step 4 of Example 1 using 6-methyl-5-heptenyl methanesulfonate.

$^1$-H-NMR (CDCl$_3$, δ ppm): 1.25–1.37 (2H, m), 1.42–1.56 (4H, m), 1.58 (3H, s), 1.67 (3H, d, J=1.2 Hz), 1.72–2.18 (12H, m), 2.31–2.46 (2H, m), 2.79–2.91 (2H, m), 3.20–3.60 (2H, m), 3.65–3.80 (1H, m), 5.03–5.11 (1H, m), 6.18–6.28 (1H, m), 7.22–7.36 (3H, m), 7.46–7.51 (2H, m).

Example 6

N-[1-(4-Methyl-3-pentenyl)piperidin-4-yl]-2-cyclobutyl-2-(4-fluorophenyl)-2-hydroxyacetamide The title compound was prepared in the same manner as described in Example 1 using cyclobutyl 4-fluorophenyl ketone.

$^1$H-NMR (CDCl$_3$, δ ppm): 1.37–1.55 (2H, m), 1.61 (3H, s), 1.68 (3H, s), 1.72–1.97 (7H, m), 2.00–2.21 (5H, m), 2.31–2.36 (2H, m), 2.78–2.99 (2H, m), 3.20–3.50 (2H, m), 3.63–3.79 (1H, m), 5.01–5.09 (1H, m), 6.22 (1H, d, J=8.2 Hz), 6.97–7.05 (2H, m), 7.44–7.51 (2H, m).

Low Resolution FAB-MS (m/e, as (C$_{23}$ H$_{33}$FN$_2$O$_2$+H)$^+$): 389

Example 7

N-[1-(5-Methyl-4-hexenyl)piperidin-4-yl]-2-cyclobutyl-2-hydroxy-2-phenylacetamide The title compound was prepared in the same manner as described in Step 4 of Example 1 using 5-methyl-4-hexenyl methanesulfonate.

$^1$H-NMR (CDCl$_3$, δ ppm): 1.37–1.56 (4H, m), 1.58 (3H, s), 1.68–2.11 (15H, m), 2.26–2.34 (2H, m), 2.72–2.84 (2H, m), 3.30–3.55 (2H, m), 3.62–3.80 (1H, m), 5.05–5.12 (1H, m), 6.14 (1H, d, J=7.8 Hz), 7.24–7.37 (3H, m), 7.46–7.52 (2H, m).

Example 8

N-[1-(4-Methylpentyl)piperidin-4-yl]-2-cyclobutyl-2-hydroxy-2-phenylacetamide

The title compound was prepared in the same manner as described in Step 4 of Example 1 using 1-bromo-4-methylpentane.

$^1$H-NMR (CDCl$_3$, δ ppm): 0.87 (6H, d, J=6.6 Hz), 1.10–1.20 (2H, m), 1.34–1.60 (5H, m), 1.70–2.15 (10H, m), 2.24–2.33 (2H, m), 2.72–2.86 (2H, m), 3.30–3.60 (2H, m), 3.65–3.79 (1H, m), 6.13 (1H, d, J=8.1 Hz), 7.22–7.38 (3H, m), 7.46–7.52 (2H, m).

Example 9

N-[1-(4-Methyl-2-pentynyl)piperidin-4-yl]-2-cyclobutyl-2-hydroxy-2-phenylacetamide The title compound was prepared in the same manner as described in Step 4 of Example 1 using 1-bromo-4-methyl-2-pentyne.

$^1$H-NMR (CDCl$_3$, δ ppm): 1.15 (6H, d, J=6.9 Hz), 1.30–1.55 (2H, m), 1.65–2.15 (8H, m), 2.15–2.35 (2H, m), 2.45–2.65 (1H, m), 2.68–2.85 (2H, m), 3.21 (2H, d, J=3.0 Hz), 3.25–3.55 (2H, m), 3.60–3.80 (1H, m), 6.18 (1H, d, J=8.3 Hz), 7.20–7.40 (3H, m), 7.45–7.53 (2H, m).

Example 10

N-[1-(5-Methyl-3-hexynyl)piperidin-4-yl]-2-cyclobutyl-2-hydroxy-2-phenylacetamide The title compound was prepared in the same manner as described in Step 4 of Example 1 using 1-bromo-5-methyl-3-hexyne.

$^1$H-NMR (CDCl$_3$, δ ppm): 1.12 (6H, d, J=6.9 Hz), 1.25–1.50 (2H, m), 1.65–2.05 (8H, m), 2.05–2.23 (2H, m), 2.24–2.35 (2H, m), 2.42–2.60 (3H, m), 2.68–2.85 (2H, m), 3.25–3.55 (2H, m), 3.60–3.80 (1H, m), 6.12 (1H, d, J=7.6 Hz), 7.20–7.40 (3H, m), 7.44–7.53 (2H, m).

Example 11

N-[1-(4-Methyl-3-pentenyl)piperidin-4-yl]-2-cyclohexyl-2-hydroxy-2-phenylacetamide The title compound was prepared in the same manner as described in Steps 2 to 4 of Example 1 using 2-cyclohexyl-2-hydroxy-2-phenylacetic acid.

$^1$H-NMR (CDCl$_3$, δ ppm): 0.80–0.95 (1H, m), 1.09–1.39 (6H, m), 1.45–1.98 (7H, m), 1.61 (3H, s), 1.68 (3H, s), 2.05–2.23 (4H, m), 2.31–2.45 (3H, m), 2.75 (1H, s), 2.80–2.92 (2H, m), 3.65–3.80 (1H, m), 5.01–5.09 (1H, m), 6.55–6.59 (1H, m), 7.23–7.38 (3H, m), 7.57–7.61 (2H, m).

Low Resolution FAB-MS (m/e, as (C$_{25}$H$_{38}$N$_2$O$_2$+H)$^+$): 399

Example 12

N-{1-[(4S)-4-Methylhexyl)piperidin-4-yl}-2-cyclohexyl-2-hydroxy-2-phenylacetamide The title compound was prepared in the same manner as described in Example 11 using (4S)-4-methyl hexyl methanesulfonate.

$^1$H-NMR (CDCl$_3$, δ ppm): 0.84 (3H, t, J=7.2 Hz), 0.84 (3H, d, J=6.3 Hz), 1.01–1.18 (3H, m), 1.18–1.38 (7H, m), 1.40–1.60 (4H, m), 1.60–1.74 (4H, m), 1.74–1.84 (2H, m), 1.86–1.96 (1H, m), 2.03–2.37 (2H, m), 2.28–2.45 (3H, m), 2.75 (1H, s), 2.80–2.92 (2H, m), 3.66–3.79 (1H, m), 6.58 (1H, d, J=8.3 Hz), 7.23–7.28 (1H, m), 7.31–7.37 (2H, m), 7.57–7.61 (2H, m).

Low Resolution FAB-MS (m/e, as (C$_{26}$H$_{24}$N$_2$O$_2$+H)$^+$): 415

Example 13

N-[1-(4,5-Dimethyl-4-hexenyl)piperidin-4-yl]-2-cyclobutyl-2-hydroxy-2-phenylacetamide The title compound was prepared in the same manner as described in Step 4 of Example 1 using 4,5-dimethyl-4-hexenyl methanesulfonate.

$^1$H-NMR (CDCl$_3$, δ ppm): 1.30–1.45 (2H, m), 1.45–1.58 (2H, m), 1.62 (9H, s), 1.70–2.15 (12H, m), 2.22–2.30 (2H, m), 2.70–2.82 (2H, m), 3.30–3.42 (1H, m), 3.49 (1H, s), 3.64–3.79 (1H, m), 6.14 (1H, d, J=8.3 Hz), 7.25–7.38 (3H, m), 7.47–7.53 (2H, m).

Example 14

N-[1-(4-Methyl-3-pentenyl)piperidin-4-yl]-2-cyclopropyl-2-hydroxy-2-phenylacetamide The title compound was prepared in the same manner as described in Steps 2 to 4 of Example 1 using 2-cyclopropyl-2-hydroxy-2-phenylacetic acid.

$^1$H-NMR (CDCl$_3$, δ ppm): 0.47–0.67 (4H, m), 1.38–1.59 (3H, m), 1.61 (3H, s), 1.69 (3H, s), 1.85–1.97 (2H, m), 2.06–2.21 (4H, m), 2.25–2.36 (2H, m), 2.75–2.88 (2H, m), 3.72–3.86 (1H, m), 5.03–5.08 (1H, m), 6.09 (1H, d, J=8.2 Hz), 7.27–7.39 (3H, m), 7.57–7.62 (2H, m).

Low Resolution FAB-MS (m/e, as (C$_{22}$H$_{32}$N$_2$O$_2$+H)$^+$): 357

Example 15

N-{1-[(4S)-4-Methylhexyl]piperidin-4-yl}-2-cyclopropyl-2-hydroxy-2-phenylacetamide The title compound was prepared in the same manner as described in Example 14 using (4S)-4-methylhexyl methanesulfonate.

$^1$H-NMR (CDCl$_3$, δ ppm): 0.48–0.68 (4H, m), 0.85 (3H, t, J=7.2 Hz), 0.85 (3H, d, J=6.3 Hz), 1.01–1.18 (2H, m), 1.21–1.38 (2H, m), 1.40–1.75 (4H, m), 1.57 (1H, ddd, J=5.5, 8.1, 13.5 Hz), 1.85–1.98 (2H, m), 2.06–2.18 (2H, m), 2.32 (2H, t, J=7.6 Hz), 2.77–2.90 (2H, m), 3.28–3.40 (1H, br s), 3.72–3.87 (2H, m), 6.04 (1H, d, J=6.9 Hz), 7.26–7.40 (3H, m), 7.58–7.63 (2H, m).

Low Resolution FAB-MS (m/e, as (C$_{23}$H$_{36}$N$_2$O$_2$+H)$^+$): 373

Example 16

N-[1-(4-Methyl-3-pentenyl)piperidin-4-yl]-2-cyclopentyl-2-hydroxy-2-phenylacetamide The title compound was prepared in the same manner as described in Steps 2 to 4 of Example 1 using 2-cyclopentyl-2-hydroxy-2-phenylacetic acid.

$^1$H-NMR (CDCl$_3$, δ ppm): 1.12–1.28 (1H, m), 1.32–1.90 (11H, m), 1.60 (3H, s), 1.68 (3H, s), 2.03–2.19 (4H, m), 2.26–2.32 (2H, m), 2.72–2.82 (2H, m), 2.95–3.09 (1H, m), 3.14 (1H, s), 3.62–3.77 (1H, m), 5.04–5.10 (1H, m), 6.31 (1H, d, J=7.9 Hz), 7.23–7.38 (3H, m), 7.57–7.61 (2H, m).

Low Resolution FAB-MS (m/e, as $(C_{24}H_{36}N_2O_2+H)^+$): 385

Example 17

N-{1-[(4S)-4-Methylhexyl)piperidin-4-yl}-2-cyclopentyl-2-hydroxy-2-phenylacetamide The title compound was prepared in the same manner as described in Example 16 using (4S)-4-methylhexyl methanesulfonate.

$^1$H-NMR (CDCl$_3$, δ ppm): 0.84 (3H, d, J=6.4 Hz), 0.85 (3H, t, J=7.2 Hz), 1.00–1.74 (17H, m), 1.78–1.91 (2H, m), 2.02–2.34 (2H, m), 2.30 (2H, t, J=7.6 Hz), 2.73–2.87 (2H, m), 2.98–3.10 (1H, m), 3.10 (1H, s), 3.65–3.79 (1H, m), 6.33 (1H, d, J=8.6 Hz), 7.23–7.30 (1H, m), 7.31–7.37 (2H, m), 7.57–7.62 (2H, m).

Low Resolution FAB-MS (m/e, as $(C_{25}H_{40}N_2O_2+H)^+$): 401

Example 18

(2R)-N-[1-(4-Methyl-3-pentenyl)piperidin-4-yl]-2-(1-cyclopenten-1-yl)-2-hydroxy-2-phenylacetamide Step 1. Synthesis of (2R)-2-(1-cyclopenten-1-yl)-2-hydroxy-2-phenylacetic acid Step 1-1. Synthesis of (2S,5S)-2-(t-butyl)-5-(1-hydroxycyclopentan-1-yl)-5-phenyl-1,3-dioxolan-4-one 1.3 ml of a 1.5M lithium diisopropylamide solution in hexane was added dropwise at −78° C. to a solution of 379 mg of (2S,5S)-2-(t-butyl)-5-phenyl-1,3-dioxolan-4-one, which had been synthesized according to the method of D. Seebach et al. [Tetrahedron, Vol. 40, pp. 1313–1324 (1984), in 15 ml of tetrahydrofuran, and this mixture was stirred for 45 minutes. After the addition of 0.25 ml of cyclopentanone, the resulting mixture was warmed to room temperature over a period of 2.5 hours. The reaction mixture was poured into a saturated aqueous solution of ammonium chloride and extracted with diethyl ether. The organic layer was washed with water and a saturated aqueous solution of sodium chloride and then dried over anhydrous magnesium sulfate. After the solvent was distilled off under reduced pressure, the resulting residue was purified by silica gel column chromatography (developing solvent: hexane/ethyl acetate= 4/1) to obtain 126 mg of the title compound.

Step 1-2. Synthesis of (2S,5S)-2-(t-butyl)-5-(1-cyclopenten-1-yl)-5-phenyl-1,3-dioxolan-4-one 126 mg of (2S,5S)-2-(t-butyl)-5-(1-hydroxycyclopentan-1-yl)-5-phenyl-1,3-dioxolan-4-one was dissolved in 8 ml of pyridine, and 2 ml of thionyl chloride was added dropwise thereto at 0° C. After being stirred at room temperature for 14 hours, the reaction mixture was poured into ice water and extracted with diethyl ether. The organic layer was washed with water and a saturated aqueous solution of sodium chloride and then dried over anhydrous magnesium sulfate. After the solvent was distilled off under reduced pressure, the resulting residue was purified by preparative thin-layer chromatography [Kieselgel ™ 60F$_{254}$, Art 5744 (manufactured by E. Merck); developing solvent: hexane/ethyl acetate=19/1] to obtain 99 mg of the title compound.

Step 1-3. Synthesis of (2R)-2-(1-cyclopenten-1-yl)-2-hydroxy-2-phenylacetic acid 96 mg of (2S,5S)-2-(t-butyl)-5-(1-cyclopenten-1-yl)-5-phenyl-1,3-dioxolan-4-one was dissolved in 4 ml of methanol, and 2 ml of a 1N aqueous solution of sodium hydroxide was added thereto. This mixture was stirred at room temperature for 4 hours. After the methanol was distilled off under reduced pressure, the resulting residue was washed with diethyl ether, acidified with 1N hydrochloric acid, and then extracted with chloroform. The organic layer was washed with a saturated aqueous solution of sodium chloride and then dried over anhydrous magnesium sulfate. Thereafter, the solvent was distilled off under reduced pressure to obtain 70 mg of the title compound.

Step 2. Synthesis of (2R)-N-[1-(4-methyl-3-pentenyl)piperidin-4-yl]-2-(1-cyclopenten-1-yl)-2-hydroxy-2-phenylacetamide The title compound was synthesized in the same manner as described in Steps 2 to 4 of Example 1 using (2R)-2-(1-cyclopenten-1-yl)-2-hydroxy-2-phenylacetic acid.

$^1$H-NMR (CDCl$_3$, δ ppm): 1.35–2.48 (1 6H, m), 1.61 (3H, s), 1.69 (3H, s), 2.70–2.90 (2H, m), 3.70–3.92 (2H, m), 5.00–5.12 (1H, m), 5.62–5.70 (1H, m), 5.98–6.11 (1H, m), 7.27–7.40 (3H, m), 7.42–7.52 (2H, m).

Low Resolution FAB-MS (m/e, as $(C_{24}H_{34}N_2O_2+H)^+$): 383

Example 19

Synthesis of [1-(4-methyl-3-pentenyl)piperidin-4-yl] 2-cyclobutyl-2-hydroxy-2-phenylacetate Step 1. Synthesis of (1-t-butoxycarbonylpiperidin-4-yl) 2-cyclobutyl-2-hydroxy-2-phenylacetate 4.48 g of the 2-cyclobutyl-2-hydroxy-2-phenylacetic acid obtained in Step 1 of Example 1 and 3.41 g of 1,1'-carbonyldiimidazole were dissolved in 100 ml of N,N-dimethylformamide, and this solution was stirred at room temperature for an hour. After this solution was cooled to 0° C., 3.60 g of 4-hydroxy-1-t-butoxycarbonylpiperidine and 0.36 g of sodium hydride were added thereto, and the resulting mixture was stirred at room temperature for 4 hours. After the addition of water, the reaction mixture was extracted with diethyl ether. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: hexane/ethyl acetate=10/1 to 4/1) to obtain 5.39 g of the title compound.

Step 2. Synthesis of (piperidin-4-yl) 2-cyclobutyl-2-hydroxy-2-phenylacetate hydrochloride A 10% methanolic solution of hydrochloric acid was added to a solution of 2.68 g of (1-t-butoxycarbonylpiperidin-4-yl)-2-cyclobutyl-2-hydroxy-2-phenylacetate in 50 ml of methanol, and this mixture was stirred at room temperature for 10 hours. The solvent was distilled off under reduced pressure to obtain 2.24 g of the title compound.

Step 3. Synthesis of [1-(4-methyl-3-pentenyl)piperidin-4-yl] 2-cyclobutyl-2-hydroxy-2-phenylacetate 50 mg of (piperidin-4-yl) 2-cyclobutyl-2-hydroxy-2-phenylacetate hydrochloride, 25 mg of 5-bromo-2-methyl-2-pentene, 25 mg of potassium iodide and 47 mg of anhydrous potassium carbonate were suspended in 5 ml of anhydrous N,N-dimethylformamide, and this suspension was stirred at 70° C. for 3 hours. The reaction mixture was cooled to room temperature, mixed with water, and then extracted with diethyl ether. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: chloroform/methanol=20/1) to obtain 35 mg of the title compound.

¹H-NMR (CDCl₃, δ ppm): 1.58–2.22 (19H, m), 2.23–2.56 (4H, m), 2.59–2.69 (1H, m), 3.27–3.38 (1H, m), 3.82–3.87 (1H, br s), 4.80–4.90 (1H, m), 5.06–5.13 (1H, m), 7.21–7.37 (3H, m), 7.56–7.61 (2H, m).

Low Resolution FAB-MS (m/e, as $(C_{23}H_{33}NO_3+H)^+$): 372

Example 20

[(4-Methylpentyl)piperidin-4-yl]-2-cyclobutyl-2-hydroxy-2-phenylacetate

The title compound was prepared in the same manner as described in Step 3 of Example 19 using 1-bromo-4-methylpentane.

¹H-NMR (CDCl₃, δ ppm): 0.88 (6H, d, J=6.6 Hz), 1.12–1.20 (2H, m), 1.41–2.15 (13H, m), 2.20–2.68 (6H, m), 3.26–3.38 (1H, m), 3.84 (1H, s), 4.80–4.90 (1H, m), 7.21–7.37 (3H, m), 7.56–7.62 (2H, m).

Low Resolution FAB-MS (m/e, as $(C_{23}H_{35}NO_3+H)^+$): 374

Example 21

[1-(1-Cyclohexylethyl)piperidin-4-yl]-2-cyclobutyl-2-hydroxy-2-phenylacetate

The title compound was prepared in the same manner as described in Step 3 of Example 19 using 1-cyclohexylethyl methanesulfonate.

¹H-NMR (CDCl₃, δ ppm): 0.78–0.95 (5H, m), 1.10–1.36 (4H, m), 1.50–2.76 (20H, m), 3.25–3.39 (1H, m), 3.85 (1H, s), 4.75–4.86 (1H, m), 7.21–7.37 (3H, m), 7.55–7.61 (2H, m).

Low Resolution FAB-MS (m/e, as $(C_{23}H_{37}NO_3+H)^+$): 400

Example 22

(2R)-N-{1-[(4S)-4-Methylhexyl]piperidin-4-yl}-2-cyclobutyl-2-hydroxy-2-phenylacetamide hydrochloride Step 1. Optical resolution of 2-cyclobutyl-2-hydroxy-2-phenylacetic acid In the light of the method of Canter et al. (J. Med. Chem., Vol. 34, pp. 3065–3074), optical isomers of 2-cyclobutyl-2-hydroxy-2-phenylacetic acid were obtained in the following manner.

4 g of 2-cyclobutyl-2-hydroxy-2-phenylacetic acid and 2.35 g of R-(+)-methylbenzylamine were dissolved in 60 ml of anhydrous toluene by the application of heat, and this solution was allowed to stand at room temperature for 24 hours. The white needle-like crystals which separated out were dissolved again in 100 ml of toluene, and this solution was allowed to stand for 24 hours. The foregoing procedure was repeated five times to obtain 0.37 g of the R-(+)-methylbenzylamine salt of the title compound. This was dissolved in a mixture of diethyl ether and 1N hydrochloric acid. The organic layer was washed with water and a saturated aqueous solution of sodium chloride and then dried over anhydrous magnesium sulfate. Thereafter, the solvent was distilled off under reduced pressure to obtain 0.22 g of (2R)-2-cyclobutyl-2-hydroxy-2-phenylacetic acid.

$[\alpha]_D^\circ=+11.03°$ (C=3.10, ETOH)

With respect to the (2S)-isomer which is the antipode thereof, the same procedure was repeated using (S)-(–)-methylbenzylamine. Thus, there was obtained 0.13 g of (2S)-2-cyclobutyl-2-hydroxy-2-phenylacetic acid.

$[\alpha]_D^{20}=-14.5°$ (C=6.15, MeOH)

Step 2. Synthesis of 4-t-butoxycarbonylamino-1-[(4S)-4-methylhexyl]piperidine 315 mg of (4S)-4-methylhexyl methanesulfonate, 320 mg of 4-t-butoxycarbonylaminopiperidine, 280 mg of anhydrous potassium carbonate and 266 mg (1.6 mmol) of potassium iodide were suspended in 10 ml of N,N-dimethyl formamide, and this suspension was stirred at 70° C. for 3 hours. The reaction mixture was cooled to room temperature, mixed with water, and then extracted with diethyl ether. The organic layer was washed with a saturated aqueous solution of sodium chloride and dried over anhydrous magnesium sulfate. After the solvent was distilled off under reduced pressure, the resulting residue was purified by silica gel column chromatography (developing solvent: hexane/ethyl acetate=1/1) to obtain 328 mg of the title compound.

Step 3. Synthesis of 4-amino-1-[(4S)-4-methylhexyl]piperidine dihydrochloride 2 ml of a 10% methanolic hydrochloric acid solution was added to a solution of 320 mg (1.1 mmol) of 4-t-butoxycarbonylamino-1-[(4S)-4-methylhexyl]piperidine in 5 ml of methanol. After this mixture was stirred at room temperature for an hour, the solvent was distilled off under reduced pressure to obtain 296 mg (quantitative yield) of the title compound.

Step 4. Synthesis of (2R)-N-{1-[(4S)-4-methylhexyl]piperidin-4-yl}-2-cyclobutyl-2-hydroxy-2-phenylacetamide 60 mg of (2R)-2-cyclobutyl-2-hydroxy-2-phenylacetic acid and 47 mg of 1,1'-carbonyldiimidazole were dissolved in 3 ml of anhydrous N,N-dimethylformamide, and this mixture was stirred at room temperature for 2 hours. 95 mg of 4-amino-1-[(4S)-4-methylhexyl]piperidine dihydrochloride and 86 mg of 4-dimethylaminopyridine were added thereto, the resulting mixture was stirred at room temperature overnight. The reaction mixture was mixed with water and then extracted with diethyl ether. The organic layer was washed with a saturated aqueous solution of sodium chloride and dried over anhydrous magnesium sulfate. After the solvent was distilled off under reduced pressure, the resulting residue was purified by preparative thin layer chromatography [Kieselgel™ 60F₂₅₄, Art 5744 (manufactured by E. Merck); developing solvent; chloroform/methanol=9/1] to obtain 67 mg of the title compound.

Step 5. Synthesis of (2R)-N-{1-[(4S)-4-methylhexyl]piperidin-4-yl}-2-cyclobutyl-2-hydroxy-2-phenylacetamide hydrochloride 67 mg of (2R)-N-{1-[(4S)-4-methylhexyl]piperidin-4-yl}-2-cyclobutyl-2-hydroxy-2-phenylacetamide was dissolved in a 4N hydrochloric acid solution in dioxane, and this solution was stirred at room temperature for 10 minutes. After the solvent was distilled off under reduced pressure, the resulting solid was recrystallized from chloroform-diethyl ether to obtain 50 mg of the title compound.

¹H-NMR (CD₃OD, δ ppm): 0.90 (3H, t, J=7.3 Hz), 0.91 (3H, d, J=6.2 Hz), 1.10–1.27 (2H, m), 1.30–1.46 (3H, m), 1.62–2.29 (12H, m), 2.93–3.13 (4H, m), 3.40–3.70 (3H, m), 3.80–3.95 (1H, m), 7.19–7.33 (3H, m), 7.48–7.54 (2H, m).

Example 23

Synthesis of [1-(3-cyclopentylidenepropyl)piperidin-4-yl]-2-cyclobutyl-2-hydroxy-2-phenylacetate According to the method of A. Chesnyl et al. [Synthetic Communications, Vol. 20, pp. 3167–3180 (1990)], 50 mg of the 2-cyclobutyl-2-hydroxy-2-phenylacetic acid obtained in Step 1 of Example 1 and a catalytic amount of DBU were dissolved in 2 ml of tetrahydrofuran, and 15 μl of acrolein was added thereto at −15° C., followed by stirring for 20 minutes. The resulting solution was added at 0° C. to an ylide compound prepared from 156 mg of cyclopentyltriphenylphosphonium iodide and 200 μl of n-butyl lithium (as a 1.69M hexane solution), and this mixture was stirred at 0° C. for 30 minutes and then at room temperature for 4 hours. After the addition of 20 ml of water, the reaction mixture was extracted with ethyl acetate (30 ml×3). The organic layer was washed with a saturated aqueous solution of sodium chloride and then dried over anhydrous magnesium sulfate. After the solvent was distilled off under reduced pressure, the resulting residue was purified by thin-layer chromatography [Kieselgel™ 60F$_{254}$, Art 5744 (manufactured by E. Merck); developing solvent: hexane/ethyl acetate=1/2] to obtain 2.0 mg of the title compound.

$^1$H-NMR (CDCl$_3$, δ ppm): 1.55–2.41 (24H, m), 2.43–2.55 (1H, m), 2.59–2.70 (1H, m), 3.26–3.39 (1H, m), 3.84 (1H, s), 4.80–4.89 (1H, m), 5.17–5.25 (1H, m), 7.22–7.37 (3H, m), 7.56–7.61 (2H, m).

Low Resolution FAB-MS (m/e, as $(C_{25}H_{35}NO_3+H)^+$): 398

Example 24

Synthesis of N-[(E)-1-(4-methyl-4-hexenyl) piperidin-4-yl]-2-cyclobutyl-2-hydroxy-2-phenylacetamide and N-[(Z)-1-(4-methyl-4-hexenyl) piperidin-4-yl]-2-cyclobutyl-2-hydroxy-2-phenylacetamide Step 1. Synthesis of N-[1-(4-oxopentyl)piperidin-4-yl]-2-cyclobutyl-2-hydroxy-2-phenylacetamide ethylene ketal 98 mg of the N-(piperidin-4-yl)-2-cyclobutyl-2-hydroxy-2-phenylacetamide hydrochloride obtained in Step 3 of Example 1, 50 μl of 2-(3-chloropropyl)-2-methyl-1,3-dioxolan, 50 mg of anhydrous potassium carbonate and 10 mg of potassium iodide were suspended in 3 ml of anhydrous N,N-dimethylformamide, and this suspension was stirred at 60° C. for 3 hours. After the reaction mixture was cooled to room temperature, the solvent was distilled off under reduced pressure. The resulting residue was mixed with water and then extracted with chloroform. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: chloroform to chloroform/methanol=10/1) to obtain 91 mg of the title compound.

Step 2. Synthesis of N-[1-(4-oxopentyl)piperidin-4-yl]-2-cyclobutyl-2-hydroxy-2-phenylacetamide 86 mg of N-[1-(4-oxopentyl)piperidin-4-yl]-2-cyclobutyl-2-hydroxy-2-phenylacetamide ethylene ketal was dissolved in 2 ml of tetrahydrofuran, and 2 ml of 1N hydrochloric acid was added thereto. After this mixture was stirred at room temperature for an hour, the tetrahydrofuran was distilled off under reduced pressure. The resulting residue was dissolved in a mixture of chloroform and an aqueous solution of sodium hydrogen carbonate. The organic layer was washed with a saturated aqueous solution of sodium chloride and then dried over anhydrous magnesium sulfate. Thereafter, the solvent was distilled off under reduced pressure to obtain 68 mg of the title compound.

Step 3. Synthesis of N-[1-(E)-(4-methyl-4-hexenyl) piperidin-4-yl]-2-cyclobutyl-2-hydroxy-2-phenylacetamide and N-[1-(Z)-(4-methyl-4-hexenyl)piperidin-4-yl]-2-cyclobutyl-2-hydroxy-2-phenylacetamide 62 mg of N-[1-(4-oxopentyl)piperidin-4-yl]-2-cyclobutyl-2-hydroxy-2-phenylacetamide was added at 0° C. to an ylide compound prepared from 124 mg of ethyltriphenylphosphonium bromide and 200 μl of n-butyl lithium (as a 1.62M hexane solution), and this mixture was stirred at 0° C. for 30 minutes and then at room temperature for 4 hours. After the solvent was distilled off under reduced pressure, the resulting residue was mixed with 20 ml of water and then extracted with chloroform (30 ml×3). The organic layer was washed with a saturated aqueous solution of sodium chloride and then dried over anhydrous magnesium sulfate. After the solvent was distilled off under reduced pressure, the resulting residue was purified by preparative thin-layer chromatography [Kieselgel™ 60F$_{254}$, Art 5744 (manufactured by E. Merck); developing solvent: chloroform to chloroform/methanol=10/1) to obtain 18.0 mg of N-[1-(Z)-(4-methyl-4-hexenyl)piperidin-4-yl]-2-cyclobutyl-2-hydroxy-2-phenylacetamide and 9.0 mg of N-[1-(E)-(4-methyl-4-hexenyl)piperidin-4-yl]-2-cyclobutyl-2-hydroxy-2-phenylacetamide.

NMR spectrum of N-[1-(Z)-(4-methyl-4-hexenyl) piperidin-4-yl]-2-cyclobutyl-2-hydroxy-2-phenylacetamide.

$^1$H-NMR (CDCl$_3$, δ ppm): 1.35–2.17 (22H, m), 2.27–2.36 (2H, m), 2.75–2.90 (2H, m), 3.20–3.60 (2H, m), 3.66–3.80 (1H, m), 5.21 (1H, q, J=6.8 Hz), 6.18 (1H, d, J=7.5 Hz), 7.24–7.38 (3H, m), 7.46–7.52 (2H, m).

NMR spectrum of N-[1-(E)-(4-methyl-4-hexenyl) piperidin-4-yl]-2-cyclobutyl-2-hydroxy-2-phenylacetamide.

$^1$H-NMR (CDCl$_3$, δ ppm): 1.45–2.22 (22H, m), 2.33–2.41 (2H, m), 2.85–2.98 (2H, m), 3.30–3.60 (2H, m), 3.70–3.85 (1H, m), 5.17–5.26 (1H, m), 6.25 (1H, d, J=7.6 Hz), 7.27–7.41 (3H, m), 7.47–7.58 (2H, m).

Example 25

(2R)-N-[1-(4-Methyl-3-pentenyl)piperidin-4-yl]-2-cyclobutyl-2-hydroxy-2-phenylacetamide fumarate Step 1. Synthesis of 4-amino-1-(4-methyl-3-pentenyl) piperidine dihydrochloride The title compound was prepared in the same manner as described in Steps 2 to 3 of Example 22 using 5-bromo-2-methyl-2-pentene.

Step 2. Synthesis of (2R)-N-[1-(4-methyl-3-pentenyl) piperidin-4-yl]-2-cyclobutyl-2- hydroxy-2-phenylacetamide The title compound was prepared in the same manner as described in step 4 of Example 22 using 4-amino-1-(4-methyl-3-pentenyl)piperidine dihydrochloride.

Step 3. Synthesis of (2R)-N-[1-(4-methyl-3-pentenyl) piperidin-4-yl]-2-cyclobutyl-2-hydroxy-2-phenylacetamide fumarate 42 mg of (2R)-N-[1-(4-methyl-3-pentenyl)piperidin-4-yl]-2-cyclobutyl-2-hydroxy-2-phenylacetamide was dissolved in ethanol, and 13.2 mg of fumaric acid was added thereto. Recrystallization from hexane/ether gave 48 mg of the title compound.

$^1$H-NMR (CD$_3$ OD, δ ppm): 1.67 (3H, s), 1.72 (3H, s), 1.74–2.20 (10H, m), 2.35–2.46 (2H, m), 2.90–3.05 (4H, m), 3.39–3.55 (3H, m), 3.79–3.92 (1H, m), 5.03–5.12 (1H, m), 6.69 (2H, s), 7.19–7.34 (3H, m), 7.49–7.54 (2H, m).

Example 26

Synthesis of N-{1-[(4S)-4-methylhexyl]piperidin-4-yl}-2-cyclobutyl-2-hydroxy-2-phenylacetamide The title compound was prepared in the same manner as described in Step 4 of Example 1 using (4S)-4-methylhexyl sulfonate.

$^1$H-NMR (CDCl$_3$, δ ppm): 0.84 (3H, d, J=6.4 Hz), 0.85 (3H, t, J=7.2 Hz), 1.00–1.57 (10H, m), 1.70–2.15 (11H, m), 2.27 (2H, t, J=7.8 Hz), 2.71–2.84 (2H, m), 3.30–3.53 (2H, m), 3.66–3.79 (1H, m), 6.12 (1H, d, J=7.9 Hz), 7.23–7.38 (3H, m).

Low Resolution FAB-MS (m/e, as (C$_{24}$H$_{38}$N$_2$O$_2$+H)$^+$): 387

Example 27

Synthesis of N-[1-(4-methyl-3-pentenyl)piperidin-4-yl]-2-cyclopentyl-2-hydroxy-2-phenylacetamide Step 1. Synthesis of 2-cyclopentyl-2-hydroxy-2-phenylacetic acid A solution of cyclopentylmagnesium chloride in diethyl ether was added dropwise to a solution of 23.5 g of ethyl phenylglyoxylate in 200 ml of tetrahydrofuran under cooling with ice, and this mixture was stirred at the same temperature for 30 minutes. After the addition of a saturated aqueous solution of ammonium chloride, the reaction mixture was extracted with ethyl acetate. The organic layer was washed with a saturated aqueous solution of sodium chloride and then dried over anhydrous magnesium sulfate. After the solvent was distilled off under reduced pressure, the resulting residue was purified by silica gel column chromatography (hexane/ethyl acetate=30/1 to 20/1) to obtain 11 g of ethyl 2-cyclopentyl-2-hydroxy-2-phenylacetate. This was dissolved in 40 ml of methanol, and 20 ml of a 4N aqueous solution of sodium hydroxide was added thereto at room temperature. This mixture was stirred at the same temperature for 2 hours and then at 50° C. for an hour. After the methanol was distilled off under reduced pressure, the aqueous layer was made weakly acidic with 4N hydrochloric acid and then extracted with ethyl acetate. The extract was washed with a saturated aqueous solution of sodium chloride and then dried over anhydrous sodium sulfate. After the solvent was distilled off under reduced pressure, the resulting solid was washed with diethyl ether/hexane (=1/1) to obtain 8.7 g of the title compound.

Step 2. Synthesis of N-(piperidin-4-yl)-2-cyclopentyl-2-hydroxy-2-phenylacetamide The hydrochloride of the title compound was prepared in the same manner as described in Steps 2 to 3 of Example 1 using 2-cyclopentyl-2-hydroxy-2-phenylacetic acid. The hydrochloride was dissolved in a mixture of ethyl acetate and a 1N aqueous solution of sodium hydroxide. After the organic layer was dried over anhydrous sodium sulfate, the solvent was distilled off under reduced pressure to obtain the title compound.

Step 3. Synthesis of N-[1-(4-methyl-3-pentenyl)piperidin-4-yl]-2-cyclopentyl-2-hydroxy-2-phenylacetamide The title compound was prepared in the same manner as described in Step 4 of Example 1 using N-(piperidin-4-yl)-2-cyclopentyl-2-hydroxy-2-phenylacetamide. Its NMR and MS spectra are identical with those of the compound obtained in Example 16.

Example 28

(2R)-N-[1-(4-Methyl-3-pentenyl)piperidin-4-yl]-2-cyclopentyl-2-hydroxy-2-phenylacetamide fumarate Step 1. Synthesis of (2R)-2-cyclopentyl-2-hydroxy-2-phenylacetic acid Step 1-1. Optical resolution of 2-cyclopentyl-2-hydroxy-2-phenylacetic acid 8.7 g of the 2-cyclopentyl-2-hydroxy-2-phenylacetic acid obtained in Step 1 of Example 27 and 11.6 g of cinchonidine were dissolved in 1.5 liters of toluene by the application of heat, and this solution was cooled to room temperature over a period of about 4 hours. The white needle-like crystals which separated out were dissolved again in 900 ml of toluene, and this solution was cooled to room temperature over a period of about 4 hours. The white needle-like crystals which separated out were collected by filtration to obtain 8.0 g of the cinchonidine salt of (2R)-2-cyclopentyl-2-hydroxy-2-phenylacetic acid. This was dissolved in a mixture of diethyl ether and 1N hydrochloric acid. The organic layer was washed with water and a saturated aqueous solution of sodium chloride and then dried over anhydrous magnesium sulfate. Thereafter, the solvent was distilled off under reduced pressure to obtain 3.0 g of the title compound.

Step 1-2. Asymmetric synthesis of (2R)-2-cyclopentyl-2-hydroxy-2-phenylacetic acid 1 ml of a solution of 1.5M lithium diisopropylamide in hexane was added dropwise to a solution of 293 mg of (2S,5S)-2-(t-butyl)-5-phenyl-1,3-dioxolan-4-one in 10 ml of tetrahydrofuran at −78° C., and this solution was stirred for 30 minutes. After the addition of 0.15 ml of cyclopentenone, the solution was stirred for an additional hour. A solution of 510 mg of N-phenyltrifluoromethanesulfonimide in 5 ml of tetrahydrofuran was added to the reaction mixture, and the resulting mixture was stirred at room temperature overnight. The reaction mixture was poured into a saturated aqueous solution of ammonium chloride and extracted with ethyl acetate. The organic layer was washed with a saturated aqueous solution of sodium chloride and dried over anhydrous magnesium sulfate. After the solvent was distilled off under reduced pressure, the resulting residue was purified by silica gel column chromatography (developing solvent: hexane/ethyl acetate=40/1) to obtain 360 mg of a yellow oily substance. This was dissolved in 4 ml of methanol, and 45 mg of sodium acetate and 15 mg of 10% palladium-carbon were added thereto. This mixture was stirred at room temperature under atmospheric pressure in an atmosphere of hydrogen for 6 hours. After the reaction mixture was filtered through celite, the solvent was distilled off under reduced pressure. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: hexane/ethyl acetate=19/1) to obtain 63 mg of a colorless oily material. This was dissolved in 1 ml of methanol, and 1 ml of a 1N aqueous solution of sodium hydroxide was added thereto. This mixture was stirred at 60° C. for 3 hours. After the methanol was distilled off under reduced pressure, the resulting residue was washed with diethyl ether, made acidic with 1N hydrochloric acid, and then extracted with chloroform. The organic layer was washed with a saturated aqueous solution of sodium chloride and then dried over anhydrous magnesium sulfate. Thereafter, the solvent was distilled off under reduced pressure to obtain 46 mg of the title compound.

It was confirmed by high-performance liquid chromatography using a chiral column [column: DAICEL CHIRALCEL OJ, 0.46 cm (inner diameter)×250 cm] that the compounds obtained in Steps 1-1 and 1-2 were identical. From the viewpoint of synthetic chemistry, the steric configuration at the 2-position of the compound obtained in Step 1-2 was presumed to be R.

Step 2. Synthesis of (2R)-N-[1-(4-methyl-3-pentenyl)piperidin-4-yl]-2-cyclopentyl-2-hydroxy-2-phenylacetamide fumarate The title compound was prepared in the same manner as described in Example 25 using (2R)-2-cyclopentyl-2-hydroxy-2-phenyl acetic acid.

¹H-NMR (CD₃ OD, δ ppm): 1.20–2.14 (12H, m), 1.67 (3H, s), 1.72 (3H, s), 2.37–2.48 (2H, m), 2.97–3.13 (5H, m), 3.42–3.58 (2H, m), 3.80–3.91 (1H, m), 5.04–5.11 (1H, m), 6.71 (2H, s), 7.18–7.33 (3H, m), 7.58–7.63 (2H, m).

Example 29

(2R)-N-{1-[(4S)-4-Methylhexyl]piperidin-4-yl}-2-cyclopentyl-2-hydroxy-2-phenylacetamide hydrochloride The title compound was prepared in the same manner as described in Step 5 of Example 22 using (2R)-2-cyclopentyl-2-hydroxy-2-phenylacetic acid.

¹H-NMR (CD₃ OD, δ ppm): 0.90 (3H, t, J=7.3 Hz), 0.91 (3H, d, J=6.0 Hz), 1.13–2.16 (19H, m), 2.93–3.16 (5H, m), 3.44–3.67 (2H, m), 3.80–3.92 (1H, m), 7.19–7.33 (3H, m), 7.59–7.64 (2H, m).

Example 30

N-[1-(E)-(4-Methyl-3-pentenyl)piperidin-4-yl]-2-cyclopentyl-2-hydroxy-2-phenylacetamide The title compound was prepared in the same manner as described in Step 3 of Example 27 using 4-methyl-2-pentenyl methanesulfonate.

¹H-NMR (CDCl₃, δ ppm): 0.97 (6H, d, J=6.8 Hz), 1.15–2.05 (14H, m), 2.22–2.33 (1H, m), 2.72–2.77 (2H, m), 2.88 (2H, d, J=6.6 Hz), 2.95–3.09 (1H, m), 3.14–3.23 (1H, m), 3.64–3.75 (1H, m), 5.34–5.43 (1H, m), 5.51–5.58 (1H, m), 6.33 (1H, d, J=7.6 Hz), 7.22–7.36 (3H, m), 7.57–7.61 (2H, m).

Low Resolution FAB-MS (m/e, as (C₂₄H₃₆N₂O₂+H)⁺): 385

Example 31

Synthesis of N-[1-(E)-(4-methyl-2-hexenyl)peridin-4-yl]-2-cyclopentyl-2-hydroxy-2-phenylacetamide The title compound was prepared in the same manner as described in Step 3 of Example 27 using (E)-4-methyl-2-hexenyl methanesulfonate.

¹H-NMR (CDCl₃, δ ppm): 0.83 (3H, t, J=7.3 Hz), 0.96 (3H, d, J=6.8 Hz), 1.20–2.06 (18H, m), 2.71–2.77 (2H, m), 2.90 (2H, d, J=6.2 Hz), 2.93–3.08 (1H, m), 3.64–3.74 (1H, m), 5.39–5.43 (2H, m), 6.35 (1H, d, J=7.9 Hz), 7.22–7.36 (3H, m), 7.57–7.61 (2H, m).

Low Resolution FAB-MS (m/e, as (C₂₅H₃₈N₂O₂+H)⁺): 399

Example 32

N-[1-(Cyclohexylmethyl)piperidin-4-yl]-2-cyclopentyl-2-hydroxy-2-phenylacetamide The title compound was prepared in the same manner as described in Step 3 of Example 27 using cyclohexylmethyl p-toluenesulfonate.

¹H-NMR (CDCl₃, δ ppm): 0.73–0.92 (2H, m), 1.03–1.90 (21H, m), 1.92–2.30 (4H, m), 2.12 (2H, d, J=6.9 Hz), 3.61–3.79 (1H, m), 6.32 (1H, br d, J=8.1 Hz), 7.21–7.40 (3H, m), 7.59 (2H, br d, J=7.5 Hz).

Low-resolution FAB-MS (m/e, as (C₂₅H₃₈N₂O₂+H)⁺): 399.

Example 33

N-[1-(Cycloheptylmethyl)piperidin-4-yl]-2-cyclopentyl-2-hydroxy-2-phenylacetamide 34 mg of N-(piperidin-4-yl)-2-cyclopentyl-2-hydroxy-2-phenylacetamide obtained in Step 2 of Example 27, 50 mg of cycloheptanecarbaldehyde and 10 mg of acetic acid were dissolved in tetrahydrofuran. 70 mg of sodium triacetoxyborohydride was added thereto and the resulting mixture was stirred for 17 hours. After the addition of a saturated aqueous solution of sodium bicarbonate, the reaction mixture was extracted with chloroform. The organic layer was washed with a saturated aqueous solution of sodium chloride and then dried over anhydrous sodium sulfate. After the solvent was distilled off under reduced pressure, the resulting residue was purified by preparative thin layer chromatography (Kieselgel™, 60F₂₅₄, Art 5744 (manufactured by E. Merck; developing solvent: chloroform/methanol=10/1) to obtain the title compound.

¹H-NMR (CDCl₃, δ ppm): 1.00–1.91 (25H, m), 1.96–2.19 (4H, m), 2.61–2.84 (2H, m), 2.93–3.11 (1H, m), 3.21 (1H, br s), 3.63–3.80 (1H, m), 6.31 (1H, d, J=7.2 Hz), 7.21–7.41 (3H, m), 7.56–7.68 (2H, m)

Low Resolution FAB-MS (m/e, (C₂₆H₄₀N₂O₂+H)⁺): 413

Example 34

(2R)-N-[1-(Cycloheptylmethyl)piperidin-4-yl]-2-cyclopentyl-2-hydroxy-2-phenylacetamide The title compound was prepared in the same manner as described in Steps 2 to 4 of Example 22 using (2R)-2-cyclopentyl-2-hydroxy-2-phenylacetic acid obtained in Step 1 of Example 28 and cyclopentylmethyl methanesulfonate.

Example 35

(2R)-N-[1-(Cycloheptylmethyl)piperidin-4-yl]-2-cyclopentyl-2-hydroxy-2-phenylacetamide hydrochloride (2R)-N-[1-(Cycloheptylmethyl)piperidin-4-yl]-2-cyclopentyl-2-hydroxy-2-phenylacetamide obtained in Example 34 was dissolved in chloroform and a 4N hydrochloric acid solution in ethyl acetate was added thereto. The solvent was distilled off under reduced pressure and the residue was washed with diethyl ether. The resulting solid was recrystallized from ethanol-diethyl ether to obtain the title compound.

¹H-NMR (CDCl₃, δ ppm): 1.08–1.27 (1H, m), 1.29–2.13 (22H, m), 2.39–2.87 (4H, m), 2.79 (2H, d, J=6.6 Hz), 3.00–3.15 (2H, m), 3.46–3.64 (2H, m), 3.85–4.11 (1H, m), 6.92 (1H, br d, J=8.4 Hz), 7.20–7.40 (3H, m), 7.60 (2H, d, J=7.2 Hz)

Low Resolution FAB-MS (m/e, (C₂₆H₄₀N₂O₂+H)⁺): 413

Example 36

N-[1-(1-Cycloheptenylmethyl)piperidin-4-yl]-2-cyclopentyl-2-hydroxy-2-phenylacetamide The title compound was prepared in the same manner as described in Example 33 using 1-cycloheptenecarbaldehyde.

¹H-NMR (CDCl₃, δ ppm): 1.16–2.13 (21H, m), 2.41–2.54 (2H, m), 2.63–2.72 (2H, m), 2.76 (2H, s), 2.93–3.03 (2H, m), 3.19 (1H, br s), 3.62–3.73 (1H, m), 5.62–5.66 (1H, m), 6.28 (1H, d, J=7.6 Hz), 7.22–7.34 (3H, m), 7.57–7.60 (2H, m)

Low Resolution FAB-MS (m/e, (C₂₆H₃₈N₂O₂+H)⁺): 411

Example 37

N-[1-(1-Cyclohexenylmethyl)piperidin-4-yl]-2-cyclopentyl-2-hydroxy-2-phenylacetamide The title compound was prepared in the same manner as described in Example 33 using 1-cyclohexenecarbaldehyde.

¹H-NMR (CDCl₃, δ ppm): 1.10–2.12 (22H, m), 2.64–2.90 (2H, m), 2.85 (2H, br s), 2.95–3.09 (1H, m), 3.15 (1H, br s), 3.60–3.81 (1H, m), 5.55–5.62 (1H, m), 6.36 (1H, d, J=9.0 Hz), 7.21–7.39 (3H, m), 7.60 (2H, br d, J=7.5 Hz)

Low Resolution FAB-MS (m/e, (C₂₅H₃₆N₂O₂+H)⁺): 397

Example 38

N-[1-(Cyclopentylmethyl)piperidin-4-yl]-2-cyclopentyl-2-hydroxy-2-phenylacetamide The title compound was prepared in the same manner as described in Step 3 of Example 27 using cyclopentylmethyl methanesulfonate.

¹H-NMR (CDCl₃, δ ppm): 1.10–1.31 (2H, m), 1.35–1.90 (18H, m), 1.96–2.15 (3H, m), 2.25 (2H, d, J=7.3 Hz), 2.78 (2H, d, J=11.6 Hz), 2.93–3.10 (1H, m), 3.27 (1H, br s), 3.62–3.75 (1H, m), 6.35 (1H, J=8.3 Hz), 7.22–7.41 (3H, m), 7.59 (2H, d, J=6.7 Hz)

Low Resolution FAB-MS (m/e, (C₂₄H₃₆N₂O₂+H)⁺): 385

Example 39

N-[1-(1-Cyclopentenylmethyl)piperidin-4-yl]-2-cyclopentyl-2-hydroxy-2-phenylacetamide The title compound was prepared in the same manner as described in Step 3 of Example 27 using 1-cyclopentenylmethyl methanesulfonate.

¹H-NMR (CDCl₃, δ ppm): 1.36–1.73 (10H, m), 1.75–1.94 (4H, m), 1.96–2.10 (2H, m), 2.22–2.38 (4H, m), 2.70–2.80 (2H, m), 3.00 (2H, s), 3.01–3.18 (2H, m), 3.63–3.77 (1H, m), 5.53 (1H, s), 6.36 (1H, d, J=8.1 Hz), 7.24–7.36 (3H, m), 7.60 (1H, dd, J=8.5, 1.2 Hz)

Low Resolution FAB-MS (m/e, (C₂₄H₃₄N₂O₂+H)⁺): 383

Example 40

N-[1-(3-Methyl-1-cyclohexenylmethyl)piperidin-4-yl]-2-cyclopentyl-2-hydroxy-2-phenylacetamide The title compound was prepared in the same manner as described in Step 3 of Example 27 using 3-methyl-1-cyclohexenylmethyl methanesulfonate.

¹H-NMR (CDCl₃, δ ppm): 0.95 (3H, d, J=6.9 Hz), 1.00–2.21 (21H, m), 2.60–2.89 (4H, m), 2.94–3.09 (1H, m), 3.15 (1H, br s), 3.61–3.80 (1H, m), 5.36–5.44 (1H, m), 6.21–6.39 (1H, m), 7.20–7.40 (3H, m), 7.55–7.63 (2H, m)

Low Resolution FAB-MS (m/e, (C₂₆H₃₈N₂O₂+H)⁺): 411

Example 41

N-[1-(4-Methyl-1-cyclohexenylmethyl)piperidin-4-yl]-2-cyclopentyl-2-hydroxy-2-phenylacetamide The title compound was prepared in the same manner as described in Step 3 of Example 27 using 4-methyl-1-cyclohexenylmethyl methanesulfonate.

¹H-NMR (CDCl₃, δ ppm): 0.95 (3H, d, J=6.0 Hz), 1.04–1.30 (2H, m), 1.31–2.17 (19H, m), 2.59–2.89 (4H, m), 2.95–3.10 (1H, m), 3.17 (1H, s), 3.61–3.79 (1H, m), 5.49–5.58 (1H, m), 6.29 (1H, d, J=7.2 Hz), 7.21–7.40 (3H, m), 7.56–7.65 (2H, m)

Low Resolution FAB-MS (m/e, (C₂₆H₃₈N₂O₂+H)⁺): 411

Example 42

N-[1-(2-Cyclohexenylmethyl)piperidin-4-yl]-2-cyclopentyl-2-hydroxy-2-phenylacetamide The title compound was prepared in the same manner as described in Step 3 of Example 27 using 2-cyclohexenylmethyl 4-toluenesulfonate.

¹H-NMR (CDCl₃, δ ppm): 0.80–0.96 (1H, m), 1.05–2.39 (22H, m), 2.69–2.86 (2H, m), 2.94–3.10 (1H, m), 3.16 (1H, br s), 3.61–3.80 (1H, m), 5.57–5.65 (1H, m), 5.67–5.77 (1H, m), 6.27–6.49 (1H, m), 7.22–7.42 (3H, m), 7.56–7.65 (2H, m)

Example 43

N-(1-Pentylpiperidin-4-yl)-2-cyclopentyl-2-hydroxy-2-phenylacetamide

The title compound was prepared in the same manner as described in Step 3 of Example 27 using 1-pentyl 4-toluenesulfonate.

¹H-NMR (CDCl₃, δ ppm): 0.88 (3H, t, J=6.9 Hz), 1.10–1.76 (16H, m), 1.78–1.94 (2H, m), 2.02–2.19 (2H, m), 2.28–2.40 (2H, m), 2.75–2.92 (2H, m), 2.95–3.20 (2H, m), 3.62–3.80 (1H, m), 6.37 (1H, d, J=8.1 Hz), 7.20–7.39 (3H, m), 7.59 (2H, dd, J=8.4, 1.2 Hz)

Example 44

N-[1-(trans-3-Methylcyclohexylmethyl)piperidin-4-yl]-2-cyclopentyl-2-hydroxy-2-phenylacetamide The title compound was prepared in the same manner as described in Step 3 of Example 27 using trans-3-methylcyclohexylmethyl 4-toluenesulfonate.

¹H-NMR (CDCl₃, δ ppm): 0.89 (3H, d, J=6.9 Hz), 1.02–1.90 (22H, m), 1.97–2.29 (4H, m), 2.64–2.84 (2H, m), 2.94–3.10 (1H, m), 3.17 (1H, br s), 3.60–3.79 (1H, m), 6.31 (1H, d, J=8.1 Hz), 7.21–7.40 (3H, m), 7.57–7.66 (2H, m)

Low Resolution FAB-MS (m/e, (C₂₆H₄₀N₂O₂+H)⁺): 413

Example 45

N-[1-(cis-3-Methylcyclohexylmethyl)piperidin-4-yl]-2-cyclopentyl-2-hydroxy-2-phenylacetamide The title compound was prepared in the same manner as described in Step 3 of Example 27 using cis-3-methylcyclohexylmethyl 4-toluenesulfonate.

¹H-NMR (CDCl₃, δ ppm): 0.42–0.58 (1H, m), 0.64–0.95 (2H, m), 0.87 (3H, d, J=6.6 Hz), 1.12–1.90 (19H, m), 1.95–2.18 (4H, m), 2.61–2.81 (2H, m), 2.95–3.10 (1H, m), 3.18 (1H, br s), 3.60–3.77 (1H, m), 6.29 (1H, d, J=8.4 Hz), 7.20–7.49 (3H, m), 7.55–7.63 (2H, m)

Low Resolution FAB-MS (m/e, (C₂₆H₄₀N₂O₂+H)⁺): 413

Example 46

N-[1-(3-Methyl-1-cyclopentenylmethyl)piperidin-4-yl]-2-cyclopentyl-2-hydroxy-2-phenylacetamide The title compound was prepared in the same manner as described in Step 3 of Example 27 using 3-methyl-1-cyclopentenylmethyl 4-toluenesulfonate.

¹H-NMR (CDCl₃, δ ppm): 0.99 (3H, d, J=2.9 Hz), 1.13–1.93 (14H, m), 2.00–2.16 (3H, m), 2.20–2.38 (2H, m), 2.63–2.80 (3H, m), 2.98 (2H, s), 2.96–3.08 (1H, m), 3.08–3.30 (1H, m), 3.62–3.77 (1H, m), 5.44 (1H, s), 6.37 (1H, d, J=8.2 Hz), 7.26–7.36 (3H, m), 7.60 (2H, d, J=7.1 Hz)

Low Resolution FAB-MS (m/e, (C₂₅H₃₆N₂O₂+H)⁺): 397

Example 47

N-[1-(4-Methyl-3-pentenyl)piperidin-4-yl]-2-cyclopentyl-2-hydroxy-2-(2-thienyl)acetamide Step 1. Synthesis of 2-cyclopentyl-2-hydroxy-2-(2-thienyl) acetic acid A solution of cyclopentylmagnesium chloride in diethyl ether was added dropwise to a solution of 5.00 g of 2-thienylglyoxylic acid in tetrahydrofuran at −40° C. over a period of 30 minutes. This mixture was stirred at the same temperature for 25 minutes and a 1N hydrochloric acid was added thereto. The organic layer was separated, made alkaline with an aqueous solution of sodium bicarbonate, and then washed with diethyl ether. The basic aqueous layer was made acidic with 1N hydrochloric acid and extracted with diethyl ether. The organic layer was washed with water and a saturated aqueous solution of sodium chloride and then dried over anhydrous sodium sulfate. After the solvent was distilled off under reduced pressure, the resulting residue was suspended in diethyl ether and the solid matter was removed by filtration. The solvent was distilled off under reduced pressure to obtain the tile compound.

Step 2. Synthesis of N-[1-(4-methyl-3-pentenyl)piperidin-4-yl]-2-cyclopentyl-2-hydroxy-2-(2-thienyl)acetamide The title compound was prepared in the same manner as described in Step 2 of Example 25 using 2-cyclopentyl-2-hydroxy-2-(2-thienyl)acetic acid.

$^1$H-NMR (CDCl$_3$, δ ppm): 1.36–1.82 (20H, m), 1.87 (2H, m), 2.21 (4H, m), 2.44 (2H, m), 2.81 (1H, m), 2.94 (2H, m), 3.78 (1H, m), 5.04 (1H, m), 6.43 (1H, d, J=7.8 Hz), 6.95 (1H, dd, J=5.2, 3.6 Hz), 7.08 (1H, dd, J=3.6, 0.7 Hz), 7.22 (1H, dd, J=5.0, 0.7 Hz)

Low Resolution FAB-MS (m/e, (C$_{22}$H$_{34}$ N$_2$O$_2$S+H)$^+$): 391

Example 48

N-[1-(4-Methyl-3-pentenyl)piperidin-4-yl]-2-cyclopentyl-2-hydroxy-2-(3-thienyl)acetamide The title compound was prepared in the same manner as described in Example 47 using 3-thienylglyoxylic acid.

$^1$H-NMR (CDCl$_3$, δ ppm): 1.37–1.77 (18H, m), 1.80–1.98 (2H, m), 2.08–2.24 (4H, m), 2.30–2.42 (4H, m), 2.77–2.92 (2H, m), 3.66–3.80 (1H, m), 5.02–5.10 (1H, m), 6.35 (1H, d, J=7.9 Hz), 7.19 (1H, dd, J=5.0, 1.4 Hz), 7.28 (1H, dd, J=5.0, 3.0 Hz), 7.30 (1H, dd, J=3.0, 1.4 Hz)

Low Resolution FAB-MS (m/e, (C$_{22}$H$_{34}$N$_2$O$_2$S+H)$^+$): 391

Example 49

N-[1-(4-Methyl-3-pentenyl)piperidin-4-yl]-2-cyclopentyl-2-(3-furyl)-2-hydroxyacetamide Step 1. Synthesis of ethyl 3-furylglyoxylate A solution of n-butyllithium in hexane was added dropwise to a solution of 1 ml of 3-bromofuran in 6 ml of diethyl ether at −78° C., and this mixture was stirred at the same temperature for 15 minutes. A solution of 22 ml of diethyl oxalate in 9 ml of diethyl ether was added dropwise thereto and the resulting mixture was stirred at −78° C. for 30 minutes. After the addition of 14 ml of 1N hydrochloric acid at the same temperature, the reaction mixture was gradually warmed to room temperature. The reaction mixture was extracted with diethyl ether. The organic layer was washed with water and a saturated aqueous solution of sodium chloride and then dried over anhydrous sodium sulfate. After the solvent was distilled off under reduced pressure, the resulting residue was purified by silica gel column chromatography (developing solvent: hexane/ethyl acetate=10/1) to obtain the title compound.

Step 2. Synthesis of 2-cyclopentyl-2-(3-furyl)-2-hydroxyacetic acid

The title compound was prepared in the same manner as described in Step 1 of Example 27 using ethyl 3-furylglyoxylate.

Step 3. Synthesis of N-[1-(4-methyl-3-pentenyl)piperidin-4-yl]-2-cyclopentyl-2-(3-furyl)-2-hydroxyacetamide The title compound was prepared in the same manner as described in Step 2 of Example 47 using 2-cyclopentyl-2-(3-furyl)-2-hydroxyacetic acid.

$^1$H-NMR (CDCl$_3$, δ ppm): 1.34–1.84 (16H, m), 1.83–1.95 (2H, m), 2.09–2.25 (4H, m), 2.33–2.40 (2H, m), 2.60–2.74 (1H, m), 2.83–2.92 (2H, m), 2.90–3.30 (1H, m), 3.70–3.84 (1H, m), 5.03–5.11 (1H, m), 6.42 (1H, d, J=7.2 Hz), 6.44 (1H, dd, J=2.7, 1.8 Hz), 7.33 (1H, d, J=1.8 Hz), 7.46 (1H, d, J=2.5 Hz)

Low Resolution FAB-MS (m/e, (C$_{22}$H$_{34}$N$_2$O$_3$+H)$^+$): 375

Example 50

N-[1-(4-Methyl-3-pentenyl)piperidin-4-yl]-2-cyclopentyl-2-(2-furyl)-2-hydroxyacetamide The title compound was prepared in the same manner as described in Example 49 using furan.

$^1$H-NMR (CDCl$_3$, δ ppm): 1.35–1.77 (16H, m), 1.78–1.90 (1H, m), 1.91–2.02 (1H, m), 2.05–2.23 (4H, m), 2.30–2.40 (2H, m), 2.60–2.70 (1H, m), 2.72–2.92 (2H, m), 3.70–3.83 (1H, m), 3.95–4.15 (1H, m), 5.03–5.12 (1H, m), 6.20 (1H, d, J=7.5 Hz), 6.36 (1H, d, J=3.3 Hz), 6.39 (1H, d, J=3.3 Hz), 7.38 (1H, s)

Low Resolution FAB-MS (m/e, (C$_{22}$H$_{34}$ N$_2$O$_3$+H)$^+$): 375

Example 51

N-[1-(4-Methyl-3-pentenyl)piperidin-4-yl]-2-cyclopentyl-2-hydroxy-2-(2-thiazolyl)acetamide The title compound was prepared in the same manner as described in Example 49 using thiazole.

$^1$H-NMR (CDCl$_3$, δ ppm): 1.40–2.08 (18H, m), 2.10–2.27 (4H, m), 2.27–2.40 (2H, m), 2.61–2.91 (3H, m), 3.62–3.85 (1H, m), 5.00–5.12 (2H, m), 7.29 (1H, d, J=3.2 Hz), 7.32–7.42 (1H, m), 7.72 (1H, d, J=3.2 Hz)

Low Resolution FAB-MS (m/e, (C$_{21}$H$_{33}$N$_2$O$_2$S+H)$^+$): 392

Example 52

N-[1-(4-Methyl-3-pentenyl)piperidin-4-yl]-2-cyclopentyl-2-hydroxy-2-(2-pyridyl)acetamide The title compound was prepared in the same manner as described in Example 49 using 2-bromopyridine.

$^1$H-NMR (CDCl$_3$, δ ppm): 1.30–2.00 (18H, m), 2.03–2.23 (4H, m), 2.28–2.37 (2H, m), 2.74–2.98 (3H, m), 3.62–3.80 (1H, m), 5.02–5.10 (1H, m), 6.23 (1H, s), 7.23 (1H, dd, J=5.0, 7.5 Hz), 7.46 (1H, d, J=8.5 Hz), 7.73 (1H, dd, J=9.2, 8.1 Hz), 7.93 (1H, d, J=9.1 Hz), 8.44 (1H, d, J=4.2 Hz)

Low Resolution FAB-MS (m/e, (C$_{23}$H$_{35}$N$_3$O$_2$+H)$^+$): 386

Example 53

N-[1-(4-Methyl-3-pentenyl)piperidin-4-yl]-2-cyclopentyl-2-(3-fluorophenyl)-2-hydroxyacetamide The title compound was prepared in the same manner as described in Steps 2 to 3 of Example 49 using methyl 3-fluorophenylglyoxylate.

$^1$H-NMR (CDCl$_3$, δ ppm): 1.10–1.76 (14H, m), 1.77–1.95 (4H, m), 2.00–2.20 (4H, m), 2.27–2.36 (2H, m), 2.70–2.90 (2H, m), 2.92–3.14 (2H, m), 3.62–3.78 (1H, m), 5.02–5.11 (1H, m), 6.39 (1H, d, J=8.2 Hz), 6.92–7.00 (1H, m), 7.25–7.41 (3H, m)

Low Resolution FAB-MS (m/e, $(C_{24}H_{35}FN_2O_2+H)^+$): 403

Example 54

N-[1-(4-Methyl-3-pentenyl)piperidin-4-yl]-2-cyclopentyl-2-(2-fluorophenyl)-2-hydroxyacetamide The title compound was prepared in the same manner as described in Example 53 using methyl 2-fluorophenylglyoxlate.

$^1$H-NMR (CDCl$_3$, δ ppm): 1.24–1.77 (10H, m), 1.77–1.88 (2H, m), 1.92–2.04 (2H, m), 2.10–2.28 (4H, m), 2.32–2.42 (2H, m), 2.74–3.06 (3H, m), 3.72–3.86 (1H, m), 4.51 (1H, br s), 5.07 (1H, tt, J=1.4, 7.0 Hz), 6.44 (1H, br t, J=7.3 Hz), 6.98–7.04 (1H, m), 7.15 (1H, dt, J=1.3, 7.9 Hz), 7.22–7.32 (1H, m), 7.76 (1H, dt, J=1.3, 7.9 Hz)

Low Resolution FAB-MS (m/e, $(C_{24}H_{35}FN_2O_2+H)^+$): 403

Example 55

N-[1-(4-Methyl-3-pentenyl)piperidin-4-yl]-2-cyclopentyl-2-(4-fluorophenyl)-2-hydroxyacetamide fumarate The title compound was prepared in the same manner as described in Example 53 and Step 3 of Example 25 using methyl 4-fluorophenylglyoxylate.

$^1$H-NMR (CDCl$_3$, δ ppm): 1.16–2.00 (13H, m), 1.67 (3H, s), 1.72 (3H, s), 2.00–2.14 (1H, m), 2.34–2.46 (2H, m), 2.88–3.14 (5H, m), 3.40–3.56 (2H, m), 3.77–3.90 (1H, m), 5.02–5.11 (1H, m), 6.69 (2H, s), 6.97–7.06 (2H, m), 7.56–7.66 (2H, m)

Low Resolution FAB-MS (m/e, $(C_{24}H_{35}FN_2O_2+H)^+$): 403

Example 56

N-[1-(4-Methyl-3-pentenyl)piperidin-4-yl]-2-(2-imidazolyl)-2-cyclopentyl-2-hydroxyacetamide Step 1. Synthesis of N-[2-(trimethylsilyl)ethoxymethyl]imidazole 2.23 g of sodium hydride was added to a solution of 2.93 g of imidazole in tetrahydrofuran under cooling with ice, and this mixture was stirred for 25 minutes. 7.5 ml of chloromethyl 2-(trimethylsilyl)ethyl ether was added thereto and the resulting mixture was stirred at room temperature overnight. The reaction mixture was mixed with water and extracted with chloroform. The organic layer was dried over anhydrous magnesium sulfate. After the solvent was distilled off under reduced pressure, the resulting residue was purified by silica gel column chromatography (developing solvent: chloroform / methanol=40/1) to obtain 8.02 g of the title compound.

Step 2. Synthesis of N-[1-(4-ethyl-3-pentenyl)piperidin-4-yl]-2-cyclopentyl-2-hydroxy-2-{[2-(trimethylsilyl)ethoxymethyl]imidazol-2-yl}acetamide The title compound was prepared in the same manner as described in Example 49 using N-[2-(trimethylsilyl)ethoxymethyl]imidazole.

Step 3. Synthesis of N-[1-(4-methyl-3-pentenyl)piperidin-4-yl]-2-(2-imidazolyl)-2-cyclopentyl-2-hydroxyacetamide 0.3 ml of a 1N tetrabutylammonium fluoride solution in tetrahydrofuran was added to a solution of 44 mg of N-[1-(4-methyl-3-pentenyl)piperidin-4-yl]-2-cyclopentyl-2-hydroxy-2-{[2-(trimethylsilyl)ethoxymethyl]imidazol-2-yl}acetamide in 2 ml of tetrahydrofuran at 60° C., and this mixture was stirred at the same temperature for 5 hours. The reaction mixture was mixed with a saturated aqueous solution of sodium bicarbonate and extracted with diethyl ether. The organic layer was washed with water and a saturated aqueous solution sodium chloride and then dried over anhydrous magnesium sulfate. After the solvent was distilled off under reduced pressure, the resulting residue was purified by preparative thin layer chromatography [Kieselgel™ 60F$_{254}$, Art 5744 (manufactured by E. Merck); developing solvent: chloroform/methanol=7/1] to obtain 14 mg of the title compound.

$^1$H-NMR (CDCl$_3$, δ ppm): 1.17–1.98 (12H, m), 1.61 (3H, m), 1.69 (3H, m), 2.06–2.27 (4H, m), 2.28–2.40 (2H, m), 2.57–2.91 (3H, m), 3.68–3.81 (1H, m), 4.73 (1H, br s), 5.03–5.13 (1H, m), 6.91–7.03 (2H, m), 7.40–7.59 (1H, m), 9.57–9.87 (1H, m)

Example 57

N-[1-(4-Methyl-3-pentenyl)piperidin-4-yl]-2-cyclopentyl-2-hydroxy-2-(5-thiazolyl)acetamide The title compound was prepared in the same manner as described in Steps 2 to 3 of Example 49 using ethyl 5-thiazolylglyoxylate.

$^1$H-NMR (CDCl$_3$, δ ppm): 1.10–1.71 (10H, m), 1.68 (3H, s), 1.69 (3H, s), 1.80–1.86 (1H, m), 1.92–1.98 (1H, m), 2.11–2.22 (4H, m), 2.31–2.37 (2H, m), 2.69–2.85 (3H, m), 3.70–3.81 (1H, m), 4.79 (1H, s), 5.05–5.10 (1H, m), 7.45 (1H, d, J=7.9 Hz), 7.49 (1H, d, J=2.2 Hz), 8.72 (1H, d, J=2.2 Hz)

Low Resolution FAB-MS (m/e, $(C_{21}H_{33}N_3O_2S+H)^+$): 392

Example 58

N-[1-(4-Methyl-3-pentenyl)piperidin-4-yl]-2-cyclopentyl-2-hydroxy-2-(2-pyrrolyl)acetamide Step 1. Synthesis of ethyl 2-pyrrolylglyoxylate 1.1 g of pyrrole and 1.5 g of pyridine were dissolved in 30 ml of 1,2-dichloroethane and 2.2 ml of ethyl chlorooxalate was added thereto. This mixture was stirred at room temperature for 17 hours. The reaction mixture was mixed with a saturated aqueous solution of ammonium chloride and extracted with diethyl ether. The organic layer was washed with a saturated aqueous solution of sodium chloride and then dried over anhydrous sodium sulfate. After the solvent was distilled off under reduced pressure, the resulting residue was purified by silica gel column chromatography (developing solvent: hexane/ethyl acetate=4/1) to obtain 2.1 g of the title compound.

Step 2. Synthesis of N-[1-(4-methyl-3-pentenyl)piperidin-4-yl]-(2-pyrrolyl)glyoxamide 2.1 g of ethyl 2-pyrrolyglyoxylate was dissolved in a mixture of 10 ml of tetrahydrofuran and 5 ml of water. 1.9 g of lithium hydroxide monohydrate was added thereto and this mixture was stirred at 50° C. for an hour. The reaction mixture was extracted with a saturated aqueous solution of sodium bicarbonate, and the aqueous layer was made acidic with 1N hydrochloric acid and extracted with diethyl ether. The organic layer was washed with a saturated aqueous solution of sodium chloride and then dried over anhydrous sodium sulfate. After the solvent was distilled off under reduced pressure, the resulting residue was dissolved in 10 ml of N,N-dimethylformamide. 700 mg of 1,1'-carbonyldiimidazole was added thereto and the resulting mixture was stirred at room temperature for 2 hours. 990 mg of 4-amino-1-(4-methyl-3-pentenyl)piperidine dihydrochloride, 48 mg of 4-dimethylaminopyridine and 1.5 ml of triethylamine were added thereto and the resulting mixture was stirred at room temperature for 2 days. The reaction mixture was mixed with a saturated aqueous solution of sodium bicarbonate and extracted with diethyl ether. The organic layer was washed with a saturated aqueous solution of sodium hydrochloride and then dried over anhydrous sodium sulfate. After the solvent was distilled off under reduced pressure, the resulting residue was purified by silica gel column chromatography (developing solvent: chloroform/methanol=19/1) to obtain 570 mg of the title compound.

Step 3. N-[1-(4-Methyl-3-pentenyl)piperidin-4-yl]-2-cyclopentyl-2-hydroxy-(2-pyrrolyl)acetamide A solution of cyclopentylmagnesium chloride in diethyl ether was added dropwise to a solution of 540 mg of N-[1-(4-methyl-3-pentenyl)piperidin-4-yl]-(2-pyrrolyl) glyoxamide and 280 mg of lithium perchlorate in 2 ml of tetrahydrofuran under cooling with ice. This mixture was stirred at the same temperature for 40 minutes. The reaction mixture was mixed with a saturated aqueous solution of ammonium chloride and extracted with diethyl ether. The organic layer was washed with a saturated aqueous solution of sodium chloride and then dried over anhydrous magnesium sulfate. After the solvent was distilled off under reduced pressure, the resulting residue was purified by silica gel column chromatography (developing solvent: chloroform/methanol=15/1) to obtain 570 mg of the title compound.

$^1$H-NMR (CDCl$_3$, δ ppm): 1.33–1.67 (10H, m), 1.61 (3H, s), 1.68 (3H, s), 1.81–1.89 (2H, m), 2.03–2.17 (4H, m), 2.27–2.32 (2H, m), 2.49–2.60 (1H, m), 2.72–2.81 (2H, m), 3.45 (1H, br s), 3.64–3.78 (1H, m), 5.03–5.09 (1H, m), 6.08–6.16 (2H, m), 6.42 (1H, d, J=7.9 Hz), 6.70–6.72 (1H, m), 9.04 (1H, br s)

Low Resolution FAB-MS (m/e, (C$_{22}$H$_{35}$N$_3$O$_2$+H)): 374

Example 59

N-[1-(4-Methyl-3-pentenyl)piperidin-4-yl]-2-cyclopentyl-2-hydroxy-2-(4-pyrimidinyl)acetamide Step 1. Synthesis of ethyl 2-(5-bromo-4-pyrimidinyl)acetate 11.6 ml of a 1.5M lithium diisopropylamide solution in hexane was added dropwise to a solution of 2.1 g of ethyl acetate in 80 ml of tetrahydrofuran at −78° C., and this mixture was stirred at the same temperature for an hour. A solution of 3.35 g of 5-bromopyrimidine in 20 ml of tetrahydrofuran was added dropwise to the reaction mixture and the resulting mixture was gradually warmed to room temperature with stirring over a period of 3 hours. The reaction mixture was mixed with a saturated aqueous solution of ammonium chloride and extracted with ethyl acetate. The organic layer was washed with a saturated aqueous solution of sodium chloride and then dried over anhydrous magnesium sulfate. After the solvent was distilled off under reduced pressure, the resulting residue was dissolved in 200 ml of chloroform, mixed with 15 g of manganese dioxide, and stirred at room temperature for 24 hours. The reaction mixture was filtered and the filtrate was condensed under reduced pressure. The resulting residue was purified by silica gel column chromatography (developing solvent: hexane/ethyl acetate=20/1-5/1) to obtain 3.6 g of the title compound.

Step 2. Synthesis of ethyl (4-pyrimidinyl)glyoxalate

A solution of 2 g of ethyl 2-(5-bromo-4-pyrimidinyl)acetate, 1.74 g of N-bromosuccinimide and 100 mg of α,α'-azobisisobutyronitrile in 50 ml of carbon tetrachloride was stirred at 85° C. for 2 hours. The reaction mixture was cooled to room temperature and filtered. The filtrate was condensed under reduced pressure and the resulting residue was dissolved in 30 ml of acetonitrile. This solution was added dropwise to a solution of 4.8 g of pyridine N-oxide and 9.3 g of silver nitrate in 100 ml of acetonitrile under cooling with ice, and the solution was warmed to room temperature and stirred for 20 hours. The reaction mixture was mixed with 4 ml of triethylamine, stirred for an hour, diluted with ethyl acetate, and filtered. The filtrate was condensed under reduced pressure and the resulting residue was dissolved in chloroform. This solution was washed with a saturated aqueous solution of sodium bicarbonate and a saturated aqueous solution of sodium chloride and then dried over anhydrous magnesium sulfate. After the solvent was distilled off under reduced pressure, the resulting residue was purified by silica gel column chromatography (developing solvent: hexane/ethyl acetate=4/1-2/1) to obtain 800 mg of a white solid. A solution of 350 mg of this solid, 380 mg of sodium bicarbonate and 90 mg of 10% palladium-carbon in 15 ml of ethanol was stirred under an atmosphere of hydrogen at atmospheric pressure and room temperature for 2 hours. The reaction mixture was filtered with celite and the ethanol was distilled off under reduced pressure. The resulting residue was purified by preparative thin layer chromatography [Kieselgel™ 60F$_{254}$, Art 5744 (manufactured by E. Merck); developing solvent: hexane/ethyl acetate=12/1] to obtain 110 mg of the title compound.

Step 3. Synthesis of ethyl 2-cyclopentyl-2-hydroxy-2-(4-pyrimidinyl)acetate

The title compound was prepared in the same manner as described using ethyl (4-pyrimidinyl)glyoxylate.

Step 4. Synthesis of N-[1-(4-methyl-3-pentenyl)piperidin-4-yl]-2-cyclopentyl-2-hydroxy-2-(4-pyrimidinyl)acetamide 0.65 ml of a 1M trimethylaluminum solution in hexane was added to a solution of 85 mg of 4-amino-1-(4-methyl-pentenyl)piperidine dihydrochloride in 5 ml of toluene under cooling with ice, and this mixture was stirred at the same temperature for 2 hours. A solution of 29 mg of ethyl 2-cyclopentyl-2-hydroxy-2-(4-pyrimidinyl)acetate in 3 ml of toluene was added to the reaction mixture. The resulting mixture was stirred at 100° C. for 18 hours, mixed with 1N hydrochloric acid under cooling with ice, made alkaline with a saturated aqueous solution of sodium bicarbonate, and extracted with chloroform. The organic layer was washed with a saturated aqueous solution of sodium chloride and then dried over anhydrous magnesium sulfate. After the solvent was distilled off, the resulting residue was purified by preparative thin layer chromatography [Kieselgel™ 60F$_{254}$, Art 5744 (manufactured by E. 35 Merck); developing solvent: chloroform/methanol=9/1] to obtain 6 mg of the title compound.

$^1$H-NMR (CDCl$_3$, δ ppm): 0.99–1.98 (12H, m), 1.63 (3H, s), 1.70 (3H, s), 2.08–2.43 (6H, m), 2.74–2.96 (3H, m), 3.65–3.82 (1H, m), 5.04–5.13 (1H, m), 5.60 (1H, s), 7.44 (1H, br d, J=7.8 Hz), 7.96 (1H, br d, J=5.4 Hz), 8.74 (1H, d, J=5.4 Hz), 9.13 (1H, br s)

Low Resolution FAB-MS (m/e, (C$_{22}$H$_{34}$N$_4$O$_2$+H)): 387

Example 60

N-[1-(Cycloheptylmethyl)piperidin-4-yl]-2-cyclopentyl-2-hydroxy-2-(5-thiazolyl)acetamide Step 1. Synthesis of 4-amino-1-(cycloheptylmethyl) piperidine dihydrochloride The title compound was prepared in the same manner as described in Steps 2 to 3 of Example 22 using cycloheptylmethyl methanesulfonate.

Step 2. Synthesis of N-[1-(cycloheptylmethyl)piperidin-4-yl]-2-cyclopentyl-2-hydroxy-2-(5-thiazolyl)acetamide The title compound was prepared in the same manner as described in Step 4 of Example 22 using 2-cyclopentyl-2-hydroxy-2-(5-thiazolyl)acetic acid obtained in Example 57 and 4-amino-1-(cycloheptylmethyl)piperidine dihydrochloride.

$^1$H-NMR (CDCl$_3$, δ ppm): 1.04–1.80 (24H, m), 1.88–1.93 (1H, m), 2.00–2.14 (4H, m), 2.65–2.75 (3H, m), 3.66–3.81 (1H, m), 4.79 (1H, s), 7.42 (1H, d, J=7.6 Hz), 7.49 (1H, d, J=2.2 Hz), 8.72 (1H, d, J=2.2 Hz)

Low Resolution FAB-MS (m/e, (C$_{23}$H$_{37}$N$_3$O$_2$S+H)$^+$): 420

Example 61

N-[1-(Cycloheptylmethyl)piperidin-4-yl]-2-cyclopentyl-2-hydroxy-2-(2-thienyl)acetamide The title compound was prepared in the same manner as described in Step 4 of Example 22 using 2-cyclopentyl-2-hydroxy-2-(5-thienyl)acetic acid obtained in Example 47 and 4-amino-1-(cycloheptylmethyl)piperidine dihydrochloride.

$^1$H-NMR (CDCl$_3$, δ ppm): 1.30–1.80 (22H, m), 1.79–1.90 (2H, m), 1.98–2.17 (4H, m), 2.66–2.89 (4H, m), 3.65–3.78 (1H, m), 3.70–4.08 (1H, m), 6.34 (1H, d, J=7.9 Hz), 6.96 (1H, dd, J=5.0, 3.6 Hz), 7.07 (1H, dd, J=3.6, 1.2 Hz), 7.26 (1H, dd, J=5.0, 1.2 Hz)

Low Resolution FAB-MS (m/e, (C$_{24}$H$_{38}$N$_2$O$_2$S+H)$^+$): 419

Example 62

N-[1-(Cycloheptylmethyl)piperidin-4-yl]-2-(2-furyl)-2-cyclopentyl-2-hydroxyacetamide The title compound was prepared in the same manner as described in Step 4 of Example 22 using 2-cyclopentyl-2-(2-furyl)-2-hydroxyacetic acid obtained in Example 50 and 4-amino-1-(cycloheptylmethyl)piperidine dihydrochloride.

$^1$H-NMR (CDCl$_3$, δppm): 1.32–1.98 (24H, m), 1.98–2.15 (4H, m), 2.57–2.80 (3H, m), 3.69–3.83 (1H, m), 4.14 (1H, s), 6.17 (1H, d, J=7.2 Hz), 6.35 (1H, d, J=3.3 Hz), 6.38 (1H, dd, J=3.3, 0.9 Hz), 7.36 (1H, d, J=0.9 Hz)

Example 63

N-[1-(Cycloheptylmethyl)piperidin-4-yl]-2-cyclopentyl-2-hydroxy-2-(2-thiazolyl)acetamide The title compound was prepared in the same manner as described in Step 4 of Example 22 using 2-cyclopentyl-2-hydroxyl-2-(2-thiazolyl)acetic acid obtained in Example 51 and 4-amino-1-(cycloheptylmethyl)piperidine dihydrochloride.

$^1$H-NMR (CDCl$_3$, δ ppm): 1.00–1.18 (2H, m), 1.19–1.84 (23H, m), 1.85–1.97 (1H, m), 1.98–2.18 (3H, m), 2.60–2.81 (3H, m), 3.66–3.81 (1H, m), 5.05 (1H, s), 7.29 (1H, d, J=3.3 Hz), 7.38 (1H, d, J=7.9 Hz), 7.71 (1H, d, J=3.3 Hz)

Low Resolution FAB-MS (m/e, (C$_{23}$H$_{37}$N$_3$O$_2$S+H)$^+$): 420

Example 64

N-[1-(Cycloheptylmethyl)piperidin-4-yl]-2-cyclopentyl-2-hydroxy-2-(3-thienyl)acetamide The title compound was prepared in the same manner as described in Steps 2 to 3 of Example 58 using ethyl 2-thienylglyoxylate and 4-amino-1-(cycloheptylmethyl)piperidine dihydrochloride.

$^1$H-NMR (CDCl$_3$, δ ppm): 1.01–1.92 (25H, m), 1.96–2.18 (4H, m), 2.62–2.94 (3H, m), 3.21 (1H, br s), 3.64–3.80 (1H, m), 6.31 (1H, br d, J=6.8 Hz), 7.19 (1H, dd, J=5.0, 1.4 Hz), 7.25–7.34 (2H, m)

Example 65

N-[1-(Cycloheptylmethyl)piperidin-4-yl]-2-cyclopentyl-2-hydroxy-2-(2-pyridyl)acetamide The title compound was prepared in the same manner as described in Sept 4 of Example 22 using 2-cyclopentyl-2-hydroxy-2-(2-pyridyl)acetic acid obtained in Example 52 and 4-amino-1-(cycloheptylmethyl)piperidine dihydrochloride.

$^1$H-NMR (CDCl$_3$, δ ppm): 0.96–1.16 (4H, m), 1.32–1.78 (20H, m), 1.86–1.92 (1H, m), 1.98–2.09 (4H, m), 2.67–2.75 (2H, m), 2.86–2.96 (1H, m), 3.62–3.76 (1H, m), 6.21 (1H, br s), 7.21–7.26 (1H, m), 7.45 (1H, d, J=7.9 Hz), 7.69–7.45 (1H, m), 7.94 (1H, d, J=7.8 Hz), 8.43–8.45 (1H, m)

Low Resolution FAB-MS (m/e, (C$_{25}$H$_{39}$N$_3$O$_2$+H)$^+$): 414

Example 66

N-[1-(Cycloheptylmethyl)piperidin-4-yl]-2-(3-fluorophenyl)-2-cyclopentyl-2-hydroxyacetamide The title compound was prepared in the same manner as described in Step 4 of Example 22 using 2-(3-fluorophenyl)-2-cyclopentyl-2-hydroxyacetic acid obtained in Example 53 and 4-amino-1-(cycloheptylmethyl)piperidine dihydrochloride.

$^1$H-NMR (CDCl$_3$, δ ppm): 1.00–1.28 (3H, m), 1.28–1.90 (22H, m), 1.95–2.20 (4H, m), 2.60–2.80 (2H, m), 2.90–3.04 (1H, m), 3.08 (1H, s), 3.62–3.78 (1H, m), 6.34 (1H, d, J=7.4 Hz), 6.90–7.00 (1H, m), 7.24–7.42 (3H, m)

Low Resolution FAB-MS (m/e, (C$_{26}$H$_{39}$FN$_2$O$_2$+H)$^+$): 431

Example 67

N-[1-(Cycloheptylmethyl)piperidin-4-yl]-2-(2-fluorophenyl)-2-cyclopentyl-2-hydroxyacetamide The title compound was prepared in the same manner as described in Step 4 of Example 22 using 2-(2-fluorophenyl)-2-cyclopentyl-2-hydroxyacetic acid obtained in Example 54 and 4-amino-1-(cycloheptylmethyl)piperidine dihydrochloride.

$^1$H-NMR (CDCl$_3$, δ ppm): 1.00–1.15 (2H, m), 1.30–1.82 (22H, m), 1.86–2.12 (5H, m), 2.58–2.75 (2H, m), 2.86–3.01 (1H, m), 3.65–3.80 (1H, m), 4.59–4.62 (1H, m), 6.30–6.46 (1H, m), 6.96–7.08 (1H, m), 7.15 (1H, dt, J=1.3, 7.9 Hz), 7.22–7.31 (1H, m), 7.77 (1H, dt, J=1.3, 7.9 Hz)

Low Resolution FAB-MS (m/e, (C$_{26}$H$_{39}$FN$_2$O$_2$+H)$^+$): 431

Example 68

N-[1-(Cycloheptylmethyl)piperidin-4-yl]-2-cyclopentyl-2-(4-fluorophenyl)-2-hydroxyacetamide The title compound was prepared in the same manner as described in Step 4 of Example 22 using 2-cyclopentyl-2-(4-fluorophenyl)-2-hydroxyacetic acid obtained in Example 55 and 4-amino-1-(cycloheptylmethyl)piperidine dihydrochloride.

$^1$H-NMR (CDCl$_3$, δ ppm): 1.00–1.30 (3H, m), 1.30–1.92 (22H, m), 1.92–2.15 (4H, m), 2.62–2.76 (2H, m), 2.92–3.10

(1H, m), 3.04 (1H, s), 3.60–3.74 (1H, m), 6.33 (1H, d, J=8.4 Hz), 6.96–7.06 (2H, m), 7.54–7.62 (2H, m)

Low Resolution FAB-MS (m/e, $(C_{26}H_{39}FN_2O_2+H)^+$): 431

Example 69

N-[1-(2-Cyclopentylethyl)piperidin-4-yl]-2-cyclopentyl-2-hydroxy-2-phenylacetamide The title compound was prepared in the same manner as described in Step 3 of Example 27 using 2-cyclopentylethyl methanesulfonate.

$^1$H-NMR (CDCl$_3$, δ ppm): 1.03–1.28 (2H, m), 1.42–1.90 (21H, m), 2.03–2.10 (2H, m), 2.29–2.35 (2H, m), 2.78–2.88 (2H, m), 3.00–3.14 (2H, m), 3.68–3.72 (1H, m), 6.33 (1H, d, J=7.6 Hz), 7.23–7.36 (3H, m), 7.57–7.61 (2H, m)

Low Resolution FAB-MS (m/e, $(C_{25}H_{38}N_2O_2+H)^+$): 399

Example 70

N-[1-(Cyclooctylmethyl)piperidin-4-yl]-2-cyclopentyl-2-hydroxy-2-phenylacetamide The title compound was prepared in the same manner as described in Example 33 using cyclooctylcarbaldehyde.

$^1$H-NMR (CDCl$_3$, δ ppm): 1.07–1.25 (1H, m), 1.35–2.17 (25H, m), 2.40–2.84 (6H, m), 2.99–3.16 (1H, m), 3.49–3.64 (2H, m), 3.85–4.01 (1H, m), 6.88 (1H, br d, J=8.4 Hz), 7.21–7.41 (3H, m), 7.59 (2H, br d, J=8.3 Hz)

Example 71

N-[1-(4-Methylpentyl)piperidin-4-yl]-2-cyclopentyl-2-(2-fluorophenyl)-2-hydroxyacetamide hydrochloride The title compound was prepared in the same manner as described in Step 3 of Example 27 and Step 5 of Example 22 using 5-bromo-2-methylpentane.

$^1$H-NMR (CDCl$_3$, δ ppm): 0.92 (6H, d, J=6.6 Hz), 1.20–2.14 (18H, m), 2.93–3.16 (6H, m), 3.50–3.63 (2H, m), 3.79–3.90 (1H, m), 7.20–7.31 (3H, m), 7.60 (2H, d, J=7.3 Hz)

Example 72

N-[1-(trans-4-Methylcyclopentylmethyl)piperidin-4-yl]-2-cyclopentyl-2-(2-fluorophenyl)-2-hydroxyacetamide The title compound was prepared in the same manner as described in Step 3 of Example 27 using trans-4-methylcyclopentylmethyl methanesulfonate.

$^1$H-NMR (CDCl, δ ppm): 0.86 (3H, d, J=6.9 Hz), 1.15–1.98 (22H, m), 1.91–2.02 (2H, m), 2.05 (2H, d, J=7.3 Hz), 2.63–2.71 (2H, m), 2.93–3.06 (1H, m), 3.18 (1H, s), 3.60–3.73 (1H, s), 6.25 (1H, d, J=8.2 Hz), 7.21–7.37 (3H, m), 7.59 (2H, d, J=7.5 Hz)

Low Resolution FAB-MS (m/e, $(C_{26}H_{40}N_2O_2+H)^+$): 413

Example 73

N-[1-(Bicyclo[3.3.0]oct-3-ylmethyl)piperidin-4-yl]-2-cyclopentyl-2-hydroxy-2-phenylacetamide The title compound was prepared in the same manner as described in Example 33 using bicyclo[3.3.0]octanecarbaldehyde.

$^1$H-NMR (CDCl$_3$, δ ppm): 1.02–1.75 (18H, m), 1.86–2.00 (2H, m), 2.01–2.22 (2H, m), 2.23–2.41 (1H, m), 2.43–2.60 (2H, m), 2.95–3.23 (5H, m), 3.50–3.63 (2H, m), 3.77–3.95 (1H, m), 7.18–7.33 (3H, m), 7.56–7.64 (2H, m)

Low Resolution FAB-MS (m/e, $(C_{26}H_{40}N_2O_2+H)^+$): 425

Example 74

N-[1-(Bicyclo[4.1.0]hept-7-ylmethyl)piperidin-4-yl]-2-cyclopentyl-2-hydroxy-2-phenylacetamide The title compound was prepared in the same manner as described in Step 3 of Example 27 using bicyclo[4.1.0]hept-2-ylmethyl 4-toluenesulfonate.

$^1$H-NMR (CDCl$_3$, δ ppm): 0.49–0.59 (1H, m), 0.60–0.72 (2H, m), 1.08–1.38 (4H, m), 1.41–2.00 (16H, m), 2.04–2.24 (2H, m), 2.30 (2H, d, J=6.6 Hz), 2.82–3.18 (4H, m), 3.63–3.81 (1H, m), 6.37 (1H, d, J=8.4 Hz), 7.23–7.40 (3H, m), 7.61 (2H, d, J=7.8 Hz)

Formulation Example 1

| Ingredient | mg per tablet |
| --- | --- |
| Compound of Example 28 | 5.0 |
| Lactose | 103.8 |
| Crystalline cellulose | 20.0 |
| Partially gelatinized starch | 20.0 |
| Magnesium stearate | 1.2 |
| Total | 150.0 |

20.0 g of the compound of Example 28, 415.2 g of lactose, 80 g of crystalline cellulose and 80 g of partially gelatinized starch were blended in a V-type mixer. Then, 4.8 g of magnesium stearate was added and further blending was carried out. The resulting blend was formed into tablets in the usual manner. Thus, there were obtained 3,000 tablets having a diameter of 7.0 mm and a weight of 150 mg.

Formulation Example 2

| Ingredient | mg per tablet |
| --- | --- |
| Tablet of Formulation Example 1 | 150 |
| Hydroxypropylcellulose 2910 | 3.6 |
| Polyethylene glycol 6000 | 0.7 |
| Titanium dioxide | 0.7 |
| Total | 155.0 |

10.8 g of hydroxypropylcellulose 2910 and 2.1 g of polyethylene glycol 6000 were dissolved in 172.5 g of purified water. Then, 2.1 g of titanium dioxide was dispersed therein to prepare a coating fluid. Using a High Coater Mini, 3,000 tablets which had been prepared separately were spray-coated with the coating fluid. Thus, there were obtained film-coated tablets having a weight of 155 mg.

Formulation Example 3

0.1 g of the compound of Example 28 was dissolved in 900 ml of physiological saline, and an additional amount of physiological saline was added to make a total amount of 1,000 ml. The resulting solution was sterilized by filtration through a membrane filter having a pore size of 0.25 μm. Then, 1 ml each of this solution was filled into sterilized ampules to make an inhalational liquid preparation.

Formulation Example 4

10 g of the compound of Example 28 and 70 g of lactose were uniformaly blended. Then, 100 mg each of this powder blend was filled into exclusive powder inhalers to make an inhalational powder preparation (400 μg per inhalation).

Exploitability in Industry

The 1,4-di-substituted piperidine compounds of the present invention have selective antagonistic activity against the muscarinic $M_3$ receptors and can hence be used safely with a minimum of side effects. Accordingly, they are very useful in the treatment or prophylaxis of diseases of the respiratory system, such as asthma, chronic airway obstruction and fibroid lung; diseases of the urinary system accompanied by urination disorders such as pollakiuria, urinary urgency and urinary incontinence; and diseases of the digestive system, such as irritable colon and spasm or hyperanakinesis of the digestive tract.

We claim:

1. A 1,4-di-substituted piperidine the formula [I]

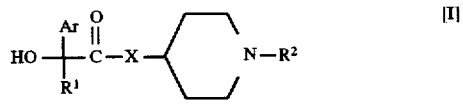

or a pharmaceutically acceptable salt thereof, wherein:

Ar represents a phenyl group or a five- or six-membered heteroaromatic group having one or two hetero atoms selected from the group consisting of an oxygen atom, a sulfur atom and a nitrogen atom in which one or two optional hydrogen atoms on the ring may be replaced by substituent groups selected from the group consisting of a halogen atom and a lower alkyl group;

$R^1$ represents a cycloalkyl group of 3 to 6 carbon atoms or a cycloalkenyl group of 3 to 6 carbon atoms;

$R^2$ represents a saturated or unsaturated aliphatic hydrocarbon radical of 5 to 15 carbon atoms; and X represents O or NH.

2. The compound of claim 1 wherein Ar is a phenyl group or a heteroaromatic group selected from the group consisting of 2-pyrrolyl, 3-pyrrolyl, 2-furyl, 3-furyl, 2-thienyl, 3-thienyl, 3-pyrazolyl, 4-pyrazolyl, 3-isoxazolyl, 5-isoxazolyl, 2-imidazolyl, 4-imidazolyl, 2-oxazolyl, 4-oxazolyl, 5-oxazolyl, 2-thiazolyl, 4-thiazolyl, 5-thiazolyl, 2-pyridyl, 4-pyridyl, 2-pyrimidinyl and 4-pyrimidinyl, in which one or two optional hydrogen atoms on the ring may be replaced by substituent groups selected from the group consisting of a fluorine and a methyl group.

3. The compound of claim 1 wherein R is a cycloalkyl group of 3 to 6 carbon atoms or a cycloalkenyl group of 3 to 6 carbon atoms.

4. The compound of claim 1 wherein X is NH.

5. The compound of claim 1 wherein $R^2$ is said radical of 5 to 15 carbon atoms and is represented by the formula [II]

in which

Q represents a methylene, ethylene, trimethylene or tetramethylene group;

$R^a$ and $R^b$ each represent a hydrogen atom or are combined to form a single bond; and $R^b$, $R^d$ and $R^e$ may be the same or different and each represent a hydrogen atom, a lower alkyl group or a cycloalkyl or cycloalkenyl group of 3 to 8 carbon atoms or $R^b$ or $R^d$, or $R^d$ and $R^e$, are combined to form a cycloalkyl or cycloalkenyl group of 3 to 8 carbon atoms, wherein, Q, $R^b$, $R^d$ and $R^e$ include a total of 3 to 13 carbon atoms.

6. The compound of claim 1 wherein $R^2$ is a linear or branched $C_5$–$C_5$ alkyl, $C_5$–$C_{15}$ alkenyl or $C_5$–$C_{15}$ alkynyl group, a $C_5$–$C_{15}$ cycloalkylalkyl or $C_5$–$C_{15}$ cycloalkylalkenyl group in which an optional hydrogen atom(s) on the cycloalkyl ring may be replaced by a lower alkyl group(s), a $C_5$–$C_{15}$ bicycloalkylalkyl or $C_5$–$C_{15}$ bicycoalkylalkenyl group in which an optional hydrogen atom(s) on the bicycloalkyl ring may be replaced by a lower alkyl group(s), a $C_5$–$C_{15}$ cycloalkenylalkyl or $C_5$–$C_{15}$ cycloalkenylalkenyl group in which an optional hydrogen atom(s) on the cycloalkenyl ring may be replaced by a lower alkyl group(s), a $C_5$–$C_{15}$ bicycloalkenylalkyl or $C_5$–$C_{15}$ bicylcoalkenylalkenyl group in which an optional hydrogen atom(s) on the bicycloalkenyl ring may be replaced by a lower alkyl group(s), or a $C_5$–$C_{15}$ cycloalkylalkynyl or $C_5$–$C_{15}$ cycloalkenylalkynyl group.

7. The compound of claim 1 which is selected from the group consisting of

N-[1-(4-methyl-3-pentenyl)piperidin-4-yl]-2-cyclobutyl-2-hydroxy-2-phenylacetamide, N-(1-hexylpiperidin-4-yl)-2-cyclobutyl-2-hydroxy-2-phenylacetamide, N-{1-[(Z)-3-hexenyl]piperidin-4-yl}-2-cyclobutyl-2-hydroxy-2-phenylacetamide, N-{1-[(E)-3-hexenyl]piperidin-4-yl}-2-cyclobutyl-2-hydroxy-2-phenylacetamide, N-[1-(6-methyl-5-heptenyl)piperidin-4-yl]-2-cyclobutyl-2-hydroxy-2-phenylacetamide, N-[1-(4-methyl-3-pentenyl)piperidin-4-yl]-2-cyclobutyl-2-(4-fluorophenyl)-2-hydroxyacetamide, N-[1-(5-methyl-4-hexenyl)piperidin-4-yl]-2-cyclobutyl-2-hydroxy-2-phenylacetamide, N-[1-(4-methylpentyl)piperidin-4-yl]-2-cyclobutyl-2-hydroxy-2-phenylacetamide, N-[1-(4-methyl-2-pentynyl)piperidin-4-yl]-2-cyclobutyl-2-hydroxy-2-phenylacetamide, N-[1-(5-methyl-3-hexynyl)piperidin-4-yl]-2-cyclobutyl-2-hydroxy-2-phenylacetamide, N-[1-(4-methyl-3-pentenyl)piperidin-4-yl]-2-cyclohexyl-2-hydroxy-2-phenylacetamide, N-{1-[(4S)-4-methylhexyl]piperidin-4-yl}-2-cyclohexyl-2-hydroxy-2-phenylacetamide, N-[1-(4,5-dimethyl-4-hexenyl)piperidin-4-yl]-2-cyclobutyl-2-hydroxy-2-phenylacetamide, N-[1-(4-methyl-3-pentenyl)piperidin-4-yl]-2-cyclopropyl-2-hydroxy-2-phenylacetamide, N-{1-[(4S)-4-methylhexyl]piperidin-4-yl}-2-cyclopropyl-2-hydroxy-2-phenylacetamide, N-[1-(4-methyl-3-pentenyl)piperidin-4-yl]-2-cyclopentyl-2-hydroxy-2-phenylacetamide, N-{1-[(4S)-4-methylhexyl]piperidin-4-yl}-2-cyclopentyl-2-hydroxy-2-phenylacetamide, (2R)-N-[1-(4-methyl-3-pentenyl)piperidin-4-yl]-2-(1-cyclopenten-1-yl)-2-hydroxy-2-phenylacetamide,

[1-(4-methyl-3-pentenyl)piperidin-4-yl] 2-cyclobutyl-2-hydroxy-2-phenylacetate,

[(4-methylpentyl)piperidin-4-yl] 2-cyclobutyl-2-hydroxy-2-phenylacetate,

[1-(1-cyclohexylethyl)piperidin-4-yl] 2-cyclobutyl-2-hydroxy-2-phenylacetate, (2R)-N-{1-[(4S)-4-methylhexyl]piperidin-4-yl}-2-cyclobutyl-2-hydroxy-2-phenylacetamide,

[1-(3-cyclopentylidenepropyl)-piperidin-4-yl] 2-cyclobutyl-2-hydroxy-2-phenylacetate, N-[(E)-1-(4-methyl-4-hexenyl)piperidin-4-yl]-2-cyclobutyl-2-hydroxy-2-phenylacetamide,
N-[(Z)-1-(4-methyl-4-hexenyl)piperidin-4-yl]-2-cyclobutyl-2-hydroxy-2-phenylacetamide,
(2R)-N-[1-(4-methyl-3-pentenyl)piperidin-4-yl]-2-cyclobutyl-2-hydroxy-2-phenylacetamide,
N-{1-[(4S)-4-methylhexyl]piperidin-4-yl}-2-cyclobutyl-2-hydroxy-2-phenylacetamide,
N-[1-(4-methyl-3-pentenyl)piperidin-4-yl]-2-cyclopentyl-2-hydroxy-2-phenylacetamide,
(2R)-N-[1-(4-methyl-3-pentenyl)piperidin-4-yl]-2-cyclopentyl-2-hydroxy-2-phenylacetamide,
(2R)-N-{1-[(4S)-4-methylhexyl]piperidin-4-yl}-2-cyclopentyl-2-hydroxy-2-phenylacetamide,
N-[1-(E)-(4-methyl-2-pentenyl)piperidin-4-yl]-2-cyclopentyl-2-hydroxy-2-phenylacetamide,
N-[1-(E)-(4-methyl-2-hexenyl)piperidin-4-yl]-2-cyclopentyl-2-hydroxy-2-phenylacetamide,
N-[1-(cyclohexylmethyl)piperidin-4-yl]-2-cyclopentyl-2-hydroxy-2-phenylacetamide,
N-[1-(cycloheptylmethyl)piperidin-4-yl]-2-cyclopentyl-2-hydroxy-2-phenylacetamide,
(2R)-N-[1-(cycloheptylmethyl)piperidin-4-yl]-2-cyclopentyl-2-hydroxy-2-phenylacetamide,
N-[1-(1-cycloheptenylmethyl)piperidin-4-yl]-2-cyclopentyl-2-hydroxy-2-phenylacetamide,
N-[1-(1-cyclohexenylmethyl)piperidin-4-yl]-2-cyclopentyl-2-hydroxy-2-phenylacetamide,
N-[1-(cyclopentylmethyl)piperidin-4-yl]-2-cyclopentyl-2-hydroxy-2-phenylacetamide,
N-[1-(1-cyclopentenylmethyl)piperidin-4-yl]-2-cyclopentyl-2-hydroxy-2-phenylacetamide,
N-[1-(3-methyl-1-cyclohexenylmethyl)piperidin-4-yl]-2-cyclopentyl-2-hydroxyl-2-phenylacetamide,
N-[1-(4-methyl-1-cyclohexylmethyl)piperidin-4-yl]-2-cyclopentyl-2-hydroxy-2-phenylacetamide,
N-[1-(2-cyclohexylmethyl)piperidin-4-yl]-2-cyclopentyl-2-hydroxy-2-phenylacetamide,
N-(1-pentylpiperidin-4-yl)-2-cyclopentyl-2-hydroxy-2-phenylacetamide,
N-[1-(trans-3-methylcyclohexylmethyl)piperidin-4-yl]-2-cyclopentyl-2-hydroxy-2-phenylacetamide,
N-[1-(cis-3-methylcyclohexylmethyl)piperidin-4-yl]-2-cyclopentyl-2-hydroxy-2-phenylacetamide,
N-[1-(3-methyl-1-cyclopentenylmethyl)piperidin-4-yl]-2-cyclopentyl-2-hydroxy-2-phenylacetamide,
N-[1-(4-methyl-3-pentenyl)piperidin-4-yl]-2-cyclopentyl-2-hydroxy-2-(2-thienyl)acetamide,
N-[1-(4-methyl-3-pentenyl)piperidin-4-yl]-2-cyclopentyl-2-hydroxy-2-(3-thienyl)acetamide,
N-[1-(4-methyl-3-pentenyl)piperidin-4-yl]-2-cyclopentyl-2-(3-furyl)-2-hydroxyacetamide,
N-[1-(4-methyl-3-pentenyl)piperidin-4-yl]-2-cyclopentyl-2-(2-furyl)-2-hydroxyacetamide,
N-[1-(4-methyl-3-pentenyl)piperidin-4-yl]-2-cyclopentyl-2-hydroxy-2-(2-thiazolyl)acetamide,
N-[1-(4-methyl-3-pentenyl)piperidin-4-yl]-2-cyclopentyl-2-hydroxy-2-(2-pyridyl)acetamide,
N-[1-(4-methyl-3-pentenyl)piperidin-4-yl]-2-cyclopentyl-2-(3-fluorophenyl)-2-hydroxyacetamide,
N-[1-(4-methyl-3-pentenyl)piperidin-4-yl]-2-cyclopentyl-2-(2-fluorophenyl)-2-hydroxyacetamide,
N-[1-(4-methyl-3-pentenyl)piperidin-4-yl]-2-cyclopentyl-2-(4-fluorophenyl)-2-hydroxyacetamide,
N-[1-(4-methyl-3-pentenyl)piperidin-4-yl]-2-(2-imidazolyl)-2-cyclopentyl-2-hydroxyacetamide,
N-[1-(4-methyl-3-pentenyl)piperidin-4-yl]-2-cyclopentyl-2-hydroxy-2-(5-thiazolyl)acetamide,
N-[1-(4-methyl-3-pentenyl)piperidin-4-yl]-2-cyclopentyl-2-hydroxy-2-(2-pyrrolyl)acetamide,
N-[1-(4-methyl-3-pentenyl)piperidin-4-yl]-2-cyclopentyl-2-hydroxy-2-(4-pyrimidinyl)acetamide,
N-[1-(cycloheptylmethyl)piperidin-4-yl]-2-cyclopentyl-2-hydroxy-2-(5-thiazolyl)acetamide,
N-[1-(cycloheptylmethyl)piperidin-4-yl]-2-cyclopentyl-2-hydroxy-2-(2-thienyl)acetamide,
N-[1-(cycloheptylmethyl)piperidin-4-yl]-2-(2-furyl)-2-cyclopentyl-2-hydroxyacetamide,
N-[1-(cycloheptylmethyl)piperidin-4-yl]-2-cyclopentyl-2-hydroxy-2-(2-thiazolyl)acetamide,
N-[1-(cycloheptylmethyl)piperidin-4-yl]-2-cyclopentyl-2-hydroxyl-2-(3-thienyl)acetamide,
N-[1-(cycloheptylmethyl)piperidin-4-yl]-2-cyclopentyl-2-hydroxy-2-(2-pyridyl)acetamide,
N-[1-(cycloheptylmethyl)piperidin-4-yl]-2-(3-fluorophenyl)-2-cyclopentyl-2-hydroxyacetamide,
N-[1-(cycloheptylmethyl)piperidin-4-yl]-2-(2-fluorophenyl)-2-cyclopentyl-2-hydroxyacetamide,
N-[1-(cycloheptylmethyl)piperidin-4-yl]-2-cyclopentyl-2-(4-fluorophenyl)-2-hydroxyacetamide,
N-[1-(2-cyclopentylethyl)piperidin-4-yl]-2-cyclopentyl-2-hydroxy-2-phenylacetamide,
N-[1-(2-cyclooctylmethyl)piperidin-4-yl]-2-cyclopentyl-2-hydroxy-2-phenylacetamide,
N-[1-(4-methylpentyl)piperidin-4-yl]-2-cyclopentyl-2-(2-fluorophenyl)-2-hydroxyacetamide,
N-[1-(trans-4-methylcyclopentylmethyl)piperidin-4-yl]-2-cyclopentyl-2-(2-fluorophenyl)-2-hydroxyacetamide and
N-[1-(bicyclo[3.3.0]oct-3-ylmethyl)piperidin-4-yl]-2-cyclopentyl-2-hydroxy-2-phenylacetamide, and the pharmaceutically acceptable salts thereof.

8. (2R)-N-[1-(4-methyl-3-pentenyl)piperidin-4-yl]-2-cyclopentyl-2-hydroxy-2-phenylacetamide, or a pharmaceutically acceptable salt thereof.

9. A pharmaceutical composition comprising an anticholinergic effective amount of a 1,4-di-substituted piperidine of formula [I] as set forth in claim 1, or a pharmaceutically acceptable salt thereof, and at least one pharmaceutically acceptable adjuvant.

10. The composition of claim 9 wherein the amount of the 1,4-di-substituted piperidine of formula [I] is from 1.0 to 60 percent by weight of the composition.

11. A method for the treatment or prophylaxis of asthma, chronic airway obstruction, fibroid lung, urination disorders, irritable colon, or spasm or hyperanakinesis of the digestive tract, in a patient in need thereof, which comprises administering to said patient, an anticholinergic effective amount of a 1,4-di-substituted piperidine of formula [I] as set forth in claim 1, or a pharmaceutically acceptable salt thereof.

12. The compound of claim 5 wherein Ar is a phenyl group or a heteroaromatic group selected from the group consisting of 2-pyrrolyl, 3-pyrrolyl, 2-furyl, 3-furyl, 2-thienyl, 3-thienyl, 3-pyrazolyl, 4-pyrazolyl, 3-isoxazolyl, 5-isoxazolyl, 2-imidazolyl, 4-imidazolyl, 2-oxazolyl, 4-oxazolyl, 5-oxazolyl, 2-thiazolyl, 4-thiazolyl, 5-thiazolyl, 2-pyridyl, 4-pyridyl, 2-pyrimidinyl and 4-pyrimidinyl, in which one or two optional hydrogen atoms on the ring may be replaced by substituent groups selected from the group consisting of a fluorine and a methyl group;

$R^1$ is a cycloalkyl group of 3 to 6 carbon atoms or a cycloalkenyl group of 3 to 6 carbon atoms; and, X is NH.

13. The compound of claim 12 wherein $R^2$ is a linear or branched $C_5$–$C_{15}$ alkyl, $C_5$–$C_{15}$ alkenyl or $C_5$–$C_{15}$ alkynyl group, a $C_5$–$C_{15}$ cycloalkylalkyl or $C_5$–$C_{15}$ cycloalkylalkenyl group in which an optional hydrogen atom(s) on the cycloalkyl ring may be replaced by a lower alkyl group(s), a $C_5$–$C_{15}$ bicycloalkylalkyl or $C_5$–$C_{15}$ bicycloalkylalkenyl group in which an optional hydrogen atom(s) on the bicycloalkyl ring may be replaced by a lower alkyl group(s), a $C_5$–$C_{15}$ cycloalkenylalkyl or $C_5$–$C_{15}$ cycloalkenylalkenyl group in which an optional hydrogen atom(s) on the cycloalkenyl ring may be replaced by a lower alkyl group(s), a $C_5$–$C_{15}$ bicycloalkenylalkyl or $C_5$–$C_{15}$ bicycloalkenylalkenyl group in which an optional hydrogen atom(s) on the bicycloalkenyl ring may be replaced by a lower alkyl group(s), or a $C_5$–$C_{15}$ cycloalkenylalkenyl or $C_5$–$C_{15}$ cycloalkenylalkenyl group.

14. The compound of claim 13 wherein $R^1$ is a cyclopropyl, cyclobutyl, cyclopentyl or cyclopentenyl group.

15. A process for the preparation of a 1,4-di-substituted piperidine derivative of the formula [I] as claimed in claim 1 which comprises:

(a) reacting a carboxylic acid of the general formula [III]

wherein Ar and $R^1$ are as defined above, or a reactive derivative thereof with a compound of the general formula [IV]

wherein $R^{20}$ represents a saturated or unsaturated aliphatic hydrocarbon radical of 5 to 15 carbon atoms or a saturated or unsaturated aliphatic hydrocarbon radical of 2 to 14 carbon atoms having a protected or unprotected oxo group, and X is as defined above, or a salt thereof; and when $R^{20}$ is a saturated or unsaturated aliphatic hydrocarbon radical of 2 to 14 carbon atoms having a protected or unprotected oxo group, deprotecting the resulting product where necessary, subjecting it to the Wittig reaction, and reducing the existing double bond where necessary;

(b) reacting a carboxylic acid of the above general formula [III] or a reactive derivative thereof with a compound of the general formula [V]

wherein E is a protective group for the imino group, and X is as defined above, or a salt thereof; deprotecting the resulting compound of the general formula [VI]

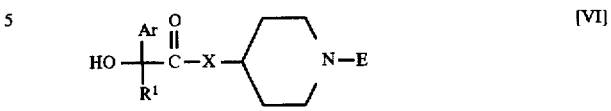

wherein Ar, $R^1$, X and E are as defined above; reacting the compound of the general formula [VI] with a compound of the general formula [VII] or [VIII]

or

wherein $R^{21}$ and $R^{22}$ may be the same or different and each represent a hydrogen atom or a lower alkyl group, $R^{23}$ represents a hydrogen atom or a saturated or unsaturated aliphatic hydrocarbon radical of 1 to 12 carbon atoms, L represents a leaving group, and $R^{20}$ is as defined above, if necessary, in the presence of a base; and when a compound of the general formula [VII] in which $R^{20}$ is a saturated or unsaturated aliphatic hydrocarbon radical of 2 to 14 carbon atoms having a protected or unprotected oxo group or a compound of the general formula [VIII] is reacted, deprotecting the resulting product where necessary, subjecting it to the Wittig reaction, and reducing the existing double bond where necessary; or (c) deprotecting a compound of the above general formula [VI] and subjecting it to a reductive alkylation reaction with a compound of the general formula [IX]

wherein $R^{24}$ represents a saturated or unsaturated aliphatic hydrocarbon radical of 4 to 14 carbon atoms.

16. The process according to claim 15, which comprises the reaction (a).

17. The process according to claim 15, which comprises the reaction (b).

18. The process according to claim 15, which comprises the reaction (c).

* * * * *